United States Patent
Den Haan et al.

(10) Patent No.: US 9,447,398 B2
(45) Date of Patent: Sep. 20, 2016

(54) HETEROLOGOUS EXPRESSION OF FUNGAL CELLOBIOHYDROLASE 2 GENES IN YEAST

(75) Inventors: Riaan Den Haan, Durbanville (ZA); Emile Van Zyl, Stellenbosch (ZA)

(73) Assignee: Stellenbosch University, Stellenbosch (ZA)

( * ) Notice: Subject to any disclaimer, the term of this patent is extended or adjusted under 35 U.S.C. 154(b) by 698 days.

(21) Appl. No.: 13/640,233

(22) PCT Filed: Oct. 25, 2010

(86) PCT No.: PCT/IB2010/002904
§ 371 (c)(1),
(2), (4) Date: Apr. 19, 2013

(87) PCT Pub. No.: WO2011/051806
PCT Pub. Date: May 5, 2011

(65) Prior Publication Data
US 2013/0217072 A1    Aug. 22, 2013

Related U.S. Application Data

(60) Provisional application No. 61/254,935, filed on Oct. 26, 2009.

(51) Int. Cl.
| | | |
|---|---|---|
| C12P 7/10 | (2006.01) | |
| C12P 19/02 | (2006.01) | |
| C12P 19/14 | (2006.01) | |
| C12P 39/00 | (2006.01) | |
| C12P 7/14 | (2006.01) | |
| C12N 9/42 | (2006.01) | |

(52) U.S. Cl.
CPC ........... *C12N 9/2437* (2013.01); *C12N 9/2445* (2013.01); *C12P 7/10* (2013.01); *C12P 7/14* (2013.01); *C12P 19/02* (2013.01); *C12P 19/14* (2013.01); *C12P 39/00* (2013.01); *C12Y 302/01021* (2013.01); *C12Y 302/01091* (2013.01); *Y02E 50/16* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 8,470,592 | B2 | 6/2013 | Brevnova et al. |
| 2010/0075363 | A1 | 3/2010 | McBride et al. |
| 2011/0124074 | A1 | 5/2011 | Den Haan et al. |
| 2011/0189744 | A1 | 8/2011 | McBride et al. |
| 2012/0003701 | A1 | 1/2012 | Brevnova et al. |
| 2012/0040409 | A1 | 2/2012 | Hau et al. |
| 2012/0129229 | A1 | 5/2012 | McBride et al. |
| 2013/0230888 | A1 | 9/2013 | Den Haan et al. |

FOREIGN PATENT DOCUMENTS

| | | |
|---|---|---|
| WO | 92/03560 A1 | 3/1992 |
| WO | 93/24631 A1 | 12/1993 |
| WO | WO 2008/064314 A2 | 5/2008 |
| WO | WO 2008/137958 A1 | 11/2008 |
| WO | WO 2009/138877 A2 | 11/2009 |
| WO | WO 2009/139839 A1 | 11/2009 |
| WO | WO 2010/005551 A2 | 1/2010 |
| WO | WO 2010/005553 A1 | 1/2010 |
| WO | WO 2010/060056 A2 | 5/2010 |
| WO | WO 2010/075529 A2 | 7/2010 |
| WO | WO 2011/051806 A2 | 5/2011 |

OTHER PUBLICATIONS

Kurtzman et al. (Retrieved from the internet: <<http://www.ars.usda.gov/research/publications/publications.htm?SEQ_NO_115=176765>>, retrieved on Feb. 12, 2015, abstract only).*
Carbone, A., et al., "Codon adaptation index as a measure of dominating codon bias," *Bioinformatics* 19(16):2005-15, Oxford University Press, England (2003).
Davies, G. and Henrissat, B., "Structures and mechanisms of glycosyl hydrolases," *Structure* 3(9):853-59, Current Biology Ltd, England (1995).
Den Haan, R., et al., "Functional expression of cellobiohydrolases in *Saccharomyces cerevisiae* towards one-step conversion of cellulose to ethanol," *Enzyme and Microbial Technology* 40:1291-99, Elsevier Inc., United States (2007).
Fujita, Y., et al., "Synergistic Saccharification, and Direct Fermentation to Ethanol, of Amorphous Cellulose by Use of an Engineered Yeast Strain Codisplaying Three Types of Cellulolytic Enzyme," *Appl. Environ. Microbiol.* 70(2):1207-12, American Society for Microbiology, United States (2004).
Grassick, A., et al., "Three-dimensional structure of a thermostable native cellobiohydrolase, CBH IB, and molecular characterization of the cel7 gene from the filamentous fungus, *Talaromyces emersonii*," *Eur. J Biochem.* 271:4495-4506, FEBS, England (2004).
Henrissat, B., et al., "Conserved catalytic machinery and the prediction of a common fold for several families of glycosyl hydrolases," *Proc. Natl. Acad. Sci. USA* 92:7090-94, National Academy of Sciences, United States (1995).

(Continued)

*Primary Examiner* — Suzanne M Noakes
*Assistant Examiner* — Jae W Lee
(74) *Attorney, Agent, or Firm* — Nutter McClennen & Fish LLP

(57) ABSTRACT

The present invention provides for heterologous expression of polypeptides encoded by wild-type and codon-optimized cbh2 genes from the organisms *Cochliobolus heterostrophus*, *Gibberella zeae*, *Irpex lacteus*, *Volvariella volvacea*, and *Piromyces* sp. in host cells, such as the yeast *Saccharomyces cerevisiae*. The expression in such host cells of the corresponding genes, and variants and combinations thereof, result in improved specific activity of the expressed cellobiohydrolases. Thus, such genes and expression systems are useful for efficient and cost-effective consolidated bioprocessing systems.

20 Claims, 3 Drawing Sheets

(56) References Cited

OTHER PUBLICATIONS

Figure 1:
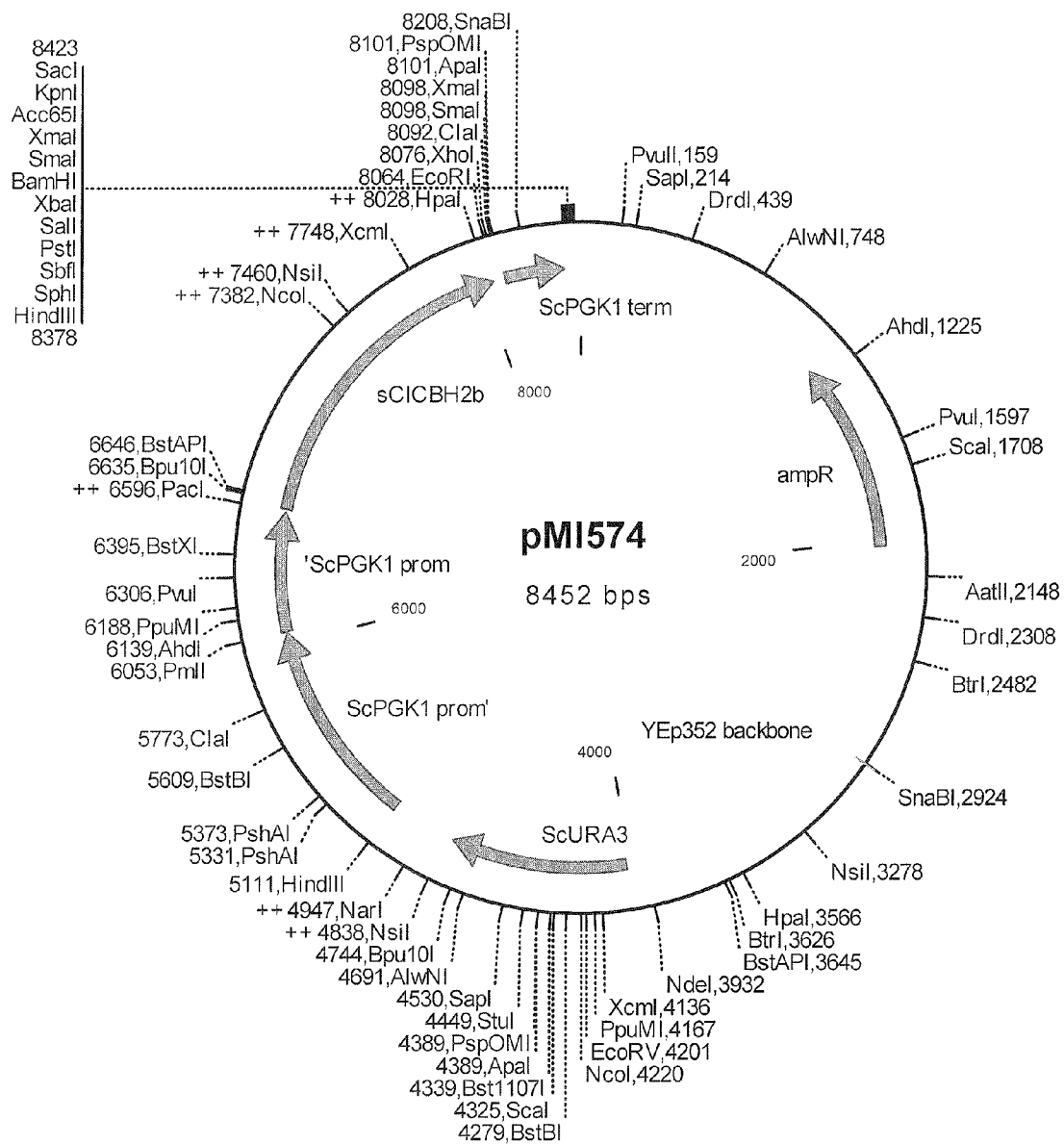

Kotula, L. and Curtis, P.J., "Evaluation of Foreign Gene Codon Optimization in Yeast: Expression of a Mouse Ig Kappa Chain," *Bio/technology* 9:13 86-89, Nature Pub. Co., United States (1991).
Lev, S. and Horwitz, B.A., "A Mitogen-Activated Protein Kinase Pathway Modulates the Expression of Two Cellulase Genes in *Cochliobolus heterostrophus* during Plant Infection," *The Plant Cell* 15:835-44, American Society of Plant Biologists, United States (2003).
McBride, J.E., et al., "Utilization of cellobiose by recombinant β-glucosidase-expressing strains of *Saccharomyces cerevisiae*: characterization and evaluation of the sufficiency of expression," *Enzyme and Microbial Technology* 37:93-101, Elsevier Inc., United States (2005).
Nakamura, Y., et al., "Codon usage tabulated from international DNA sequence databases: status for the year 2000," *Nucleic Acids Res.* 28(1):292, Oxford University Press, England (2000).
Penttilä, M.E., et al., "Efficient secretion of two fungal cellobiohydrolases by *Saccharomyces cerevisiae*," *Gene* 63:103-12, Elsevier Science Publishers B.V., Netherlands (1988).
Sharp, P.M. and Li, W.-H., "The codon adaptation index—a measure of directional synonymous codon usage bias, and its potential applications," *Nucleic Acids Res.* 15(3):1281-95, IRL Press Limited, England (1987).
Van Rensburg, P., et al., "Engineering Yeast for Efficient Cellulose Degradation," *Yeast* 14:67-76, John Wiley & Sons, Ltd., England (1998).
Van Rooyen, R., et al., "Construction of cellobiose-growing and fermenting *Saccharomyces cerevisiae* strains," *J. Biotechnol.* 120:284-95, Elsevier B.V., Netherlands (2005).
Van Zyl, W.H., et al., "Consolidated Bioprocessing for Bioethanol Production Using *Saccharomyces cerevisiae*," *Adv. Biochem. Engin./Biotechnol.* 108:205-35, Springer-Verlag, Germany (2007).
Accession No. AY116307, Lev, S. and Horowitz, B.A., GenBank Database, 2 pages, printed from ncbi.nlm.nih.gov/nuccore/AY116307 on Jul. 24, 2013.
International Search Report and The Written Opinion of the International Searching Authority for International Application No. PCT/IB2010/002904, European Patent Office, mailed Apr. 13, 2011.
International Preliminary Report on Patentability for International Application No. PCT/IB2010/002904, The International Bureau of WIPO, issued May 1, 2012.
Tomme, P., et al., "Studies of the cellulolytic system of *Trichoderma reesei* QM 9414: Analysis of domain function in two cellobiohydrolases by limited proteolysis," *Eur. J. Biochem.* 170:575-81, FEBS, England (1988).
Accession No. AAM76664.1, Lev, S. and Horowitz, B.A., GenBank Database, 1 page, printed from ncbi.nlm.nih.gov/protein/aam76664.1 on Mar. 18, 2014.
Bowie, J.U., et al., Deciphering the Message in Protein Sequences: Tolerance to Amino Acid Substitutions. Science, 1990;247:1306-1310, Science, United States.
Brutlag, D.L., et al., Improved Sensitivity of Biological Sequence Database Searches. Comp. App. Biosci. 1990;6:237-245, Oxford Univ. Press, United Kingdom.
Cho, K.M., et at., Delta-Integration of endo/exo-glucanase and beta-glucosidase genes into the yeast chromosomes for direct conversion of cellulose to ethanol. Enzyme and Microbial Technology, 1999;25:23-30, Elsevier, Netherlands.
Cunningham, B.C., et al., High-Resolution Epitope Mapping of hGH-Receptor Interactions by Alanine-Scanning Mutagenesis. Science, 1989;244:1081-1085, American Association for the Advancement of Science, United States.
Frohman, M.A., et al., Rapid production of full-length cDNAs from rare transcripts: amplification using a single gene-specific oligonucleotide primer. Proc Natl Acad Sci U S A. Dec. 1988;85(23):8998-9002.
Laemmli, U.K., Cleavage of structural proteins during the assembly of the head of bacteriophage T4. Nature. Aug. 15, 1970;227(5259):680-5.
Loh, E.Y., et al., Polymerase chain reaction with single-sided specificity: analysis of T cell receptor delta chain. Science. Jan. 13, 1989;243(4888):217-20.
Ohara, O., et al., One-sided polymerase chain reaction: the amplification of cDNA. Proc Natl Acad Sci U S A. Aug. 1989;86(15):5673-7.
Tabor, S., et al., A bacteriophage T7 RNA polymerase/promoter system for controlled exclusive expression of specific genes. Proc Natl Acad Sci U S A. Feb. 1985;82(4):1074-8.
Walker, G.T., et al., Isothermal in vitro amplification of DNA by a restriction enzyme/DNA polymerase system. Proc Natl Acad Sci U S A. Jan. 1, 1992;89(1):392-6.

\* cited by examiner

HETEROLOGOUS EXPRESSION OF FUNGAL CELLOBIOHYDROLASE 2 GENES IN YEAST

This is a U.S. National Phase of International Appl. No. PCT/IB2010/002904, filed Oct. 25, 2010, which claims the benefit of U.S. Provisional Appl. No. 61/254,935, filed Oct. 26, 2009, each of which is hereby incorporated by reference in its entirety.

REFERENCE TO A SEQUENCE LISTING SUBMITTED ELECTRONICALLY VIA EFS-WEB

The content of the electronically submitted sequence listing (Name: sequencelisting.ascii.txt, Size: 127,248 bytes; and Date of Creation: Oct. 15, 2010) is herein incorporated by reference in its entirety.

BACKGROUND OF THE INVENTION

Lignocellulosic biomass is widely recognized as a promising source of raw material for production of renewable fuels and chemicals. The primary obstacle impeding the more widespread production of energy from biomass feedstocks is the general absence of low-cost technology for overcoming the recalcitrance of these materials to conversion into useful fuels. Lignocellulosic biomass contains carbohydrate fractions (e.g., cellulose and hemicellulose) that can be converted into ethanol. In order to convert these fractions, the cellulose and hemicellulose must ultimately be converted or hydrolyzed into monosaccharides; it is the hydrolysis that has historically proven to be problematic.

Biologically mediated processes are promising for energy conversion, in particular for the conversion of lignocellulosic biomass into fuels. Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called consolidated bioprocessing (CBP), which is distinguished from other less highly integrated configurations in that it does not involve a dedicated process step for cellulase and/or hemicellulase production. CBP offers the potential for lower cost and higher efficiency than processes featuring dedicated cellulase production. The benefits result in part from avoided capital costs, substrate and other raw materials, and utilities associated with cellulase production.

Bakers' yeast (*Saccharomyces cerevisiae*) remains the preferred micro-organism for the production of ethanol (Van Zyl, W. H., et al., *Adv. Biochem. Eng. Biotechnol.* 108, 205-235 (2007)). Attributes in favor of this microbe are (i) high productivity at close to theoretical yields (0.51 g ethanol produced/g glucose used), (ii) high osmo- and ethanol tolerance, (iii) natural robustness in industrial processes, (iv) being generally regarded as safe (GRAS) due to its long association with wine and bread making and beer brewing. Furthermore, *S. cerevisiae* exhibits tolerance to inhibitors commonly found in hydrolyzates resulting from biomass pretreatment. The major shortcoming of *S. cerevisiae* is its inability to utilize complex polysaccharides such as cellulose, or its break-down products, such as cellobiose and cellodextrins. One strategy for developing CBP-enabling microorganisms such as *S. cerevisiae* is by engineering them to express a heterologous cellulase and/or a hemicelluase system.

Three major types of enzymatic activities are required for native cellulose degradation: The first type is endoglucanases (1,4-β-D-glucan 4-glucanohydrolases; EC 3.2.1.4). Endoglucanases (Eg) cut at random in the cellulose polysaccharide chain of amorphous cellulose, generating oligosaccharides of varying lengths and consequently new chain ends. The second type is β-glucosidases (β-glucoside glucohydrolases; EC 3.2.1.21). β-Glucosidases (Bgl) hydrolyze soluble cellodextrins and cellobiose to glucose units. The third type is exoglucanases. Exogluconases include cellodextrinases (1,4-β-D-glucan glucanohydrolases; EC 3.2.1.74) and cellobiohydrolases (1,4-β-D-glucan cellobiohydrolases; EC 3.2.1.91). Exoglucanases act in a processive manner on the reducing or non-reducing ends of cellulose polysaccharide chains, liberating either glucose (glucanohydrolases) or cellobiose (cellobiohydrolase) as major products. Exoglucanases can also act on microcrystalline cellulose, presumably peeling cellulose chains from the microcrystalline structure. Classically, exoglucanases such as the cellobiohydrolases (Cbh) possess tunnel-like active sites, which can only accept a substrate chain via its terminal regions. These exo-acting Cbh enzymes act by threading the cellulose chain through the tunnel, where successive cellobiose units are removed in a sequential manner. Sequential hydrolysis of a cellulose chain is termed "processivity."

Structurally, cellulases generally consist of a catalytic domain joined to a cellulose-binding module (CBM) via a linker region that is rich in proline and/or hydroxy-amino acids. In type I exoglucanases, the CBM domain is found at the C-terminal extremity of these enzyme (this short domain forms a hairpin loop structure stabilised by 2 disulphide bridges). In type 2 CBHs, the CBM is found at the N-terminus. In some cases, however, cellulases do not contain a CBM, and only contain a catalytic domain. Examples of such CBM-lacking cellulases include Cbhs from *Humicola grisea*, *Phanerochaete chrysosporium* and *Aspergillus niger*. Grassick et al., *Eur. J. Biochem.* 271: 4495-4506 (2004).

Cbh2s are classified as family 6 glycosyl hydrolases. Glycosyl hydrolases are a widespread group of enzymes that hydrolyse the glycosidic bond between two or more carbohydrates, or between a carbohydrate and a non-carbohydrate moiety. A classification system for glycosyl hydrolases, based on sequence similarity, has led to the definition of 85 different families (Henrissat, B. et al., *Proc. Natl. Acad. Sci.* 92:7090-7094 (1995); Davies, G. and Henrissat, B., *Structure* 3: 853-859 (1995)). Glycoside hydrolase family 6 (GHF6) comprises enzymes with several known activities including endoglucanase (EC:3.2.1.4) and cellobiohydrolase (EC:3.2.1.91).

With the aid of recombinant DNA technology, several of these heterologous cellulases from bacterial and fungal sources have been transferred to *S. cerevisiae*, enabling the degradation of cellulosic derivatives (Van Rensburg, P., et al., *Yeast* 14: 67-76 (1998)), or growth on cellobiose (Van Rooyen, R., et al., *J. Biotech.* 120, 284-295 (2005)); McBride, J. E., et al., *Enzyme Microb. Techol.* 37, 93-101 (2005)).

Related work was described by Fujita, Y., et al., (*Appl. Environ. Microbiol.* 70, 1207-1212 (2004)) where cellulases immobilized on the yeast cell surface had significant limitations. First, Fujita et al. were unable to achieve fermentation of amorphous cellulose using yeast expressing only recombinant Bgl1 and EgII. A second limitation of the Fujita et al. approach was that cells had to be pre-grown to high cell density on standard carbon sources before the cells were useful for ethanol production using amorphous cellulose (e.g., Fujita et al. uses high biomass loadings of ~15 g/L to accomplish ethanol production).

As noted above, ethanol producing yeast such as *S. cerevisiae* require addition of external cellulases when cultivated on cellulosic substrates, such as pre-treated wood, because this yeast does not produce endogenous cellulases. Expression of fungal cellulases such as *T. reesei* Cbh1 and Cbh2 in yeast *S. cerevisiae* has been shown to be functional. Den Haan, R., et al., *Enzyme and Microbial Technology* 40:1291-1299 (2007). However, current levels of expression and specific activity of cellulases heterologously expressed in yeast are still not sufficient to enable growth and ethanol production by yeast on cellulosic substrates without externally added enzymes. While studies have shown that perhaps certain cellulases, such as *T. reesei* Cbh1, have some activity when heterologously expressed, there remains a significant need for improvement in the specific activity of heterologously expressed Cbhs in order to attain the goal of achieving a consolidated bioprocessing (CBP) system capable of efficiently and cost-effectively converting cellulosic substrates to ethanol.

Currently, there is no reliable way to predict which cellulases will be efficiently expressed in heterologous organisms. For example, despite the fact that *T. reesei* Cbh1 and *T. emersonii* Cbh1 are both endogenously expressed at high levels, heterologous expression of these proteins in yeast yielded disparate results. *T. emersonii* Cbh1 expression in yeast was significantly greater in yeast than *T. reesei* Cbh1 under similar conditions. See International Application No. PCT/IB2009/005881, filed May 11, 2009. Efficient expression may depend, for example, on chaperone proteins that differ in the heterologous organisms and in the cellulase's native organism. Furthermore, even cellulases which are expressed at high levels may not be particularly active in a heterologous organism. For example a cellulase may be subject to different post-translational modifications in the heterologous host organism than the in native organism from which the cellulase is derived. Protein folding and secretion can also be a barrier to heterologous cellulase expression.

Therefore, in order to address the limitations of heterologous Cbh expression in consolidated bioprocessing systems, the present invention provides for heterologous expression of wild-type and codon-optimized variants of Cbh2 from the fungal organisms *Cochliobolus heterostrophus*, *Gibberella zeae*, *Irpex lacteus*, *Volvariella volvacea*, and *Piromyces* sp. in host cells, such as the yeast *Saccharomyces cerevisiae*. The expression in such host cells of the corresponding genes, and variants and combinations thereof, result in improved specific activity of the expressed cellobiohydrolases. Thus, such genes and expression systems are useful for efficient and cost-effective consolidated bioprocessing systems.

BRIEF SUMMARY OF THE INVENTION

The present invention provides for the heterologous expression of *Cochliobolus heterostrophus*, *Gibberella zeae*, *Irpex lacteus*, *Volvariella volvacea*, and *Piromyces* sp. cellobiohydrolases, or fragments thereof in host cells, such as the yeast *Saccharomyces cerevisiae*. The cellobiohydrolase can be a Cbh2, such as *Cochliobolus heterostrophus* C4 cel7, *Gibberella zeae* K59 cel6, *Irpex lacteus* MC-2 cex3, *Volvariella volvacea* cbhII-1s, and *Piromyces* sp E2 cel6A.

The Cbh2 expressed in host cells of the present invention is encoded by a wild-type or codon-optimized *Cochliobolus heterostrophus*, *Gibberella zeae*, *Irpex lacteus*, *Volvariella volvacea*, or *Piromyces* sp. cbh2 polynucleotide. Codon-optimized polynucleotides can have a codon adaptation index (CAI) of about 0.8 to 1.0, about 0.9 to 1.0, or about 0.95 to 1.0.

Thus, the present invention further provides for an isolated polynucleotide comprising a nucleic acid at least about 70%, 75%, or 80% identical, at least about 90% to about 95% identical, or at least about 96%, 97%, 98%, 99% or 100% identical to a wild-type or codon-optimized *Cochliobolus heterostrophus*, *Gibberella zeae*, *Irpex lacteus*, *Volvariella volvacea*, or *Piromyces* sp. cbh2 polynucleotide, or a fragment thereof. In particular aspects, the *Cochliobolus heterostrophus*, *Gibberella zeae*, *Irpex lacteus*, *Volvariella volvacea*, or *Piromyces* sp. cbh2 is selected from the group consisting of SEQ ID NOs:1-10, or fragments, variants, or derivatives thereof. Fragments of the Cbh2s include domains such as signal peptides, cellulose binding modules (CBM), and GH family 6 domains.

In further aspects, the present invention encompasses host cells comprising heterologous polypeptides which comprise, or alternatively consist of, an amino acid sequence which is at least 80%, 85%, 90%, 95%, 96%, 97%, 98%, 99% identical to a *Cochliobolus heterostrophus*, *Gibberella zeae*, *Irpex lacteus*, *Volvariella volvacea*, or *Piromyces* sp. Cbh2, or domain, fragment, variant, or derivative thereof. In particular embodiments, the *Cochliobolus heterostrophus*, *Gibberella zeae*, *Irpex lacteus*, *Volvariella volvacea*, or *Piromyces* sp. Cbh2 is selected from the group consisting of SEQ ID NOs: 11-15.

In further aspects, the present invention encompasses vectors comprising a polynucleotide of the present invention. Such vectors include plasmids for expression in yeast, such as the yeast *Saccharomyces cerevisiae*. Yeast vectors can be YIp (yeast integrating plasmids), YRp (yeast replicating plasmids), YCp (yeast replicating plasmids with cetromere (CEN) elements incorporated), YEp (yeast episomal plasmids), or YLp (yeast linear plasmids). In certain aspects, these plasmids contain two types of selectable genes: plasmid-encoded drug-resistance genes and cloned yeast genes, where the drug resistant gene is typically used for selection in bacterial cells and the cloned yeast gene is used for selection in yeast. Drug-resistance genes include, for example, ampicillin, kanamycin, tetracycline, and neomycin. Cloned yeast genes include, for example, HIS3, LEU2, LYS2, TRP1, URA3 and TRP1. In some embodiments of the present invention, the vector is a plasmid. For example, the plasmid can be a yeast episomal plasmid or a yeast integrating plasmid.

In particular embodiments, the vector of the present invention is selected from the group consisting of pRDH150, pRDH151, pRDH152, pRDH153, and pRDH154.

In certain additional embodiments, the vector comprises a first polynucleotide encoding for a *Cochliobolus heterostrophus*, *Gibberella zeae*, *Irpex lacteus*, *Volvariella volvacea*, or *Piromyces* sp. Cbh2 and a second polynucleotide encoding for a CBM domain, for example, the CBM domain of *T. reesei* Cbh2 or *T. reesei* Cbh2.

In other embodiments of the present invention the first and second polynucleotides are contained in a single linear DNA construct. The first and second polynucleotides in the linear DNA construct can be in the same or different expression cassette.

In further embodiments, the first and second polynucleotides are in the same orientation, or the second polynucleotide is in the reverse orientation of the first polynucleotide. In additional embodiments, the first polynucleotide is either N-terminal or C-terminal to the second polynucleotide.

In certain other embodiments, the first polynucleotide and/or the second polynucleotide are encoded by codon-optimized polynucleotides, for example, polynucleotides codon-optimized for *S. cerevisiae*.

The present invention further provides for a host cell comprising a polynucleotide or a vector of the present invention from which a *Cochliobolus heterostrophus*, *Gibberella zeae*, *Irpex lacteus*, *Volvariella volvacea*, or *Piromyces* sp. cellobiohydrolase, e.g. a Cbh2, is heterologously expressed. In certain aspects, the host cell is a yeast such as *Saccharomyces cerevisiae*. In additional embodiments, the host cell further comprises one or more heterologously expressed endoglucanase polypeptides and/or one or more heterologously expressed β-glucosidase polypeptides and/or one or more heterologously expressed cellobiohydrolase polypeptides. In particular aspects, the endoglucanase polypeptide is a *C. formosanus* Eg1, the β-glucosidase polypeptide is *S. fibuligera* Bgl1, and/or the cellobiohdyrolase I is *T. emersonii* cellobiohdyrolase I.

The present invention further provides for a co-culture of host cells wherein a first cell comprising a first heterologous cellulase selected from the group consisting of a *Cochliobolus heterostrophus*, *Gibberella zeae*, *Irpex lacteus*, *Volvariella volvacea*, or *Piromyces* sp. cellobiohydrolase, e.g. a Cbh2, is cultured with a host cell expressing a second heterologous cellulase. The second heterologous cellulase can be, for example, an endoglucanase, a β-glucosidase, and/or a cellobiohydrolase. In particular aspects, the endoglucanase polypeptide is a *C. formosanus* Eg1, the β-glucosidase polypeptide is *S. fibuligera* Bgl1, and/or the cellobiohdyrolase I is *T. emersonii* cellobiohdyrolase I.

The present invention further provides for a method for hydrolyzing a cellulosic substrate, comprising contacting said cellulosic substrate with a host cell according to the present invention. In certain aspects, the cellulosic substrate is of a lignocellulosic biomass. Heterologous expression of *Cochliobolus heterostrophus*, *Gibberella zeae*, *Irpex lacteus*, *Volvariella volvacea*, or *Piromyces* sp. Cbh2 in host cells will augment cellulose hydrolysis and facilitate ethanol production by those host cells on cellulosic substrates.

BRIEF DESCRIPTION OF THE DRAWINGS/FIGURES

FIG. 1 depicts a plasmid map of pMU784. The pMU784 plasmid includes the Clcbh2b gene under the control of the *S. cerevisiae* PGK1 promoter/terminator. The gene encoding Clcbh2b was excised by means of digestions with the restriction endonucleases PadI and AscI and replaced with the alternate cellobiohydrolase 2 genes listed in Table 8. The plasmid also includes origin of replication (ori) and bla (ampicllin resistance) sequences for replication and maintenance of the plasmid in *E. coli*. In addition, an *S. ceriviseae* URA3 gene, as well as a 2-micron origin of replication are in the plasmid for selecting and replication of the plasmid in yeast.

Figure 2:
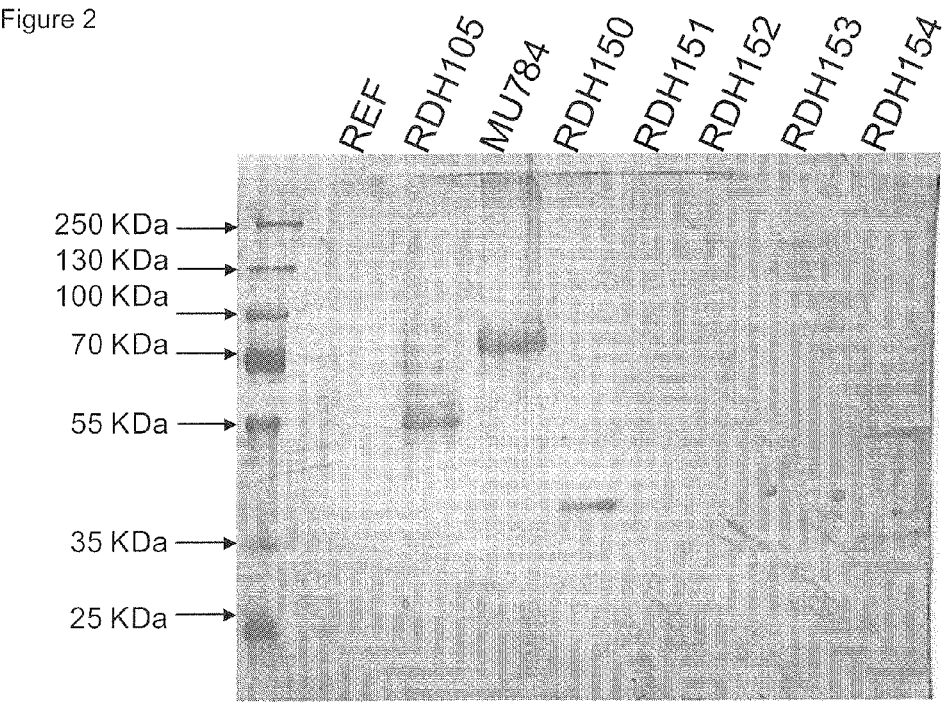

FIG. 2 depicts an SDS-Page analysis of the supernatants of Cbh2 producing strains. A strain containing a plasmid with no foreign gene was used as reference strain (REF), and the strain expressing the unmodified *T. emersonii* cbh1 (pRDH105) was included as a positive control. The strain containing the plasmid pMU784 expressing *C. lucknowense* cbh2b was also included as a positive control. Other vector names (RDH150-RDH154) refer to the plasmids expressing the genes as listed in Table 8.

Figure 3:
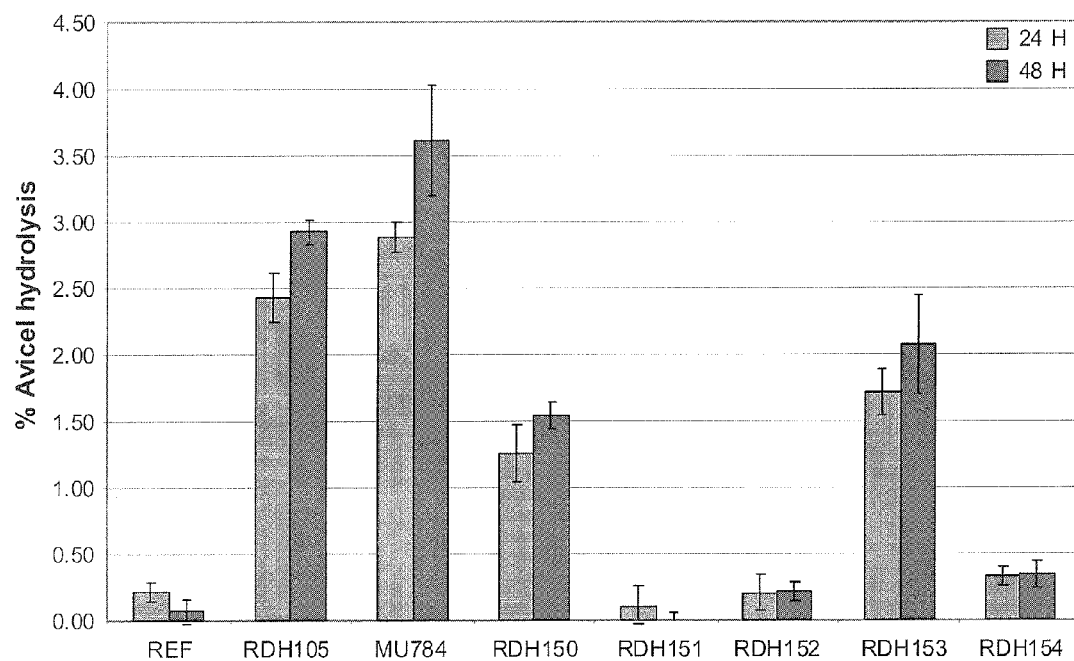

FIG. 3 depicts a bar graph showing activity of strains expressing Cbh2s on Avicel. The % Avicel hydrolysis (starting with a 1% Avicel concentration) was measured for the reference strain (REF) and strains containing a plasmid encoding a heterologous Cbh2 at 24 and 48 hour time points.

Figure 4:
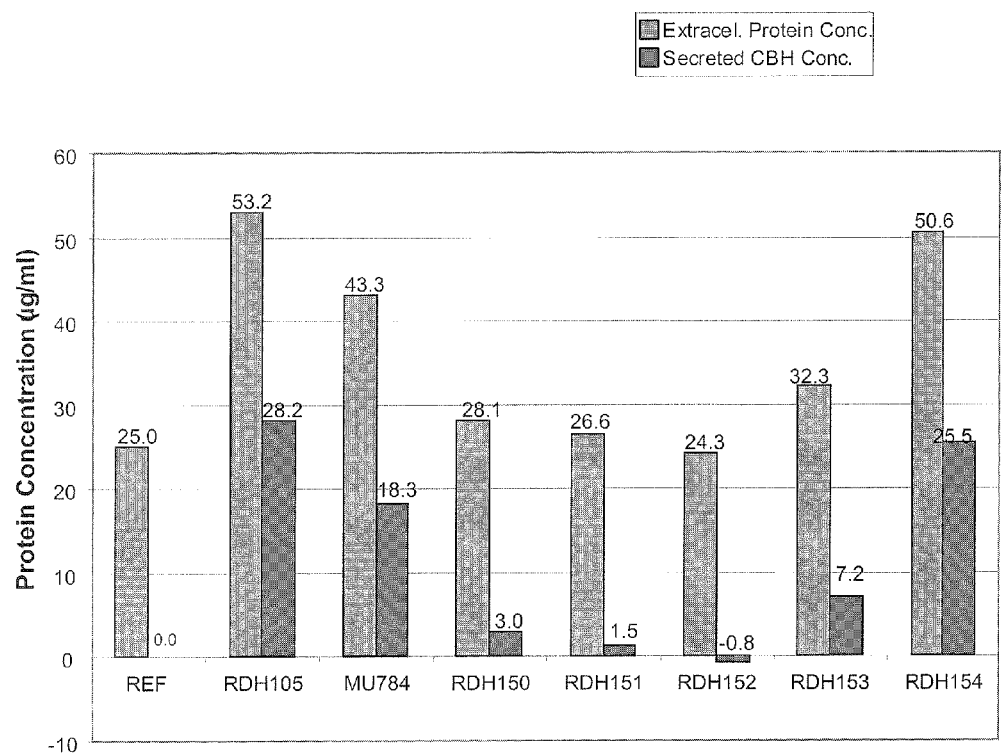

FIG. 4 depicts a bar graph showing protein levels measured using the Bradford method (BioRad). The concentrations of the total extracellular protein and the secreted Cbh2 proteins were determined for the reference strain (REF) and strains containing a plasmid encoding a heterologous Cbh2. The amount of secreted Cbh2 protein measured in the reference strain was deducted from each of the secreted Cbh2 measurements.

Figure 5:
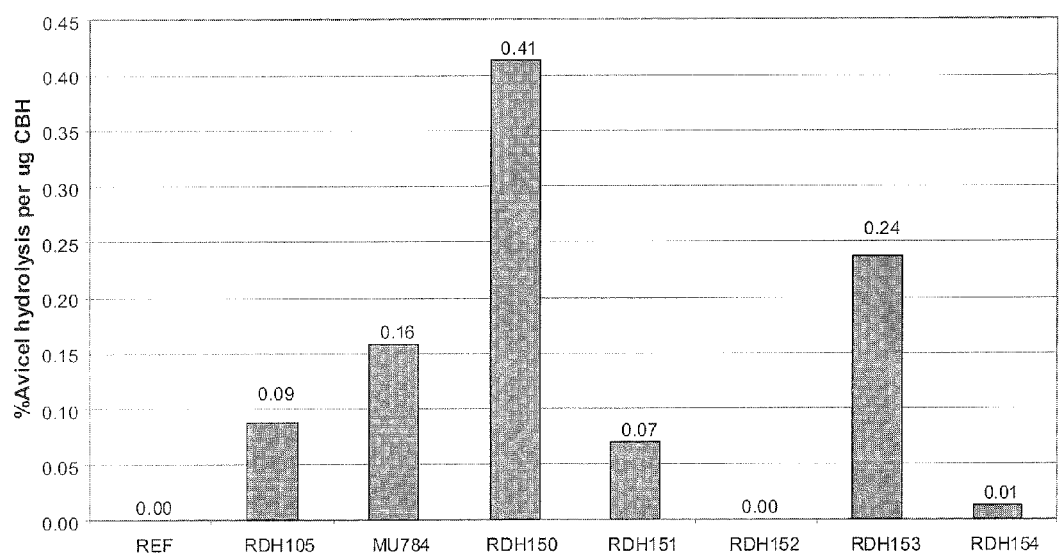

FIG. 5 depicts a bar graph showing the specific activity of heterologously expressed Cbh2s. The % Avicel hydrolysis per microgram of Cbh2 was measured for the reference strain (REF) and strains containing a plasmid encoding a heterologous Cbh2.

DETAILED DESCRIPTION OF THE INVENTION

The present invention relates to, inter alia, the heterologous expression of cbh2 genes from *Cochliobolus heterostrophus*, *Gibberella zeae*, *Irpex lacteus*, *Volvariella volvacea*, and *Piromyces* sp. in host cells, including yeast, e.g., *Saccharomyces cerevisiae*. The present invention provides important tools to enable growth of yeast on cellulosic substrates for production of products such as ethanol.

DEFINITIONS

A "vector," e.g., a "plasmid" or "YAC" (yeast artificial chromosome) refers to an extrachromosomal element often carrying one or more genes that are not part of the central metabolism of the cell. They can be in the form of a circular double-stranded DNA molecule. Such elements can be autonomously replicating sequences, genome integrating sequences, or phage sequences. Such elements can be linear, circular, or supercoiled and can be single- or double-stranded. They can also be DNA or RNA, derived from any source. They can include a number of nucleotide sequences which have been joined or recombined into a unique construction which is capable of introducing a promoter fragment and DNA sequence for a selected gene product along with appropriate 3' untranslated sequence into a cell. The plasmids or vectors of the present invention can be stable and self-replicating. The plasmids or vectors of the present invention can also be suicide vectors, or vectors that cannot replicate in the host cell. Such vectors are useful for forcing insertion of the nucleotide sequence into the host chromosome.

An "expression vector" is a vector that is capable of directing the expression of at least one polypeptide encoded by a polynucleotide sequence of the vector.

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellobiohydrolase (CBH) domains include the catalytic domain (CD) and the carbohydrate binding module (CBM).

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which can be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alfa, in linear or circular DNA molecules (e.g., restriction fragments), plasmids, and chromosomes. In discussing the structure of particular double-stranded DNA molecules, sequences are generally described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis at 11.7-11.8). In one embodiment the length for a hybridizable nucleic acid is at least about 10 nucleotides. A minimum length for a hybridizable nucleic acid can also be at least about 15 nucleotides, at least about 20 nucleotides, or at least 30 nucleotides. Furthermore, the skilled artisan will recognize that the temperature and wash solution salt concentration can be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence can include up to five point mutations per each 100 nucleotides of the reference nucleotide sequence encoding the particular polypeptide. In other words, to obtain a nucleic acid having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence.

As a practical matter, whether any particular nucleic acid molecule or polypeptide is at least 80%, 85%, 90%, 95%, 96%, 97%, 98% or 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al., *Comp. App. Biosci.* (1990) 6:237-245. In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5° end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5° or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

As known in the art, "similarity" between two polypeptides is determined by comparing the amino acid sequence and conserved amino acid substitutes thereto of the polypeptide to the sequence of a second polypeptide.

Suitable nucleic acid sequences or fragments thereof (isolated polynucleotides of the present invention) encode polypeptides that are at least about 70% to 75% identical to the amino acid sequences reported herein, at least about 80%, 85%, or 90% identical to the amino acid sequences reported herein, or at least about 95%, 96%, 97%, 98%, 99%, or 100% identical to the amino acid sequences reported herein. Suitable nucleic acid fragments are at least about 70%, 75%, or 80% identical to the nucleic acid sequences reported herein, at least about 80%, 85%, or 90% identical to the nucleic acid sequences reported herein, or at least about 95%, 96%, 97%, 98%, 99%, or 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, at least 250 amino acids, at least 300 amino acids, or at least 350 amino acids.

The term "probe" refers to a single-stranded nucleic acid molecule that can base pair with a complementary single stranded target nucleic acid to form a double-stranded molecule.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

As used herein, the term "oligonucleotide" refers to a nucleic acid, generally of about 18 nucleotides, that is hybridizable to a genomic DNA molecule, a cDNA molecule, or an mRNA molecule. Oligonucleotides can be labeled, e.g., with 32P-nucleotides or nucleotides to which a label, such as biotin, has been covalently conjugated. An oligonucleotide can be used as a probe to detect the presence of a nucleic acid according to the invention. Similarly, oligonucleotides (one or both of which can be labeled) can be used as PCR primers, either for cloning full length or a fragment of a nucleic acid of the invention, or to detect the presence of nucleic acids according to the invention. Generally, oligonucleotides are prepared synthetically, for example, on a nucleic acid synthesizer. Accordingly, oligonucleotides can be prepared with non-naturally occurring phosphoester analog bonds, such as thioester bonds, etc.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions can include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter.

Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths can have identical promoter activity. A promoter is generally bounded at its 3° terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression can also refer to translation of mRNA into a polypeptide.

Polynucleotides of the Invention

The present invention provides for the use of cbh2 polynucleotide sequences from *Cochliobolus heterostrophus, Gibberella zeae, Irpex lacteus, Volvariella volvacea*, and *Piromyces* sp.

The *Cochliobolus heterostrophus* C4 cel7, *Gibberella zeae* K59 cel6, *Irpex lacteus* MC-2 cex3, *Volvariella volvacea* cbhII-I, and *Piromyces* sp. E2 cel6A nucleic acid sequences are available in GenBank, and are shown in Table 1 below.

TABLE 1

Polynucleotide sequences encoding Cbh2s.

*Cochliobolus heterostrophus* C4 cel7 (GenBank accession: AY116307)
cttcttggttctcaaagatgctctccaacgtctttcttaccgctgccctcgcagccggcctggctcaggccctgccccaggccacgcctaccc
caaccgctgcgccctctggcaacccttcgcgggcaagaacttctacgccaacccatactactcgtctgaagtccacaccctggccatgcc
ctcgcttccagcctcgctgaagcctgctgctaccgccgtggccaaggtcggatcattcgtgtggatggacaccatggccaaggttcctctcat
ggacacctacctcgcagacatcaaggccaagaacgctgctggcgcaaacctcatgggtactttgtcgtctacgaccttcccgaccgtgact
gcgccgctctggcctccaacggtgaactcaagattgacgagggtggtgtcgagaagtacaagacccagtacattgacaagattgccgccat
catcaagaagtaccccgacgtcaagatcaaccttgccattgagcccgattcccttgccaacatggtcaccaacatgggtgtgcagaagtgct
cgcgcgccgccccatactacaaggagctcactgcctacgccctcaagacgctcaacttcaacaacgtcgacatgtacatggacggttggcc
acgccggttggctcggctgggacgccaacattggccctaccgcaaagcttttcgcagaggtctacaaggctgctggctctcccgtggcgt
ccgtggtatcgtcaccaacgtcagcaactacaacgctctccgcgttcctcctgccatccatcaccaaggaaacaagaactgcgacgag
gagcgctacatcaacgccttggctcctcttctcaagaacgagggtttccctgctcacttcatcgtcgaccagggccgctccggaaaggtgcct
actaaccagcaggagtggggtgactggtgcaacgtctcaggtgctggattcggtaccgtcccaccaacactggcaatgccctcattg
atgccatcgtctgggtcaagcccggtggcgagtctgacggtacctctgacaccagcgctgcccgctacgatgcccactgcggcaggaaca
gcgctttcaagcccgctcctgaggctggaacctggttccaggcttacttcgagatgcttctcaagaacgctaaccctgctcttgcttaagtgtct
ggttcttttgaataagcttgggtagattgttagaagggaaaattagtctgcgagtggtcttcaccgcagattctggtggattgtaaatatggctt
ggaactagaataggcaacgtttgatgttgcagttcgtgtaaatattatacctttggagctaaaaaaaaaaaaaaaaaa (SEQ ID NO: 1)

*Gibberella zeae* K59 cel6 (GenBank Accession AY302753)
atgacggcctacaagcttttcctggctgctgcttttgcagccactgctctcgcagctcctgttgaagagcgtcagtcttgcagcaacggagtct
ggtgagtgtttgcagccatctttttaaagaattaattactcacataccccataggtctcaatgtggtggtcagaactggagcggtactccttgctgc
accagtggaaacaagtgtgtcaaggtcaacgacttctactcccaatgccagcctggatccgcagacccttctcccacgagcaccattgtcag
tgccacaaccaccaaggctactaccactggtagtggaggctctgcctcgcctcctcctgttgccaccaacaatcccttctctggcgttgat
ctgtgggccaacaactactaccgctccgaggtcagcactctcgctatcccaagctgagcggtgccatggccacgctgctgccaaggtcg
ccgatgttccttcttccagtggatgtgagttacgagtcccttggatatataccctttactaaccacgatagggacacttatgaccacatctcctt
catggaggactctcttgccgatatccgcaaggccaacaaggctggtggcaactacgctggtcagttcgtcgtctacgatcttcccgaccgtg
actgtgctgctgctgcctccaacggagagtactcccttgacaaggatggcaagaacaagtacaaggcctacattgcagatcaagggatcctt
caggactactctgacacccgcatcattctcgttatcggttagtccacctgattgactccgacttagttcctactaacagccatttagagcctgatt
ctcttgctaacatggtcaccaacatgaacgtcccccaagtgcgcaacgctgctagcgcttacaaggagctcaccattcacgccctcaaggag
ctcaaccttcccaacgtctccatgtacatcgatgcaggtcacggtggctggctgggatggcccgccaaccttcctcctgccgcccagctcta
cggtcagctctacaaggatgccggcaagccatctcgcctccgaggtctcgtcaccaacgtctccaactacaacgcctggaagctgtcctcc
aagcccgactacactgagagcaaccccaactacgacgagcagaagtacatccacgctctatctcctcttctggagcaggagggctggccc
ggtgccaagttcatcgtcgaccagggccgatctgtaagcagcccactggccacgaaaggcttggggtgactggtgcaacgctcccggaact
ggattcggtctccgaccctctgccaacactggcgatgcctcgtcgacgctttcgtctgggtcaagcctggtggtgagtctgatggtacctct
gatacctctgctgctcgctacgactaccactgcggtattgacggcgctgtcaagtaagttttataatacaaatcctcaagttaaccctcatactaa
ccccgataactaggcccgctcctgaggctggaacctggttccaggcttactttgagcagcttctcaagaacgccaaccccttcctgtaa
(SEQ ID NO: 2)

*Irpex lacteus* MC-2 cex3 (GenBank Accession AB370872)
ccgcaccccagcatagcaacagcttttcgtcggcaagatattaagcacggtcatggagttttcaacgacttaaccgagcttgtaccgaagtg
gacggcagttcgctgaacgttcgggtgtgcttttacaacccgtcgttgaaaataatgtgtaggtatggccgtagcctcatgacccactcata
acgtccgtcgttcagcaactgaccctcccccgacgtctatccgctaacaatgctcgggtctacgccggaattatggtattcttccactggtggg

TABLE 1-continued

Polynucleotide sequences encoding Cbh2s.

```
cctgaacgatgcaaaacggtgcttctgatgagcccacctctgtattatttccggtatataagaagtggtatcgtcggctagggttctacaggatc
cacatcccactgagacgaatccactgcaagtgcaatgaagtccgctgcttctctcgctgctctcgccgccatcctcccagcctatgtcgctgg
ccaagcccagacttgggcacagtgcggtggtatcggcttcagtacgttactaccttttctccttctactggtctgttacttactgaacttgcctatca
tagctggtcctaccacttgcgttgccggctccgtctgcacgaagcagaatgattactactctcagtgcatgtaagtacgaatccacccttttgca
agaactactgacttatgatggggtatagtcctggatctgctactactcccacatctgcacctacatctgcacccacctcccagccttcgcagcc
atcttccacctcctctgctccttccggtccttcctctaccccacgccctctgccaacaacccatggactggctaccaggtatgcgggcgatcc
attgtaactctaaaaatctctttctgacctgacctgggcatagatctacttgagccttactacgctaacgaggttgctgccgccgccaaggcaa
tcacggaccccacctcgccgccaaggctgccagcgttgctaacatcccgaacttcacttggttgggtgagtgtgacattgacaagagaag
gaaacgacttcctaattacccgcatagactccgtctccaagatcgctgatcttaagacatacctcgctgacgcaagtgcactgggcaagtcca
gcggtcagaagcaactcctccagattgtcgtatacgatcttcccgaccgtgattgcgctgctaaggcctccaatggagagttcagcattgctg
acaacggcctggccaactaccagaactacatcgaccagatcgttgcgctggtcgtcaagcgtaagtctcgacgaggcagttcacttcgctttgcat
actgagcctgttcgccacagaattccctgacgttcgggtcgtggctgtcattgagcccgactctcttgccaacttggtcaccaacttgaacgtg
cagaagtgcgctaacgccaagagcacctacctcactgccgtcaactacgctttgaagcagctctcctcagttggcgtgtaccagtacatgga
cgcaggtcacgccggatggctcggttggcccgccaacttgaccccgccgctcagctgttcgctcaagtttactctgatgccggaaagtcg
ccattcatcaagggtcttgctaccagtacgttttcatttcgttttgttcgatcactcaagactgacccgcttgaatcgcaaagacgtcgccaacta
caacgccttgagcgcggcctcacccgatcccatcacccagggtgacccaactacgatgaaatccactacatcaacgtaagcccgtttaac
cgtacaatgcgatgtgtactaatcaaaccaaatcccgcaggctctcgctccggctctccagtccgctggcttccctgctaccttcatcgtcgat
caaggccgttccggtcagcagaaccaccgacaacagtggggtgactggtgcaacatcaagggtgctgggttcggtacccgcccgaccac
caacactggttcttcgctcatcgactccatcgtttgggtgaagcccggaggtgaatccgacgtacctcgaactcgtcttcgcccccgtttcgac
tccacttgctctttggtaagttcggccttctgttcgtcaaactgagtgtgatgctaactcatcgtgcttgcagtcggatgctactcagcccgctcct
gaggccggtacatggttccaggcttacttcgagactctcgtctccaaggccaacccaccgctctaagcgtatcgtacctgctttcaaaatgtg
gctgaacggcatagaacagctgctcttggggttctcttcacttgatcgcgattttttatatacctgtattttatgtagcataaaaagtaaaacagccg
cagaaatgcattcgcttttcacttgtaccgcgtcttgttcttgtgccaaatgctctcgcgtcctaccgagttcatctttcgatatcagtgagcggcc
agcatcgaaacgaccactgcgttagtttgtctggcgacatctgcatgcaagcta (SEQ ID NO: 3)
```

*Volvariella volvacea* cbhII-I (GenBank Accession AY559104)
```
tgattgcaagccacatatcccagagatgtccaggttttctgctcttactgctctccttttatcttttgccactactggctattgctcagtccccgttgta
tgggcaatgtggtggcaacggctggactggcccaaagacctgtgtatcaggtgcaacttgtacagtgatcaatgactggtattggcaatgcct
gccaggaaatggccaacttcttcttcaccaacttccacacctaccaccaccacaactacaggggacctcaaccaaccgtaccagcagca
gggaatccttatactggatacgagatttacttgagtccttattacgctgctgaggctcaagctgcggctgcccaaatttctgatgccacgcaga
aggccaaagccctgaaggtcgcacaaatccccacattcacctggtttgatgttattgcaaagacctccacactcggtgattatttggccgaag
cgagcgcacttgggaaatcctctggaaagaaatacctcgttcaaatcgttgtatatgacttgccagatcgggattgcgctgctctggcttcgaa
tggagagtttagcatcgcaaacaatgggctcaacaactacaagggctacatcgatcaattggttgctcagatcaagaaataccctgatgtccg
agtcgtggctgtcgttattgaacccgactccttggccaatctcgttaccaatctcaatgttagcaagtgtgccaatgcacaaacagcctacaaggct
ggtgtcacgtacgctctccagcagctcaactctgttggcgtctatatgtacctcgatgctggacatgcggggttggctcggatggcctgccaact
tgaatcccgctgcgcaactgttctctcaattgtacagagatgctggaagtccccaatatgtccgtggcctagctaccaatgttgccaactacaa
cgcactctctgccagcagccccgacccagtcacacaaggcaatcccaactatgacgaacttcattacatcaacgcactcgcgccagctctc
caatccggtggcttccctgcccacttcattgtcgaccaaggccgatcaggagttcagaacatcagacaacaatggggcgactggtgcaacg
tcaagggtgcaggctttggccagcgtccaactcttagcacaggttcatcccttatcgacgccattgtctggattaaacccggaggcgaatgcg
acggtacaaccaacacatcgtcacctcgctatgattctcactgtggtctttctgatgctacacccaatgccccagaagctggccaatggttcca
ggcttacttcgagacctagtccgtaacgccagcccacctctttgagtgtgcagtgtagataccagatatacaaggccccgagtgtgatacaa
cagaataaataatcccttttgctcctctcaaaaaaaaaaaaaaaaaaaaaa (SEQ ID NO: 4)
```

*Piromyces* sp. E2 cel6A (GenBank Accession AY082395)
```
aaatcttaattataattaataatatcattttttcatttattatatttatactttgtttcatgaaataataataaacaacatttttcccaatagttttaaaat
cattttttacttttctcaaatttatcgaacaattaaaaactataaaaggagcaattttttcattttaattattttctttcattaattaaaaaattattttct
ctggaagaaaataaatataatagaaaaaataaaaagaaaaggaaattacaaaaaacaaaaatttaaataatatattgatttatatattaattaaaaat
aatatattttttaaatttattatcaacaaaaaaaaaatttttaatcaaaaaatgaaggcttctattgctttaactgctattgccgctcttgctgctaac
gcttctgctgcttgtttctctgaaagacttggttatccatgttgcagaggtaatgaagttttttacaccgataatgatggtgattggggtgttgaaaatg
gtaactggtgtggtattggtggtgcttctgctactacctgctggtctcaagctttaggttacccatgttgtacttctacttccgatgttgcctatgttga
tggtgatggcaattggggtgttgaaaatggtaattggtgtggtattattgctggtggtaattcaagcaacaacaacagtggtagtaccattaatgttg
gtgatgttaccattggtaatcaatacactcacactggtaatccattcgctggtcacaaaattcttcattaatccatactacactgctgaagtcgatgg
tgccatcgctcaaatttctaacgctctcttctagagctaaggctgaaaaaatgaaaaaattctctaatgctatctggttagatactattaagaatatg
aatgaatggttagaaaagaatcttaaatacgctcttgctgaacaaaatgaaactggtaagaccgttttaaccgttttcgttgtttacgatttaccag
gtcgtgattgtcatgctcttgcttccaatggtgaacttcttgccaacgacagtgattgggctcgttaccaatcggaatacattgatgtcattgaag
aaaaattaaagacttacaagagtcaaccagttgttcttgttgttgaaccagattctcttgctaacatggttactaatcttgattctactccagcttgtc
gtgattctgaaaagtattacatggatggtcatgcttacttaattaaaaaagcttggtgttcttccacatgttgctatgtaccttgatattggtcatgctttt
ctggttaggatgggatgataaccgtttaaaggctggtaaggtttactccaagtttattattgtccaaggtaatcggtgtccagttaatgttcgtttct
aacgttgctaactacactccatgggaagatccaactctttctcgtggtccagacactgaatggataatccatgatccagatgaaagagatacattg
aagccatgtacaaggacttcaagtctgctggtattaaatccgttttacttcattgatgatacttctcgtaatggtcacaaaaccgaccgtactcatc
caggagaatggtgtaaccaaaccggagttggtattggtgctcgtccacaagccaatccaatctctggtatggactaccttgatgctttctactg
ggttaaaccactcggtgaatccgatggttactccgatactacagccgttcgttatgatggttattgtggtcatgctactgccatgaaaccagcac
cagaagccggtcaatggttccaaaaagcactttgaacaaggtcttgaaaatgctaatccaccactctaatcatattaacattaaataatatacatta
tatacatatagaaagaaacatgaatattantattaacataatcatactnttaaataaattatt (SEQ ID NO: 5)
```

The present invention also provides for the use of an isolated polynucleotide comprising a nucleic acid at least about 70%, 75%, or 80% identical, at least about 90% to about 95% identical, or at least about 96%, 97%, 98%, 99% or 100% identical to any of SEQ ID NOs:1-5, or fragments, variants, or derivatives thereof.

In certain aspects, the present invention relates to a polynucleotide comprising a nucleic acid encoding a functional and/or structural domain of a *Cochliobolus heterostrophus, Gibberella zeae, Irpex lacteus, Volvariella volvacea,* or *Piromyces* sp. Cbh2. The present invention also encompasses an isolated polynucleotide comprising a nucleic acid that is 70%, 75%, or 80% identical, at least about 90% to about 95% identical, or at least about 96%, 97%, 98%, 99% or 100% identical to a nucleic acid encoding a *Cochliobolus heterostrophus, Gibberella zeae, Irpex* lacteus, Volvariella volvacea, or *Piromyces* sp. Cbh2 domain.

In some embodiments, the domain of the *Cochliobolus heterostrophus, Gibberella zeae, Irpex lacteus, Volvariella volvacea,* or *Piromyces* sp. Cbh2 is, for example, a GH6 family domain, a CBM domain or a signal peptide. In some specific embodiments, the domain is selected from the domains shown in Table 2 below.

TABLE 2

Exemplary Domains of Cbh2 Proteins.

| Organism & Gene | Domain (amino acids) Sequence |
|---|---|
| *Cochliobolus heterostrophus* C4 cel7 | GH Family 6 Domain (aa 42-354)<br>ANPYYSSEVHTLAMPSLPASLKPAATAVAKVGSFVWMDTMAKVPLMD<br>TYLADIKAKNAAGANLMGTFVVYDLPDRDCAALASNGELKIDEGGVEK<br>YKTQYIDKIAAIIKKYPDVKINLAIEPDSLANMVTNMGVQKCSRAAPYY<br>KELTAYALKTLNFNNVDMYMDGGHAGWLGWDANIGPTAKLFAEVYK<br>AAGSPRGVRGIVTNVSNYNALRVSSCPSITQGNKNCDEERYINALAPLLK<br>NEGFPAHFIVDQGRSGKVPTNQQEWGDWCNVSGAGFGTRPTTNTGNAL<br>IDAIVWVKPGGESDGTSDTSAARYD (SEQ ID NO: 22)<br>Signal Peptide (aa 1-18)<br>MLSNVFLTAALAAGLAQA (SEQ ID NO: 23)<br>CBM Domain<br>N/A |
| *Gibberella zeae* K59 cel6 | GH Family 6 Domain (aa 111-423)<br>ANNYYRSEVSTLAIPKLSGAMATAAAKVADVPSFQWMDTYDHISFMED<br>SLADIRKANKAGGNYAGQFVVYDLPDRDCAAAASNGEYSLDKDGKNK<br>YKAYIADQGILQDYSDTRIILVIEPDSLANMVTNMNVPKCANAASAYKE<br>LTIHALKELNLPNVSMYIDAGHGGWLGWPANLPPAAQLYGQLYKDAGK<br>PSRLRGLVTNVSNYNAWKLSSKPDYTESNPNYDEQKYIHALSPLLEQEG<br>WPGAKFIVDQGRSGKQPTGQKAWGDWCNAPGTGFGLRPSANTGDALV<br>DAFVWVKPGGESDGTSDTSAARYDY (SEQ ID NO: 24)<br>Signal Peptide (aa 1-18)<br>MTAYKLFLAAAFAATALA (SEQ ID NO: 25)<br>CBM Domain (aa 31-59)<br>VWSQCGGQNWSGTPCCTSGNKCVKVNDFY (SEQ ID NO: 26) |
| *Irpex lacteus* MC-2 cex3 | GH Family 6 Domain (aa 107-419)<br>VDLWANNYYRSEVSTLAIPKLSGAMATAAAKVADVPSFQWMDTYDHIS<br>FMEDSLADIRKANKAGGNYAGQFVVYDLPDRDCAAAASNGEYSLDKD<br>GKNKYKAYIADQGILQDYSDTRIILVIEPDSLANMVTNMNVPKCANAAS<br>AYKELTIHALKELNLPNVSMYIDAGHGGWLGWPANLPPAAQLYGQLYK<br>DAGKPSRLRGLVTNVSNYNAWKLSSKPDYTESNPNYDEQKYIHALSPLL<br>EQEGWPGAKFIVDQGRSGKQPTGQKAWGDWCNAPGTGFGLRPSANTG<br>DALVDAFVWVKPGGESDGTSDTSAA (SEQ ID NO: 27)<br>Signal Peptide Domain (aa 1-20)<br>MTAYKLFLAAAFAATALAAP (SEQ ID NO: 28)<br>CBM Domain (aa 25-52)<br>QSCSNGVWSQCGGQNWSGTPCCTSGNKC (SEQ ID NO: 29) |
| *Volvariella volvacea* cbhII-I | GH Family 6 Domain (aa 120-409)<br>KALKVAQIPTFTWFDVIAKTSTLGDYLAEASALGKSSGKKYLVQIVVYD<br>LPDRDCAALASNGEFSIANNGLNNYKGYIDQLVAQIKKYPDVRVVAVIE<br>PDSLANLVTNLNVSKCANAQTAYKAGVTYALQQLNSVGVYMYLDAGH<br>AGWLGWPANLNPAAQLFSQLYRDAGSPQYVRGLATNVANYNALSASSP<br>DPVTQGNPNYDELHYINALAPALQSGGFPAHFIVDQGRSGVQNIRQQWG<br>DWCNVKGAGFGQRPTLSTGSSLIDAIVWIKPGGECDGTTNTSSPRYDS<br>(SEQ ID NO: 30)<br>Signal Peptide Domain (aa 1-20)<br>MSRFSALTALLLSLPLLAIA (SEQ ID NO: 31)<br>CBM Domain (aa 25-52)<br>YGQCGGNGWTGPKTCVSGATCTVINDWY (SEQ ID NO: 32) |
| *Piromyces* sp. E2 cel6A | GH Family 6 Domain (aa 138-457)<br>INPYYTAEVDGAIAQISNASLRAKAEKMKEFSNAIWLDTIKNMNEWLEK<br>NLKYALAEQNETGKTVLTVFVVYDLPGRDCHALASNGELLANDSDWA<br>RYQSEYIDVIEEKLKTYKSQPVVLVVEPDSLANMVTNLDSTPACRDSEK<br>YYMDGHAYLIKKLGVLPHVAMYLDIGHAFWLGWDDNRLKAGKVYSK<br>VIQSGAPGNVRGFASNVANYTPWEDPTLSRGPDTEWNPCPDEKRYIEAM<br>YKDFKSAGIKSVYFIDDTSRNGHKTDRTHPGEWCNQTGVGIGARPQANP<br>ISGMDYLDAFYWVKPLGESDGYSDTTAVRYD (SEQ ID NO: 33)<br>Signal Peptide Domain (aa 1-19)<br>MKASIALTAIAALAANASA (SEQ ID NO: 34)<br>CBM Domain (aa 21-55)<br>CFSERLGYPCCRGNEVFYTDNDGDWGVENGNWCGI (SEQ ID NO: 35)<br>CBM Domain (aa 62-98)<br>TCWSQALGYPCCTSTSDVAYVDGDGNWGVENGNWCGI (SEQ ID NO: 36) |

The present invention also encompasses variants of the cbh2 genes, as described above. Variants can contain alterations in the coding regions, non-coding regions, or both. Examples are polynucleotide variants containing alterations which produce silent substitutions, additions, or deletions, but do not alter the properties or activities of the encoded polypeptide. In certain embodiments, nucleotide variants are produced by silent substitutions due to the degeneracy of the genetic code. In further embodiments, *Cochliobolus heterostrophus, Gibberella zeae, Irpex lacteus, Volvariella volvacea*, and *Piromyces* sp. cbh2 polynucleotide variants can be produced for a variety of reasons, e.g., to optimize codon expression for a particular host (e.g., change codons in the cbh2 mRNA to those preferred by a host such as the yeast *Saccharomyces cerevisiae*). Codon-optimized polynucleotides of the present invention are discussed further below.

The present invention also encompasses an isolated polynucleotide comprising a nucleic acid that is at least about 70%, 75%, or 80% identical, at least about 90% to about 95% identical, or at least about 96%, 97%, 98%, 99% or 100% identical to a nucleic acid encoding a fusion protein, wherein the nucleic acid comprises (1) a first polynucleotide, where the first polynucleotide encodes for a *Cochliobolus heterostrophus, Gibberella zeae, Irpex lacteus, Volvariella volvacea*, or *Piromyces* sp. Cbh2, or domain, fragment, variant, or derivative thereof; and (2) a second polynucleotide.

In certain embodiments, the second polynucleotide encodes for a CBM domain, for example, the CBM domain of *T. reesei* Cbh1 or *T. reesei* Cbh2. The second polynucleotide can also encode for the CBM domain of *Gibberella zeae, Irpex lacteus, Volvariella volvacea*, or *Piromyces* sp. Cbh2. For example, the first polynucleotide can encode for *Cochliobolus heterostrophus* Cbh2 or a fragment thereof, and the second polynucleotide can encode for the CBM domain of *T. reesei* Cbh1 or *Gibberella zeae* Cbh2. In addition, the first polynucleotide can encode for *Gibberella zeae* Cbh2 or a fragment thereof, and the second polynucleotide can encode for the CBM of *Gibberella zeae* Cbh2.

In further embodiments of the fusion polynucleotide, the first and second polynucleotides are in the same orientation, or the second polynucleotide is in the reverse orientation of the first polynucleotide. In additional embodiments, the first polynucleotide is either 5' or 3' to the second polynucleotide. In certain other embodiments, the first polynucleotide and/or the second polynucleotide are encoded by codon-optimized polynucleotides, for example, polynucleotides codon-optimized for expression in *S. cerevisiae*. In particular embodiments of the nucleic acid encoding a fusion protein, the first polynucleotide is a codon-optimized *Cochliobolus heterostrophus, Gibberella zeae, Irpex lacteus, Volvariella volvacea*, or *Piromyces* sp. cbh2, and the second polynucleotide encodes for a codon-optimized CBM from *T. reesei* Cbh1 or Cbh2.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 1-5, using information from the sequences disclosed herein or the clones deposited with the ATCC. For example, allelic variants and/or species homologs can be isolated and identified by making suitable probes or primers from the sequences provided herein and screening a suitable nucleic acid source for allelic variants and/or the desired homologue.

Polynucleotides comprising sequences that are at least 80%, 85%, 90%, 95%, 96%, 97%, 98%, or 99% identical to the entire sequence of any of SEQ ID NOs:1-5 or any fragment or domain therein can be used according to the methods described herein. Some embodiments of the invention encompass a nucleic acid molecule comprising at least 10, 20, 30, 35, 40, 50, 60, 70, 80, 90, 100, 200, 300, 400, 500, 600, 700, or 800 consecutive nucleotides or more of any of SEQ ID NOs:1-5, or domains, fragments, variants, or derivatives thereof.

The polynucleotide of the present invention can be in the form of RNA or in the form of DNA, which DNA includes cDNA, genomic DNA, and synthetic DNA. The DNA can be double stranded or single-stranded, and if single stranded can be the coding strand or non-coding (anti-sense) strand. The coding sequence which encodes the mature polypeptide can be identical to the coding sequence encoding SEQ ID NOs:11-15 or can be a different coding sequence which coding sequence, as a result of the redundancy or degeneracy of the genetic code, encodes the same mature polypeptide as the DNA of any one of SEQ ID NOs:1-5.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NOs:11-15.

The polynucleotide encoding for the mature polypeptide of SEQ ID NOs:11-15 can include: only the coding sequence for the mature polypeptide; the coding sequence of any domain of the mature polypeptide; or the coding sequence for the mature polypeptide (or domain-encoding sequence) together with non-coding sequence, such as introns or non-coding sequences 5° and/or 3' of the coding sequence for the mature polypeptide.

Thus, the term "polynucleotide encoding a polypeptide" encompasses a polynucleotide which includes only sequences encoding for the polypeptide as well as a polynucleotide which includes additional coding and/or non-coding sequences.

In further aspects of the invention, nucleic acid molecules having sequences with at least about 90%, 95%, 96%, 97%, 98% or 99% identity to the nucleic acid sequences disclosed herein, encode a polypeptide having Cbh2 functional activity. The phrase "a polypeptide having Cbh2 functional activity" is intended to refer to a polypeptide exhibiting activity similar, but not necessarily identical, to a functional activity of the Cbh2 polypeptides of the present invention, as measured, for example, in a particular biological assay. For example, a Cbh2 functional activity can routinely be measured by determining the ability of a Cbh2 polypeptide to hydrolyze cellulose, i.e. by measuring the level of Cbh2 activity.

Of course, due to the degeneracy of the genetic code, one of ordinary skill in the art will immediately recognize that a large portion of the nucleic acid molecules having a sequence at least about 90%, 95%, 96%, 97%, 98%, or 99% identical to the nucleic acid sequence of any of SEQ ID NOs:1-5, or fragments thereof, will encode polypeptides "having Cbh2 functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having Cbh2 functional activity.

Fragments of the full length gene of the present invention can be used as a hybridization probe for a cDNA library to isolate the full length cDNA and to isolate other cDNAs which have a high sequence similarity to the cbh1 genes of the present invention, or a gene encoding for a protein with similar biological activity. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

In certain embodiments, a hybridization probe can have at least 30 bases and can contain, for example, 50 or more bases. The probe can also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of bacterial or fungal cDNA, genomic DNA or mRNA to determine to which members of the library the probe hybridizes.

The present invention further relates to polynucleotides which hybridize to the hereinabove-described sequences if there is at least about 70%, at least about 90%, or at least about 95% identity between the sequences. The present invention particularly relates to polynucleotides which hybridize under stringent conditions to the hereinabove-described polynucleotides. As herein used, the team "stringent conditions" means hybridization will occur only if there is at least about 95% or at least about 97% identity between the sequences. In certain aspects of the invention, the polynucleotides which hybridize to the hereinabove described polynucleotides encode polypeptides which either retain substantially the same biological function or activity as the mature polypeptide encoded by the DNAs of any of SEQ ID NOs:1-5.

Alternatively, polynucleotides which hybridize to the hereinabove-described sequences can have at least 20 bases, at least 30 bases, or at least 50 bases which hybridize to a polynucleotide of the present invention and which has an identity thereto, as hereinabove described, and which may or may not retain activity. For example, such polynucleotides can be employed as probes for the polynucleotide of any of SEQ ID NOs: 1-5, for example, for recovery of the polynucleotide or as a diagnostic probe or as a PCR primer.

Hybridization methods are well defined and have been described above. Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

For example, genes encoding similar proteins or polypeptides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (see, e.g., Maniatis, 1989). Moreover, the entire sequences can be used directly to synthesize DNA probes by methods known to the skilled artisan such as random primers DNA labeling, nick translation, or end-labeling techniques, or RNA probes using available in vitro transcription systems.

In certain aspects of the invention, polynucleotides which hybridize to the hereinabove-described sequences having at least 20 bases, at least 30 bases, or at least 50 bases which hybridize to a polynucleotide of the present invention can be employed as PCR primers. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. Generally two short segments of the instant sequences can be used in polymerase chain reaction (PCR) protocols to amplify longer nucleic acid fragments encoding homologous genes from DNA or RNA. The polymerase chain reaction can also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence can be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

In addition, specific primers can be designed and used to amplify a part of or the full-length of the instant sequences. The resulting amplification products can be labeled directly during amplification reactions or labeled after amplification reactions, and used as probes to isolate full length DNA fragments under conditions of appropriate stringency.

Therefore, the nucleic acid sequences and fragments thereof of the present invention can be used to isolate genes encoding homologous proteins from the same or other fungal species or bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, Mullis et al., U.S. Pat. No. 4,683,202; ligase chain reaction (LCR) (Tabor, S. et al., *Proc. Acad. Sci. USA* 82, 1074, (1985)); or strand displacement amplification (SDA), (Walker, et al., *Proc. Natl. Acad. Sci. USA* 89, 392, (1992)).

The polynucleotides of the present invention also comprise nucleic acids encoding a *Cochliobolus heterostrophus, Gibberella zeae, Irpex lacteus, Volvariella volvacea* or *Piromyces* sp. Cbh2, or domain, fragment, variant, or derivative thereof, fused to a polynucleotide encoding a marker sequence which allows for selection and/or detection of the presence of the polynucleotide in an organism. Expression of the marker can be independent from expression of the Cbh2 polypeptide. The marker sequence can be a yeast selectable marker such as URA3, HISS, LEU2, TRP1, LYS2, ADE2 or SMR1. See, e.g., Casey, G. P. et al., *J. Inst. Brew.* 94:93-97 (1988).

Codon Optimization

As used herein the term "codon-optimized coding region" means a nucleic acid coding region that has been adapted for expression in the cells of a given organism by replacing one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The Codon Adaptation Index is described in more detail in Sharp and Li, *Nucleic Acids Research* 15: 1281-1295 (1987)), which is incorporated by reference herein in its entirety.

The CAI of codon-optimized sequences of the present invention corresponds to from about 0.6 to about 1.0, from about 0.7 to about 1.0, from about 0.8 to about 1.0, from about 0.9 to about 1.0, from about 9.5 to about 1.0, or about 1.0. A codon-optimized sequence can be further modified for expression in a particular organism, depending on that organism's biological constraints. For example, large runs of "As" or "Ts" (e.g., runs greater than 4, 5, 6, 7, 8, 9, or 10 consecutive bases) can be removed from the sequences if these are known to effect transcription negatively. Furthermore, specific restriction enzyme sites can be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 3. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 3

The Standard Genetic Code.

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter (Y) | TGA Ter |
| | TTG Leu (L) | TCG Ser (S) | TAG Ter (Y) | TGG Trp (W) |

TABLE 3-continued

The Standard Genetic Code.

| | T | C | A | G |
|---|---|---|---|---|
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables and codon-optimizing programs are readily available, for example, at the web site of the University of Maryland, Baltimore County (visited Sep. 4, 2009) or at the website of the Kazusa DNA Research Institute (visited Sep. 4, 2009), and these tables can be adapted in a number of ways. See Nakamura, Y., et al. "Codon usage tabulated from the international DNA sequence databases: status for the year 2000," Nucl. Acids Res. 28:292 (2000). Codon usage tables for yeast, calculated from GenBank Release 128.0 [15 Feb. 2002], are reproduced below as Table 4. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 4

Codon Usage Table for *Saccharomyces cerevisiae* Genes.

| Amino Acid | Codon | Number | Frequency per hundred |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |

TABLE 4-continued

Codon Usage Table for *Saccharomyces cerevisiae* Genes.

| Amino Acid | Codon | Number | Frequency per hundred |
|---|---|---|---|
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 4 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 4 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence will can vary significantly using this method; however, the sequence always encodes the same polypeptide.

Codon-optimized sequences of the present invention include those as set forth in Table 5 below.

TABLE 5

Cellobiohydrolase 2 (cbh2) polynucleotice sequences codon-optimized for expression in *S. cerevisiae*.

*Cochliobolus heterostrophus* C4 cel7

```
ttaattaaaatgttgtctaacgtttttttgactgctgctttggctgctggtttggctcaagcttttgccacaagctactccaactccaactgctgctcca
tctggtaatccatttgctggtaagaattttttacgctaacccatattattatcagaagttcatactttggctatgccatctttgccagcttcattgaaac
cagctgctactgctgttgctaaagttggttcttttgtttggatggatactatggctaaagttccattgatggatacttacttggctgatattaaagcta
aaaatgctgctggtgctaatttgatgggtactttcgttgtttatgatttgccagatagagattgtgctgctttagcttctaatggtgaattgaaaattg
atgaaggtggtgttgaaaaatacaagacacaatacattgataagattgctgctattatcaaaaagtacccagatgttaagattaatttggctattg
aaccagattctttggctaatatggttactaatatgggtgttcaaaaatgttctagagctgctccatattacaaagaattgactgcttatgctttgaaa
```

TABLE 5-continued

Cellobiohydrolase 2 (cbh2) polynucleotice sequences codon-optimized for expression in *S. cerevisiae*.

actttgaacttcaacaacgttgacatgtatatggatggtggtcatgctggtggttggttgggttgggatgctaatattggtccaactgctaaattgtttg
ctgaagtttacaaagctgctggttctccaagaggtgttagaggtattgttacaaacgtttctaattacaacgctttgagagtttcttcttgtccatcta
ttactcaaggtaacaagaattgtgatgaagaaagatacattaatgctttggctccattgttgaaaaatgaaggttttccagctcattttattgttgat
caaggtagatcaggtaaagttccaactaatcaacaagaatgggtgattggtgtaatgtttctggtgctggttttggtactagaccaactactaa
tactggtaatgctttgattgatgctattgtttgggttaaaccaggtggtgaatctgatggtacttctgatacttctgctgcaagatatgatgctcattg
tggtagaaattctgcttttaaaccagctccagaagctggtacttggtttcaagcttactttgaaatgttgttgaagaatgctaatccagctttggcat
tataaggcgcgcc (SEQ ID NO: 6)

*Gibberella zeae* K59 cel6
ttaattaaaatgactgcttacaaatttgttttttggctgctgcttttgctgctactgctttggctgctccagttgaagaaagacaatcttgttctaatggtg
tttggtcacaatgtggtggtcaaaattggtctggtactccatgttgtacatctggtaacaagtgtgttaaggttaatgatttctactctcaatgtcaa
ccaggttctgctgatccatctccaacttctactattgtttctgctactactactaaagctactactacaggttctggtggttctgttacttctccacca
ccagttgctacaaacaatccatttttctggtgttgatttgtgggcaaacaattattacagatcagaagtttctactttggctattccaaaattgtctggt
gctatggctactgctgctgcaaaagttgctgatgttccatcttttcaatggatggatactttacgatcatatttctttcatggaagattcttttggctgat
attagaaaagcaaacaaagcaggtggtaattatgctggtcaattcgttgtttatgatttgccagatagagattgtgctgctgctgcttctaatggt
gaatactctttggataaagatggtaaaaacaagtacaaagcttatattgctgatcaaggtattttgcaagattactctgatactagaatcattttggt
tattgaaccagattcttttagctaacatggttactaatatgaatgttccaaaatgtgctaatgctgcttctgcttacaaagaattgactattcatgcttt
gaaagaattgaatttgccaaacgtttcaatgtatattgatggtggtcatggtcatggttggtttgggttggccagctaatttgccacctgctgctcaattg
tatggtcaattgtacaaagatgctggtaaaccatctagattgagaggtttggttactaatgtttctaattacaacgcttggaaattatcttctaagcc
agattatactgaatctaacccaaattacgatgaacaaaagtacattcatgctttatctccattgttggaacaagaaggttggccaggcgctaagt
tcattgttgatcaaggtagatcaggtaaacaaccaactggtcaaaaagcttggggtgattggtgtaatgctccaggtactggttttggtttaaga
ccatctgctaatactggtgctgcttggttgatgcttttgtttgggttaaaccaggtggtgaatctgatggtacttctgatacttctgctgcaagatat
gattatcattgtggtattgatggtgctgttaaaccagctccagaagctggtacttggtttcaagcttactttgaacaattgttgaagaatgctaatcc
atcttcttgttataaggcgcgcc (SEQ ID NO: 7)

*Irpex lacteus* MC-2 cex3
ttaattaaaatgaagtctgctgcttttttggctgctttagctgctattttgccagcttacgttgctggtcaagctcaaacttgggctcaatgtggtggt
attggttttactggtccaactacttgtgttgctggttctgtttgtactaaacaaaacgattactactctcaatgtattccaggttctgctactactccaa
cttctgctccaacatctgcaccaacttctcaaccatcacaaccatatctacttcatctgctccatctggtccatcttctacaccaactccatctgct
aacaatccatggactggttatcaaatttacttgtctccatactatgctaatgaagttgctgcagctgctaaagctattactgatccaacttggctg
ctaaagcagctcctgttgctaatattccaaatttcacttggttggattctgtttctaaaattgctgatttgaaaactttatttggctgatgcttctgcttgt
tggtaaatcttctggtcaaaagcaattgttgcaaattgttgtttatgatttgccagatagagattgtgctgcaaaagcttctaatggtgaattttctatt
gctgataatggtttggctaactaccaaaactacattgatcaaattgttgctgctgttaaacaattccagatgttagagttgttgctgttattgaacc
agattcttttggctaatttggttacaaattttaaacgttcaaaagtgtgctaatgctaaatctactacttgactgctgttaattatgctttgaagcaattat
cttctgttggtgttttatcaatatatggatgctggtcatgctggtggtttgggtgggccgcgcactaatttaactccagctgctcaattgtttgctcaagttt
attctgatgctggtaaatctccattcattaaggtttggctactaatgttgctaattacaatgctttgtctgctgcttctccagatccaattactcaag
gtgatccaaattacgatgaaattcattacattaatgctttggctccagctttgcaatctgctggttttccagctactttattgttgatcaaggtagatc
aggtcaacaaaatcatagacaacaatggggtgattggtgtaacattaaaggtgctggttttggtactagaccaactactaatactggttcttcttt
gattgattctattgtttgggttaaaccaggtggtgaatctgatggtacttctaattcttcatctccaagatttgattctacttgttctttgtctgatgctac
tcaaccagctccagaagctggtacttggtttcaagcttactttgaaactttggtttctaaagctaatccaccattgttataaggcgcgcc
(SEQ ID NO: 8)

*Volvariella volvacea* cbhII-I
ttaattaaaatgtctagattctctgctttgactgctttgttgttgtcttttgccattgttggctattgctcaatctccattgtatggtcaatgtggtggtaat
ggttggactggtccaaaaacttgtgtttctggtgctacttgtactgttattaatgattggtattggcaatgtttgccaggtaatggtccaacttcttctt
ctccaacttctactccaactacaactactactactggtggtccacaaccaactgttccagctgctggtaatccatatactggttacgaaatttactt
gtctccatattatgctgctgaagctcaagctgctgctgctcaaatttctgatgctactcaaaaagctaaagctttgaaagttgctcaaattccaact
tttacttggttttgatgttattgctaaaacttctacttttgggtgattattttggctgaagcttctgcttttgggtaaatcttctggtaaaagtacttggttca
aattgttgtttatgatttgccagatagagattgtgctgctttggcttctaatggtgaattttctattgctaacaacggtttgaacaattacaaaggttac
attgatcaattggttgcacaaattaagaaatacccagatgttagagttgttgctgttattgaaccagattcttttggctaatttggttacaaatttgaac
gtttctaagtgtgctaatgctcaaactgcttacaaaagctggtgttacttatgctttgcaacaattgaactcctgttggtgtttacatgtatttggatgct
ggtcatgctggttggttgggttggccagctaatttgaatccagctgctcaattgttttctccaattgtatagagatgctggttctccacaatacgttag
aggtttggctactaatgttgctaattacaatgctttgtctgctgcttcttcaccagatccagttactcaaggtaatccaaattacgatgaattgcattacat
taatgctttggctccagctttgcaatctggtggttttccagctcattttattgttgatcaaggtagatcaggtgttcaaaacattagacaacaatggg
gtgattggtgtaatgttaaaggtgctggttttggtcaaagaccaactttatctactggttcttcttttgattgatgctattgtttggattaaaccaggtg
gtgaatgtgatggtactactacatcttctccaagatatgattctcattgtggtttgtctgatgctactccaaatgctcctgaagctggtcaatgg
tttcaagcttactttgaaacttttggttagaaatgcttctccaccattgttataaggcgcgcc (SEQ ID NO: 9)

*Piromyces* sp. E2 cel6A
ttaattaaaatgaaggcttctattgctttgactgctattgctgctttggctgctgctaatgcttctgctgctgttttttctgaaagattgggttatccatgttgt
agaggtaatgaagttttctacactgataatgatggtgattgggtgttgaaaatggtaattggtgtggtattggtggtgcttctgctactacttgttg
gtcacaagctttaggttaccettgttgtacttctacttctgatgttgcttacgttgatggtgacggtaactggggtgtcgaaaacggtaactggtgc
ggtataattgcaggtggtaattcttctaacaacaactctggttctactattaatgttggtgatgttactattggtaaccaatacactcatactggtaat
ccatttgctggtcataaattctttattaacccatactatactgctgaagttgatggtgctattgctcaaatttctaatgcttctttgagagctaaagctg
aaaagatgaaagaattttctaacgctatttggttggatactattaagaatatgaacgaatggttggaaaagaatttgaaatatgctttggctgaac
aaaatgaactggtaagctgttttgacagttttgttgtttgttgctgctagagattgcatgctttagcttctaatggtggttggctaa
tgattctgattgggcaagatatcaatctgaatacattgatgttattgaagaaagtgaaaacttacaagtctcaaccagttgtttggttgttgaac
cagattcttttggctaatatggttacaaatttggattctactccagctcgtgtagagattctgaaaaatactatatggatggtcatgcttacttgattaaaa
agttgggtgttttgccacatgttgcaatgtatttggatattggtcatgcttttttggttgggttgggatgataatagattgaaagctggtaaagtttact
ctaaggttattcaatctggtgctccaggtaatgttagaggttttgcttctaatgttgctaattatactccatgggaagatccaacttgtctagaggt
ccagatactgaatggaatccatgtccatgctacaaaaatcaatgtacaaagattttaagtctgctggtattaagtctgtttacttc
attgatgatacttctagaaatggtcataagactgataagaactcatccaggtgaatggtgtaatcaaacaggtgttggtattggtctagaccaca
agctaatccaatttctggtatggattacttgatgcttttattgggttaaaccattgggtgaatctgatggttattctgatactactgctgtcagatat
gatggttattgtggtcatgctactgctatgaaaccagctcctgaagctggtcaatgtttcaaaaacatttcgaacaaggtttggaaaatgctaat
ccaccattgttataaggcgcgcc (SEQ ID NO: 10)

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function at the website of Entelechon (visited Sep. 4, 2009). Constructing a rudimentary algorithm to assign codons based on a given frequency can also easily be accomplished with basic mathematical functions by one of ordinary skill in the art.

A number of options are available for synthesizing codon-optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, an entire polypeptide sequence, or fragment, variant, or derivative thereof is codon-optimized by any of the methods described herein. Various desired fragments, variants or derivatives are designed, and each is then codon-optimized individually. In addition, partially codon-optimized coding regions of the present invention can be designed and constructed. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a yeast species such as *Saccharomyces cerevisiae*, in place of a codon that is normally used in the native nucleic acid sequence.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon-optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

The codon-optimized coding regions can be versions encoding a Cbh2 from *Cochliobolus heterostrophus, Gibberella zeae, Irpex lacteus, Volvariella volvacea*, or *Piromyces* sp. or domains, fragments, variants, or derivatives thereof.

Codon optimization is carried out for a particular species by methods described herein. For example, in certain embodiments codon-optimized coding regions encoding polypeptides of a *Cochliobolus heterostrophus, Gibberella zeae, Irpex lacteus, Volvariella volvacea*, or *Piromyces* sp. Cbh2, or domains, fragments, variants, or derivatives thereof are optimized according to yeast codon usage, e.g., *Saccharomyces cerevisiae*. In particular, the present invention relates to codon-optimized coding regions encoding polypeptides of a *Cochliobolus heterostrophus, Gibberella zeae, Irpex lacteus, Volvariella volvacea*, or *Piromyces* sp. Cbh2, or domains, variants, or derivatives thereof which have been optimized according to yeast codon usage, for example, *Saccharomyces cerevisiae* codon usage. Also provided are polynucleotides, vectors, and other expression constructs comprising codon-optimized coding regions encoding Cbh2 polypeptides of *Cochliobolus heterostrophus, Gibberella zeae, Irpex lacteus, Volvariella volvacea*, or *Piromyces* sp., or domains, fragments, variants, or derivatives thereof, and various methods of using such polynucleotides, vectors and other expression constructs.

In certain embodiments described herein, a codon-optimized coding region encoding the polypeptide sequence of any of SEQ ID NOs:11-15, or domains, fragments, variants, or derivatives thereof, is optimized according to codon usage in yeast (*Saccharomyces cerevisiae*). Alternatively, a codon-optimized coding region encoding the polypeptide sequence of any of SEQ ID NOs:11-15 can be optimized according to codon usage in any plant, animal, or microbial species.

Cbh2 Polypeptides

The present invention further relates to the expression of *Cochliobolus heterostrophus*, *Gibberella zeae*, *Irpex lacteus*, *Volvariella volvacea*, or *Piromyces* sp. Cbh2 polypeptides in a host cell, such as *Saccharomyces cerevisiae*. The sequences of *Cochliobolus heterostrophus*, *Gibberella zeae*, *Irpex lacteus*, *Volvariella volvacea*, and *Piromyces* sp. Cbh2 polypeptides are set forth in Table 6 below.

The present invention further encompasses polypeptides which comprise, or alternatively consist of, an amino acid sequence which is at least about 80%, 85%, 90%, 95%, 96%, 97%, 98%, or 99% identical to, for example, the polypeptide sequences shown in any of SEQ ID NOs: 11-15, and/or domains, fragments, variants, or derivative thereof, of any of these polypeptides (e.g., those fragments described herein, or domains of any of SEQ ID NOs: 11-15).

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted, (indels) or substituted with another amino acid. These alterations of the reference

TABLE 6

Cellobiohydrolase 2 (Cbh2) polypeptide sequences.

*Cochliobolus heterostrophus* C4 cel7 (GenBank AAM76664.1)
MLSNVFLTAALAAGLAQALPQATPTPTAAPSGNPFAGKNFYANPYYSSEVHTLAMPSLP
ASLKPAATAVAKVGSFVWMDTMAKVPLMDTYLADIKAKNAAGANLMGTFVVYDLPD
RDCAALASNGELKIDEGGVEKYKTQYIDKIAAIIKKYPDVKINLAIEPDSLANMVTNMGV
QKCSRAAPYYKELTAYALKTLNFNNVDMYMDGGHAGWLGWDANIGPTAKLFAEVYK
AAGSPRGVRGIVTNVSNYNALRVSSCPSITQGNKNCDEERYINALAPLLKNEGFPAHFIV
DQGRSGKVPTNQQEWGDWCNVSGAGFGTRPTTNTGNALIDAIVWVKPGGESDGTSDTS
AARYDAHCGRNSAFKPAPEAGTWFQAYFEMLLKNANPALA (SEQ ID NO: 11)

*Gibberella zeae* K59 cel6 (GenBank Accession AY302753.1)
MTAYKLFLAAAFAATALAAPVEERQSCSNGVWSQCGGQNWSGTPCCTSGNKCVKVND
FYSQCQPGSADPSPTSTIVSATTTKATTTGSGGSVTSPPPVATNNPFSGVDLWANNYYRS
EVSTLAIPKLSGAMATAAAKVADVPSFQWMDTYDHISFMEDSLADIRKANKAGGNYAG
QFVVYDLPDRDCAAAASNGEYSLDKDGKNKYKAYIADQGILQDYSDTRIILVIEPDSLA
NMVTNMNVPKCANAASAYKELTIHALKELNLPNVSMYIDAGHGGWLGWPANLPPAAQ
LYGQLYKDAGKPSRLRGLVTNVSNYNAWKLSSKPDYTESNPNYDEQKYIHALSPLLEQE
GWPGAKFIVDQGRSGKQPTGQKAWGDWCNAPGTGFGLRPSANTGDALVDAFVWVKP
GGESDGTSDTSAARYDYHCGIDGAVKPAPEAGTWFQAYFEQLLKNANPSFL (SEQ ID
NO: 12)

*Irpex lacteus* MC-2 cex3 (GenBank Accession BAG48183.1)
MTAYKLFLAAAFAATALAAPVEERQSCSNGVWSQCGGQNWSGTPCCTSGNKCVKVND
FYSQCQPGSADPSPTSTIVSATTTKATTTGSGGSVTSPPPVATNNPFSGVDLWANNYYRS
EVSTLAIPKLSGAMATAAAKVADVPSFQWMDTYDHISFMEDSLADIRKANKAGGNYAG
QFVVYDLPDRDCAAAASNGEYSLDKDGKNKYKAYIADQGILQDYSDTRIILVIEPDSLA
NMVTNMNVPKCANAASAYKELTIHALKELNLPNVSMYIDAGHGGWLGWPANLPPAAQ
LYGQLYKDAGKPSRLRGLVTNVSNYNAWKLSSKPDYTESNPNYDEQKYIHALSPLLEQE
GWPGAKFIVDQGRSGKQPTGQKAWGDWCNAPGTGFGLRPSANTGDALVDAFVWVKP
GGESDGTSDTSAARYDYHCGIDGAVKPAPEAGTWFQAYFEQLLKNANPSFL (SEQ ID
NO: 13)

*Volvariella volvacea* cbhII-I (GenBank Accession AAT64008.1)
MSRFSALTALLLSLPLLAIAQSPLYGQCGGNGWTGPKTCVSGATCTVINDWYWQCLPG
NGPTSSSPTSTPTTTTTTGGPQPTVPAAGNPYTGYEIYLSPYYAAEAQAAAAQISDATQK
AKALKVAQIPTFTWFDVIAKTSTLGDYLAEASALGKSSGKKYLVQIVVYDLPDRDCAAL
ASNGEFSIANNGLNNYKGYIDQLVAQIKKYPDVRVVAVIEPDSLANLVTNLNVSKCANA
QTAYKAGVTYALQQLNSVGVYMYLDAGHAGWLGWPANLNPAAQLFSQLYRDAGSPQ
YVRGLATNVANYNALSASSPDPVTQGNPNYDELHYINALAPALQSGGFPAHFIVDQGRS
GVQNIRQQWGDWCNVKGAGEGQRPTLSTGSSLIDAIVWIKPGGECDGTTNTSSPRYDSH
CGLSDATPNAPEAGQWFQAYFETLVRNASPPL (SEQ ID NO: 14)

*Piromyces* sp. E2 cel6A (GenBank Accession AAL92497.1)
MKASIALTAIAALAANASAACFSERLGYPCCRGNEVFYTDNDGDWGVENGNWCGIGGA
SATTCWSQALGYPCCTSTSDVAYVDGDGNWGVENGNWCGIIAGGNSSNNNSGSTINVG
DVTIGNQYTHTGNPFAGHKFFINPYYTAEVDGAIAQISNASLRAKAEKMKEFSNAIWLDT
IKNMNEWLEKNLKYALAEQNETGKTVLTVFVVYDLPGRDCHALASNGELLANDSDWA
RYQSEYIDVIEEKLKTYKSQPVVLVVEPDSLANMVTNLDSTPACRDSEKYYMDGHAYLI
KKLGVLPHVAMYLDIGHAFWLGWDDNRLKAGKVYSKVIQSGAPGNVRGFASNVANYT
PWEDPTLSRGPDTEWNPCPDEKRYIEAMYKDEKSAGIKSVYFIDDTSRNGHKTDRTHPG
EWCNQTGVGIGARPQANPISGMDYLDAFYWVKPLGESDGYSDTTAVRYDGYCGHATA
MKPAPEAGQWFQKHFEQGLENANPPL (SEQ ID NO: 15)

sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, any of the amino acid sequences of SEQ ID NOs: 11-15 can be determined conventionally using known computer programs. As discussed above, a method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237-245 (1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. Also as discussed above, manual corrections can be made to the results in certain instances.

In certain aspects of the invention, the polypeptides and polynucleotides of the present invention are provided in an isolated form, e.g., purified to homogeneity.

The present invention also encompasses polypeptides which comprise, or alternatively consist of, an amino acid sequence which is at least about 80%, 85%, 90%, 95%, 96%, 97%, 98%, or 99% similar to the polypeptide of any of SEQ ID NOs: 11-15, or to portions of such polypeptide, wherein the portion can contain at least 30 amino acids, at least 50 amino acids, at least 100 amino acids, at least 150 amino acids, at least 200 amino acids, at least 250 amino acids, at least 300 amino acids, or at least 350 amino acids.

As known in the art "similarity" between two polypeptides is determined by comparing the amino acid sequence and conserved amino acid substitutes thereto of the polypeptide to the sequence of a second polypeptide.

The present invention further relates to a domain, fragment, variant, derivative, or analog of the polypeptide of any of SEQ ID NOs: 11-15.

Fragments or portions of the polypeptides of the present invention can be employed for producing the corresponding full-length polypeptide by peptide synthesis, therefore, the fragments can be employed as intermediates for producing the full-length polypeptides.

Fragments of Cbh2 polypeptides of the present invention can encompass domains, proteolytic fragments, and deletion fragments of *Cochliobolus heterostrophus, Gibberella zeae, Irpex lacteus, Volvariella volvacea*, or *Piromyces* sp. Cbh2 polypeptides. The fragments can optionally retain a specific biological activity of the Cbh2 protein. Exemplary fragments include those described in Table 2 above. Polypeptide fragments further include any portion of the polypeptide which comprises a catalytic activity of the Cbh2 protein.

The variant, derivative or analog of the polypeptide of any of SEQ ID NOs: 11-15, can be (i) one in which one or more of the amino acid residues are substituted with a conserved or non-conserved amino acid residue and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e., not membrane bound, yet still binds ligands to the membrane bound receptor. Such variants, derivatives and analogs are deemed to be within the scope of those skilled in the art from the teachings herein.

The polypeptides of the present invention further include variants of the polypeptides. A "variant" of the polypeptide can be a conservative variant, or an allelic variant. As used herein, a conservative variant refers to alterations in the amino acid sequence that does not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

By an "allelic variant" is intended alternate forms of a gene occupying a given locus on a chromosome of an organism. Genes II, Lewin, B., ed., John Wiley & Sons, New York (1985). Non-naturally occurring variants can be produced using art-known mutagenesis techniques. Allelic variants, though possessing a slightly different amino acid sequence than those recited above, will still have the same or similar biological functions associated with the *Cochliobolus heterostrophus, Gibberella zeae, Irpex lacteus, Volvariella volvacea*, or *Piromyces* sp. Cbh2 protein.

The allelic variants, the conservative substitution variants, and members of the Cbh2 protein family, will have an amino acid sequence having at least 75%, at least 80%, at least 90%, at least 95%, at least 96%, at least 97%, at least 98%, or at least 99% amino acid sequence identity with a *Cochliobolus heterostrophus, Gibberella zeae, Irpex lacteus, Volvariella volvacea*, or *Piromyces* sp. Cbh2 amino acid sequence set forth in any one of SEQ ID NOs:11-15. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N terminal, C terminal, or internal extensions, deletions, or insertions into the peptide sequence shall not be construed as affecting homology.

Thus, the proteins and peptides of the present invention include molecules comprising the amino acid sequence of any one of SEQ ID NOs: 11-15 or fragments thereof having a consecutive sequence of at least about 3, 4, 5, 6, 10, 15, 20, 25, 30, 35, 50, 100, 150, 200, 250, 300, 350, or more amino acid residues of the *Cochliobolus heterostrophus, Gibberella zeae, Irpex lacteus, Volvariella volvacea*, or *Piromyces* sp. Cbh2 polypeptide sequence; amino acid sequence variants of such sequences wherein at least one amino acid residue has been inserted N- or C terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other organisms, the alleles or other naturally occurring variants of the family of proteins; and derivatives wherein the protein has been covalently modified by substitution, chemical, enzymatic, or other appropriate means with a moiety other than a naturally occurring amino acid (for example, a detectable moiety such as an enzyme or radioisotope).

Using known methods of protein engineering and recombinant DNA technology, variants can be generated to improve or alter the characteristics of the CBH polypeptides. For instance, one or more amino acids can be deleted from the N-terminus or C-terminus of the secreted protein without substantial loss of biological function.

Thus, the invention further includes *Cochliobolus heterostrophus, Gibberella zeae, Irpex lacteus, Volvariella volvacea,* or *Piromyces* sp. Cbh2 polypeptide variants which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. See, e.g., Cunningham and Wells, Science 244:1081-1085 (1989). The resulting mutant molecules can then be tested for biological activity.

As the authors state, these two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The terms "derivative" and "analog" refer to a polypeptide differing from the *Cochliobolus heterostrophus, Gibberella zeae, Irpex lacteus, Volvariella volvacea,* or *Piromyces* sp. Cbh2 polypeptide, but retaining essential properties thereof. Generally, derivatives and analogs are overall closely similar, and, in many regions, identical to the *Cochliobolus heterostrophus, Gibberella zeae, Irpex lacteus, Volvariella volvacea,* or *Piromyces* sp. Cbh2 polypeptide. The term "derivative" and "analog" when referring to *Cochliobolus heterostrophus, Gibberella zeae, Irpex lacteus, Volvariella volvacea,* and *Piromyces* sp. Cbh2 polypeptides of the present invention include polypeptides which retain at least some of the activity of the corresponding native polypeptide, e.g., the exoglucanase activity.

Derivatives of *Cochliobolus heterostrophus, Gibberella zeae, Irpex lacteus, Volvariella volvacea,* or *Piromyces* sp. Cbh2 polypeptides of the present invention, are polypeptides which have been altered so as to exhibit additional features not found on the native polypeptide. Derivatives can be covalently modified by substitution, chemical, enzymatic, or other appropriate means with a moiety other than a naturally occurring amino acid (for example, a detectable moiety such as an enzyme or radioisotope). Examples of derivatives include fusion proteins.

An analog is another form of a *Cochliobolus heterostrophus, Gibberella zeae, Irpex lacteus, Volvariella volvacea,* or *Piromyces* sp. Cbh2 polypeptide of the present invention. An "analog" also retains substantially the same biological function or activity as the polypeptide of interest, i.e., functions as a cellobiohydrolase. An analog includes a proprotein which can be activated by cleavage of the proprotein portion to produce an active mature polypeptide.

The polypeptide of the present invention can be a recombinant polypeptide, a natural polypeptide, or a synthetic polypeptide.

Tethered and Secreted Cbh2 Polypeptides

According to the present invention, the *Cochliobolus heterostrophus, Gibberella zeae, Irpex lacteus, Volvariella volvacea,* or *Piromyces* sp. Cbh2 polypeptides can be either tethered or secreted. As used herein, a protein is "tethered" to an organism's cell surface if at least one terminus of the protein is bound, covalently and/or electrostatically for example, to the cell membrane or cell wall. It will be appreciated that a tethered protein can include one or more enzymatic regions that can be joined to one or more other types of regions at the nucleic acid and/or protein levels (e.g., a promoter, a terminator, an anchoring domain, a linker, a signaling region, etc.). While the one or more enzymatic regions may not be directly bound to the cell membrane or cell wall (e.g., such as when binding occurs via an anchoring domain), the protein is nonetheless considered a "tethered enzyme" according to the present specification.

Tethering can, for example, be accomplished by incorporation of an anchoring domain into a recombinant protein that is heterologously expressed by a cell, or by prenylation, fatty acyl linkage, glycosyl phosphatidyl inositol anchors or other suitable molecular anchors which can anchor the tethered protein to the cell membrane or cell wall of the host cell. A tethered protein can be tethered at its amino terminal end or optionally at its carboxy terminal end.

As used herein, "secreted" means released into the extracellular milieu, for example into the media. Although tethered proteins can have secretion signals as part of their immature amino acid sequence, they are maintained as attached to the cell surface, and do not fall within the scope of secreted proteins as used herein.

As used herein, "flexible linker sequence" refers to an amino acid sequence which links two amino acid sequences, for example, a cell wall anchoring amino acid sequence with an amino acid sequence that contains the desired enzymatic activity. The flexible linker sequence allows for necessary freedom for the amino acid sequence that contains the desired enzymatic activity to have reduced steric hindrance with respect to proximity to the cell and can also facilitate proper folding of the amino acid sequence that contains the desired enzymatic activity.

In some embodiments of the present invention, the tethered *Cochliobolus heterostrophus, Gibberella zeae, Irpex lacteus, Volvariella volvacea,* or *Piromyces* sp. Cbh2 polypeptides are tethered by a flexible linker sequence linked to an anchoring domain. In some embodiments, the anchoring domain is the anchoring domain of CWP2 (for carboxy terminal anchoring) or FLO1 (for amino terminal anchoring) from *S. cerevisiae*.

In some embodiments, heterologous secretion signals can be added to the expression vectors of the present invention to facilitate the extra-cellular expression of cellulase proteins. In some embodiments, the heterologous secretion signal is the secretion signal from *T. reesei* Xyn2.

Cbh2 Fusion Polypeptides

The present invention also encompasses fusion proteins comprising two or more polypeptides. For example, the fusion proteins can be a fusion of a *Cochliobolus heterostrophus, Gibberella zeae, Irpex lacteus, Volvariella volvacea,* or *Piromyces* sp. Cbh2 and a second peptide. The Cbh2 and the second peptide can be fused directly or indirectly, for example, through a linker sequence. The fusion protein can comprise for example, a second peptide that is N-terminal to the Cbh2 and/or a second peptide that is C-terminal to the heterologous cellulase. Thus, in certain embodiments, the polypeptide of the present invention comprises a first polypeptide and a second polypeptide, wherein the first polypeptide comprises a *Cochliobolus heterostrophus, Gibberella zeae, Irpex lacteus, Volvariella volvacea,* or *Piromyces* sp. Cbh2 polypeptide.

According to the present invention, the fusion protein can comprise a first and second polypeptide wherein the first polypeptide comprises a *Cochliobolus heterostrophus, Gibberella zeae, Irpex lacteus, Volvariella volvacea,* or *Piromyces* sp. Cbh2 polypeptide and the second polypeptide comprises a signal sequence. The signal sequence can be from any organism. For example, in some embodiments, the second polypeptide is an *S. cerevisiae* polypeptide. In one particular embodiment, the *S. cerevisiae* polypeptide is the *S. cerevisiae* alpha mating factor signal sequence. In some embodiments the signal sequence comprises the amino acid sequence MRFPSIFTAVLFAASSALA (SEQ ID NO: 16).

According to another embodiment, the fusion protein can comprise a first and second polypeptide, wherein the first polypeptide comprises a *Cochliobolus heterostrophus, Gibberella zeae, Irpex lacteus, Volvariella volvacea,* or *Piromyces* sp. Cbh2 polypeptide and the second polypeptide comprises a polypeptide used to facilitate purification or identification or a reporter peptide. The polypeptide used to facilitate purification or identification or the reporter peptide can be, for example, a HIS-tag, a GST-tag, an HA-tag, a FLAG-tag, a MYC-tag, or a fluorescent protein.

According to yet another embodiment, the fusion protein can comprise a first and second polypeptide, wherein the first polypeptide comprises a Cbh2 and the second polypeptide comprises an anchoring peptide. In some embodiments, the anchoring domain is the anchoring domain of CWP2 (for carboxy terminal anchoring) or FLO1 (for amino terminal anchoring) from *S. cerevisiae*.

According to yet another embodiment, the fusion protein can comprise a first and second polypeptide, wherein the first polypeptide comprises a *Cochliobolus heterostrophus, Gibberella zeae, Irpex lacteus, Volvariella volvacea,* or *Piromyces* sp. Cbh2 and the second polypeptide comprises a cellulose binding module (CBM). In some embodiments, the CBM is from *Neosartorya fischeri* Cbh1, *H. grisea* Cbh1, *Chaetomium thermophilum* Cbh1, *T. reesei* Cbh1 or *T. reesei* Cbh2, or a domain, fragment, variant, or derivative thereof.

In certain other embodiments, the first polypeptide and the second polypeptide are fused via a linker sequence. The linker sequence can, in some embodiments, be encoded by a codon-optimized polynucleotide. (Codon-optimized polynucleotides are described in more detail herein.) An amino acid sequence corresponding to a codon-optimized linker 1 according to the invention is a flexible linker-strep tag-TEV site-FLAG-flexible linker fusion and corresponds to GGGGSGGGGS AWHPQFGG ENLYFQG DYKDDDK GGGGSGGGGS (SEQ ID NO: 17).

The DNA sequence encoding the polypeptide of SEQ ID NO:17 is:

```
                                          (SEQ ID NO: 18)
GGAGGAGGTGGTTCAGGAGGTGGTGGGTCTGCTTGGCATCCACAATTTGG

AGGAGGCGGTGGTGAAAATCTGTATTTCCAGGGAGGCGGAGGTGATTACA

AGGATGACGACAAAGGAGGTGGTGGATCAGGAGGTGGTGGCTCC
```

An amino acid sequence corresponding to optimized linker 2 is a flexible linker-strep tag-linker-TEV site-flexible linker and corresponds to GGGGSGGGGS WSHPQFEK GG ENLYFQG GGGGSGGGGS (SEQ ID NO: 19). The DNA sequence is as follows:

```
                                          (SEQ ID NO: 20)
ggtggcggtggatctggaggaggcggttcttggtctcacccacaatttga aaagggtggagaaaacttgtactttcaaggcggtggtggaggttctggcg gaggtggctccggctca.
```

In further embodiments of the fusion protein, the first and second polypeptide are in the same orientation, or the second polypeptide is in the reverse orientation of the first polypeptide. In additional embodiments, the first polypeptide is either N-terminal or C-terminal to the second polypeptide. In certain other embodiments, the first polypeptide and/or the second polypeptide are encoded by codon-optimized polynucleotides, for example, polynucleotides codon-optimized for *S. cerevisiae*.

Vectors and Host Cells

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention can be employed for producing polypeptides by recombinant techniques. Thus, for example, the polynucleotide can be included in any one of a variety of expression vectors for expressing a polypeptide. Such vectors include chromosomal, nonchromosomal and synthetic DNA sequences, e.g., derivatives of SV40; bacterial plasmids; and yeast plasmids. Such vectors also include "suicide vectors" which are not self-replicating but can be replicated after insertion into the host chromosome. Other vectors can also be used.

The appropriate DNA sequence can be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. Representative examples of such promoters are as follows:

TABLE 7

Promoters.

| Gene | Organism | Systematic name | Reason for use/benefits |
| --- | --- | --- | --- |
| PGK1 | S. cerevisiae | YCR012W | Strong constitutive promoter |
| ENO1 | S. cerevisiae | YGR254W | Strong constitutive promoter |
| TDH3 | S. cerevisiae | YGR192C | Strong constitutive promoter |
| TDH2 | S. cerevisiae | YJR009C | Strong constitutive promoter |
| TDH1 | S. cerevisiae | YJL052W | Strong constitutive promoter |
| ENO2 | S. cerevisiae | YHR174W | Strong constitutive promoter |
| GPM1 | S. cerevisiae | YKL152C | Strong constitutive promoter |
| TPI1 | S. cerevisiae | YDR050C | Strong constitutive promoter |

Additional the *E. coli*, lac or trp, and other promoters known to control expression of genes in prokaryotic or lower eukaryotic cells. The expression vector also contains a ribosome binding site for translation initiation and a transcription terminator. The vector can also include appropriate sequences for amplifying expression, or can include additional regulatory regions.

In addition, the expression vectors can contain one or more selectable marker genes to provide a phenotypic trait for selection of transformed host cells such as URA3, HIS3, LEU2, TRP1, LYS2 or ADE2, dihydrofolate reductase or neomycin (G418) resistance or zeocin resistance for eukaryotic cell culture, or chloramphenicol, thiamphenicol, streptomycin, tetracycline, kanamycin, hygromycin, phleomycin or ampicillin resistance in *E. coli*.

The vector containing the appropriate DNA sequence as herein, as well as an appropriate promoter or control sequence, can be employed to transform an appropriate host to permit the host to express the protein.

Thus, in certain aspects, the present invention relates to host cells containing the above-described constructs. The host cell can be a higher eukaryotic cell, such as a mammalian cell, or a lower eukaryotic cell, such as a yeast cell, e.g., *Saccharomyces cerevisiae*, or the host cell can be a prokaryotic cell, such as a bacterial cell.

Representative examples of appropriate hosts include, for example, bacterial cells, such as *E. coli, Streptomyces, Salmonella typhimurium*; thermophilic or mesophilic bacteria; fungal cells, such as yeast; and plant cells, etc. The selection of an appropriate host is deemed to be within the scope of those skilled in the art from the teachings herein.

Appropriate fungal hosts include yeast. In certain aspects of the invention the yeast is *Saccharomyces cerevisiae, Saccharomyces pastorianus* (also known as *Saccharomyces carlsbergensis*), *Saccharomyces bayanus, Kluyveromyces lactis, Kluyveromyces marxianus, Schizosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus or Schwanniomyces occidentalis*. In some embodiments, the host cell can be an oleaginous yeast cell. In some particular embodiments, the oleaginous yeast cell is a *Blakeslea, Candida, Cryptococcus, Cunninghamella, Lipomyces, Mortierella, Mucor, Phycomces, Pythium, Rhodosporidium, Rhodotorula, Trichosporon or Yarrowia* cell.

According to the methods described herein, the yeast strains can be modified, e.g. to improve growth, selection, and/or stability. Thus, for example, the *Saccharomyces cerevisiae, Saccharomyces pastorianus* (also known as *Saccharomyces carlsbergensis*), *Saccharomyces bayanus, Kluyveromyces lactis, Kluyveromyces marxianus, Schizosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus or Schwanniomyces occidentalis* can include deletions, insertions, and/or rearrangements and still be considered *Saccharomyces cerevisiae, Saccharomyces pastorianus* (also known as *Saccharomyces carlsbergensis*), *Saccharomyces bayanus, Kluyveromyces lactis, Kluyveromyces marxianus, Schizosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus or Schwanniomyces occidentalis*. Derivatives of the aforementioned yeast cells, i.e., yeast that have been adapted sufficiently to diverge the genome to the extent that it is a different species can also be used according to the present methods. Thus, the host cells described herein include derivatives of *Saccharomyces cerevisiae, Saccharomyces pastorianus* (also known as *Saccharomyces carlsbergensis*), *Saccharomyces bayanus, Kluyveromyces lactis, Kluyveromyces marxianus, Schizosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus and Schwanniomyces occidentalis*.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In one aspect of this embodiment, the construct further comprises regulatory sequences, including, for example, a promoter, operably associated to the sequence. Large numbers of suitable vectors and promoters are known to those of skill in the art, and are commercially available. The following vectors are provided by way of example.

Yeast: Yeast vectors include those of five general classes, based on their mode of replication in yeast, YIp (yeast integrating plasmids), YRp (yeast replicating plasmids), YCp (yeast replicating plasmids with centromere (CEN)

elements incorporated), YEp (yeast episomal plasmids), and YLp (yeast linear plasmids). With the exception of the YLp plasmids, all of these plasmids can be maintained in *E. coli* as well as in *Saccharomyces cerevisiae* and thus are also referred to as yeast shuttle vectors. In certain aspects, these plasmids contain two types of selectable genes: plasmid-encoded drug-resistance genes and cloned yeast genes, where the drug resistant gene is typically used for selection in bacterial cells and the cloned yeast gene is used for selection in yeast. Drug-resistance genes include ampicillin, kanamycin, tetracycline, neomycin and sulfometuron methyl. Cloned yeast genes include HIS3, LEU2, LYS2, TRP1, URA3, TRP1 and SMR1. pYAC vectors can also be utilized to clone large fragments of exogenous DNA on to artificial linear chromosomes.

In certain aspects of the invention, YCp plasmids, which have high frequencies of transformation and increased stability to due the incorporated centromere elements, are utilized. In certain other aspects of the invention, YEp plasmids, which provide for high levels of gene expression in yeast, are utilized. In additional aspects of the invention, YRp plasmids are utilized.

In certain embodiments, the vector comprises (1) a first polynucleotide, where the first polynucleotide encodes for a *Cochliobolus heterostrophus, Gibberella zeae, Irpex lacteus, Volvariella volvacea*, or *Piromyces* sp. Cbh2, or domain, fragment, variant, or derivative thereof and (2) a second polynucleotide, where the second polynucleotide encodes for a *Cochliobolus heterostrophus, Gibberella zeae, Irpex lacteus, Volvariella volvacea*, or *Piromyces* sp. Cbh2, or domain, fragment, variant, or derivative thereof.

In certain additional embodiments, the vector comprises a first polynucleotide encoding for a *Cochliobolus heterostrophus, Gibberella zeae, Irpex lacteus, Volvariella volvacea*, or *Piromyces* sp. Cbh2 and a second polynucleotide encoding for the CBM domain of *T. reesei* CBH1 or *T. reesei* Cbh2. In further embodiments, the first and second polynucleotides are in the same orientation, or the second polynucleotide is in the reverse orientation of the first polynucleotide. In additional embodiments, the first polynucleotide is either N-terminal or C-terminal to the second polynucleotide. In certain other embodiments, the first polynucleotide and/or the second polynucleotide are encoded by codon-optimized polynucleotides, for example, polynucleotides codon-optimized for *S. cerevisiae*.

In particular embodiments, the vector of the present invention is a plasmid selected from the group consisting of pRDH150, pRDH151, pRDH152, pRDH153, and pRDH154. Descriptions of these plasmids are found in Example 1 and FIG. 1. However, any other plasmid or vector can be used as long as they are replicable and viable in the host.

Promoter regions can be selected from any desired gene. Particular named yeast promoters include the ENO1 promoter, the PGK1 promoter, the TEF1 promoter, and the HXT7 promoter. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Introduction of the construct into a host yeast cell, e.g., *Saccharomyces cerevisiae*, can be effected by lithium acetate transformation, spheroplast transformation, or transformation by electroporation, as described, for example, in Current Protocols in Molecular Biology, 13.7.1-13.7.10.

Introduction of the construct in other host cells can be effected by calcium phosphate transfection, DEAE-Dextran mediated transfection, or electroporation. See e.g., Davis, L., et al., Basic Methods in Molecular Biology, (1986).

The constructs in host cells can be used in a conventional manner to produce the gene product encoded by the recombinant sequence. Alternatively, the polypeptides of the invention can be synthetically produced by conventional peptide synthesizers.

Following creation of a suitable host cell and growth of the host cell to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Yeast cells, e.g., *Saccharomyces cerevisiae*, employed in expression of proteins can be manipulated as follows. The Cbh2 polypeptides can be secreted by cells and therefore can be easily recovered from supernatant using methods known to those of skill in the art. Proteins can also be recovered and purified from recombinant cell cultures by methods including spheroplast preparation and lysis, cell disruption using glass beads, and cell disruption using liquid nitrogen, for example.

Various mammalian cell culture systems can also be employed to express recombinant protein. Expression vectors will comprise an origin of replication, a suitable promoter and enhancer, and also any necessary ribosome binding sites, polyadenylation site, splice donor and acceptor sites, transcriptional termination sequences, and 5° flanking nontranscribed sequences.

Additional methods include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The Cbh2 polypeptides can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Cbh2 polypeptides are provided in an isolated form, and, in certain aspects, are substantially purified. A recombinantly produced version of a Cbh2 polypeptide, including the secreted polypeptide, can be substantially purified using techniques described herein or otherwise known in the art, such as, for example, by the one-step method described in Smith and Johnson, Gene 67:31-40 (1988). Cbh2 polypeptides also can be purified from natural, synthetic or recombinant sources using techniques described herein or otherwise known in the art.

The Cbh2 polypeptides of the present invention can be in the form of the secreted protein, including the mature form, or can be a part of a larger protein, such as a fusion protein. It can be advantageous to include an additional amino acid sequence which contains secretory or leader sequences, pro-sequences, sequences which aid in purification, such as multiple histidine residues, or an additional sequence for stability during recombinant production.

Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion can be accomplished by the incorporation of a DNA sequence that codes for a secretion signal which is functional in the host production host. Methods for choosing appropriate signal sequences are well known in the art (see for example EP 546049; WO 9324631). The secretion signal DNA or facilitator can be located between the expression-controlling DNA and the instant gene or gene fragment, and in the same reading frame with the latter.

Heterologous Expression of Cbh2 Polypeptides in Host Cells

In order to address the limitations of the previous systems, the present invention provides *Cochliobolus heterostrophus*, *Gibberella zeae*, *Irpex lacteus*, *Volvariella volvacea*, and *Piromyces* sp. Cbh2 polypeptides, and domains, variants, and derivatives thereof that can be effectively and efficiently utilized in a consolidated bioprocessing system.

In particular, the invention relates to the production of a heterologous Cbh2 in a host organism. In certain embodiments, this host organism is yeast, such as *Saccharomyces cerevisiae*.

In certain embodiments of the present invention, a host cell comprising a vector which encodes and expresses a *Cochliobolus heterostrophus*, *Gibberella zeae*, *Irpex lacteus*, *Volvariella volvacea*, or *Piromyces* sp. Cbh2 that is utilized for consolidated bioprocessing is co-cultured with additional host cells expressing one or more additional endoglucanases, cellobiohydrolases and/or β-glucosidases. In other embodiments of the invention, a host cell transformed with a plasmid encoding *Cochliobolus heterostrophus*, *Gibberella zeae*, *Irpex lacteus*, *Volvariella volvacea*, or *Piromyces* sp. Cbh2 additionally expresses one or more heterologous endoglucanases, cellobiohydrolases or β-glucosidases. The endoglucanase, cellobiohydrolase and/or β-glucosidase can be any suitable endoglucanase, cellobiohydrolase and β-glucosidase derived from, for example, a fungal or bacterial source.

In certain embodiments of the invention, the endoglucanase(s) can be an endoglucanase I or an endoglucanase II isoform, paralogue or orthologue. In another embodiment, the endoglucanase expressed by the host cells of the present invention can be recombinant endo-1,4-β-glucanase. In certain embodiments of the present invention, the endoglucanase is an endoglucanase I from *Trichoderma reesei*. In certain other embodiments of the invention, the endoglucanase is *C. formosanus* endoglucanase I.

In certain embodiments of the present invention, the β-glucosidase is derived from *Saccharomycopsis fibuligera*. In certain embodiments, the β-glucosidase is a β-glucosidase I or a β-glucosidase II isoform, paralogue or orthologue. In certain other embodiments, the β-glucosidase expressed by the cells of the present invention can be recombinant β-glucanase I from a *Saccharomycopsis fibuligera* source.

In certain embodiments of the invention, the cellobiohydrolase(s) can be a cellobiohydrolase I and/or a cellobiohydrolase II isoform, paralogue or orthologue. In certain embodiments of the present invention the cellobiohydrolases are *Trichoderma reesei* Cbh1 or Cbh2, *T. emersonii* Cbh1 or Cbh2, or *C. lucknowense* cellobiohydrase IIb.

The transformed host cells or cell cultures, as described above, are measured for endoglucanase, cellobiohydrolase and/or β-glucosidase protein content. For the use of secreted cellulases, protein content can be determined by analyzing the host (e.g., yeast) cell supernatants. Proteins, including tethered heterologous biomass degrading enzymes, can also be recovered and purified from recombinant cell cultures by methods including spheroplast preparation and lysis, cell disruption using glass beads, and cell disruption using liquid nitrogen for example. Additional protein purification methods include trichloroacetic acid, ammonium sulfate or ethanol precipitation, acid extraction, anion or cation exchange chromatography, phosphocellulose chromatography, hydrophobic interaction chromatography, affinity chromatography, hydroxylapatite chromatography, gel filtration, and lectin chromatography. Protein refolding steps can be used, as necessary, in completing configuration of the mature protein. Finally, high performance liquid chromatography (HPLC) can be employed for final purification steps.

Protein analysis methods include methods such as the traditional Lowry method, the bicinchoninic acid protein assay reagent (Pierce) or the protein assay method according to BioRad's manufacturer's protocol. Using such methods, the protein content of saccharolytic enzymes can be estimated. Additionally, to accurately measure protein concentration a Cbh2 can be expressed with a tag, for example a His-tag or HA-tag and purified by standard methods using, for example, antibodies against the tag, a standard nickel resin purification technique or similar approach.

The transformed host cells or cell cultures, as described above, can be further analyzed for hydrolysis of cellulase (e.g., by a sugar detection assay), for a particular type of cellulase activity (e.g., by measuring the individual endoglucanase, cellobiohydrolase or β-glucosidase activity) or for total cellulase activity. Endoglucanase activity can be determined, for example, by measuring an increase of reducing ends in an endogluconase specific CMC substrate. Cellobiohydrolase activity can be measured, for example, by using insoluble cellulosic substrates such as the amorphous substrate phosphoric acid swollen cellulose (PASC) or microcrystalline cellulose (Avicel) and determining the extent of the substrate's hydrolysis. β-glucosidase activity can be measured by a variety of assays, e.g., using cellobiose.

A total cellulase activity, which includes the activity of endoglucanase, cellobiohydrolase I and cellobiohydrolase II, and β-glucosidase, can hydrolyze crystalline cellulose synergistically. Total cellulase activity can thus be measured using insoluble substrates including pure cellulosic substrates such as Whatman No. 1 filter paper, cotton linter, microcrystalline cellulose, bacterial cellulose, algal cellulose, and cellulose-containing substrates such as dyed cellulose, alpha-cellulose or pretreated lignocellulose.

It will be appreciated that suitable lignocellulosic material can be any feedstock that contains soluble and/or insoluble cellulose, where the insoluble cellulose can be in a crystalline or non-crystalline form. In various embodiments, the lignocellulosic biomass comprises, for example, wood, corn, corn cobs, corn stover, corn fiber, sawdust, bark, leaves, agricultural and forestry residues, grasses such as switchgrass, cord grass, rye grass or reed canary grass, miscanthus, ruminant digestion products, municipal wastes, paper mill effluent, newspaper, cardboard, miscanthus, sugar-processing residues, sugarcane bagasse, agricultural wastes, rice straw, rice hulls, barley straw, cereal straw, wheat straw, canola straw, oat straw, oat hulls, stover, soybean stover, forestry wastes, recycled wood pulp fiber, paper sludge, sawdust, hardwood, softwood or combinations thereof.

In certain embodiments of the present invention, a host cell comprising a vector which encodes and expresses a *Cochliobolus heterostrophus, Gibberella zeae, Irpex lacteus, Volvariella volvacea*, or *Piromyces* sp. Cbh2 that is utilized for consolidated bioprocessing is co-cultured with additional host cells expressing one or more additional heterologous endoglucanases, cellobiohydrolases and/or β-glucosidases. In other embodiments of the invention, a host cell transformed with a *Cochliobolus heterostrophus, Gibberella zeae, Irpex lacteus, Volvariella volvacea*, and *Piromyces* sp. CHB2 is transformed with and/or expresses one or more other heterologous endoglucanases, exoglucanases or β-glucosidases. The endogluconase, exogluconase and/or β-glucosidase can be any suitable endogluconase, exogluconase and β-glucosidase.

Specific activity of cellulases can also be detected by methods known to one of ordinary skill in the art, such as by the Avicel assay (described supra) that would be normalized by protein (cellulase) concentration measured for the sample. To accurately measure protein concentration a *Cochliobolus heterostrophus, Gibberella zeae, Irpex lacteus, Volvariella volvacea*, or *Piromyces* sp. Cbh2 can be expressed with a tag, for example a His-tag or HA-tag and purified by standard methods using, for example, antibodies against the tag, a standard nickel resin purification technique or similar approach.

In some embodiments the host cell comprises a heterologous cellobiohydrolase that has a specific activity of at least about 0.20%, at least about 0.25%, at least about 0.30%, at least about 0.35%, or at least about 0.40%, Avicel hydrolysis per µg cellobiohydrolase per 48 hours based on an initial 1% Avicel concentration. In some embodiments, the host cell comprises a heterologous cellobiohydrolase that has a specific activity of from about 0.20% to about 0.90%, from about 0.20% to about 0.80%, from about 0.20% to about 0.70%, from about 0.20% to about 0.60%, from about 0.20% to about 0.50%, or from about 0.20% to about 0.45% Avicel hydrolysis per µg cellobiohydrolase per 48 hours based on an initial 1% Avicel concentration. In some embodiments, the host cell comprises a heterologous cellobiohydrolase that has a specific activity of from about 0.30% to about 0.90%, from about 0.30% to about 0.80%, from about 0.30% to about 0.70%, from about 0.30% to about 0.50%, or from about 0.30% to about 0.45% Avicel hydrolysis per µg cellobiohydrolase per 48 hours, based on an initial 1% Avicel concentration. In some embodiments, the host cell comprises a heterologous cellobiohydrolase that has a specific activity of from about 0.40% to about 0.90%, from about 0.40% to about 0.80%, from about 0.40% to about 0.70%, from about 0.40% to about 0.50%, or from about 0.40% to about 0.45% Avicel hydrolysis per µg cellobiohydrolase per 48 hours, based on an initial 1% Avicel concentration.

In some embodiments, the host cell comprises a heterologous cellobiohydrolase that has a specific activity on Avicel of at least about 0.08 µmol/mg/min, at least about 0.09 µmol/mg/min, at least about 0.10 µmol/mg/min, at least about 0.11 µmol/mg/min, at least about 0.12 µmol/mg/min, at least about 0.13 µmol/mg/min, at least about 0.14 µmol/mg/min, at least about 0.15 µmol/mg/min, or at least about 0.16 µmol/mg/min. In some embodiments, the host cell comprises a heterologous cellobiohydrolase that has a specific activity on Avicel from about 0.08 µmol/mg/min to about 0.30 µmol/mg/min, from about 0.08 µmol/mg/min to about 0.25 µmol/mg/min, or from about 0.08 µmol/mg/min to about 0.20 µmol/mg/min. In some embodiments, the host cell comprises a heterologous cellobiohydrolase that has a specific activity on Avicel from about 0.10 µmol/mg/min to about 0.30 µmol/mg/min, from about 0.10 µmol/mg/min to about 0.25 µmol/mg/min, or from about 0.10 µmol/mg/min to about 0.20 µmol/mg/min. In some embodiments, the host cell comprises a heterologous cellobiohydrolase that has a specific activity on Avicel from about 0.15 µmol/mg/min to about 0.30 µmol/mg/min, from about 0.15 µmol/mg/min to about 0.25 µmol/mg/min, or from about 0.15 µmol/mg/min to about 0.20 µmol/mg/min.

In additional embodiments, the transformed host cells or cell cultures are assayed for ethanol production. Ethanol production can be measured by techniques known to one or ordinary skill in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein.

Co-Cultures

The present invention is also directed to co-cultures comprising at least two yeast host cells wherein the at least one yeast host cell comprises a polynucleotide encoding a *Cochliobolus heterostrophus, Gibberella zeae, Irpex lacteus, Volvariella volvacea*, or *Piromyces* sp. Cbh2 polypeptide and at least one other yeast host cell comprises a polynucleotide encoding a heterologous cellulase. As used herein, "co-culture" refers to growing two different strains or species of host cells together in the same vessel. In some embodiments of the invention, at least one host cell of the co-culture comprises a heterologous polynucleotide comprising a nucleic acid which encodes an endoglucanase, at least one host cell of the co-culture comprises a heterologous polynucleotide comprising a nucleic acid which encodes a β-glucosidase and at least one host cell comprises a heterologous polynucleotide comprising a nucleic acid which encodes a *Cochliobolus heterostrophus, Gibberella zeae, Irpex lacteus, Volvariella volvacea*, or *Piromyces* sp. Cbh2 polypeptide. In a further embodiment, the co-culture further comprises a host cell comprising a heterologous polynucleotide comprising a nucleic acid which encodes a second cellobiohydrolase.

The co-culture can comprise two or more strains of yeast host cells and the heterologous cellulases can be expressed in any combination in the two or more strains of host cells. For example, according to the present invention, the co-culture can comprise two strains: one strain of host cells that expresses an endoglucanase and a second strain of host cells that expresses a β-glucosidase, a *Cochliobolus heterostrophus, Gibberella zeae, Irpex lacteus, Volvariella volvacea*, or *Piromyces* sp. Cbh2 polypeptide and a second cellobiohydrolase. According to the present invention, the co-culture can also comprise four strains: one strain of host cells which expresses an endoglucanase, one strain of host cells that expresses a β-glucosidase, one strain of host cells which expresses a *Cochliobolus heterostrophus, Gibberella zeae, Irpex lacteus, Volvariella volvacea*, or *Piromyces* sp. Cbh2 polypeptide, and one strain of host cells which expresses a second cellobiohydrolase. Similarly, the co-culture can comprise one strain of host cells that expresses two cellulases, for example an endoglucanase and a beta-glucosidase and a second strain of host cells that expresses one or more cellobiohydrolases including one *Cochliobolus heterostrophus, Gibberella zeae, Irpex lacteus, Volvariella volvacea*, or *Piromyces* sp. Cbh2 polypeptide. The co-culture can, in addition to the at least one yeast host cell comprising a polynucleotide encoding a *Cochliobolus heterostrophus, Gibberella zeae, Irpex lacteus, Volvariella volvacea,* or *Piromyces* sp. Cbh2 polypeptide and at least one other yeast host cell comprising a polynucleotide encoding a heterologous cellulase, also include other host cells which do not comprise heterologous cellulases.

The various host cell strains in the co-culture can be present in equal numbers, or one strain or species of host cell can significantly outnumber another second strain or species of host cells. For example, in a co-culture comprising two strains or species of host cells the ratio of one host cell to another can be about 1:1, 1:2, 1:3, 1:4, 1:5, 1:10, 1:100, 1:500 or 1:1000. Similarly, in a co-culture comprising three or more strains or species of host cells, the strains or species of host cells can be present in equal or unequal numbers.

The co-cultures of the present invention can include tethered cellulases, secreted cellulases or both tethered and secreted cellulases. For example, in some embodiments of the invention, the co-culture comprises at least one yeast host cell comprising a polynucleotide encoding a secreted *Cochliobolus heterostrophus, Gibberella zeae, Irpex lacteus, Volvariella volvacea,* or *Piromyces* sp. Cbh2 polypeptide. In another embodiment, the co-culture comprises at least one yeast host cell comprising a polynucleotide encoding a tethered *Cochliobolus heterostrophus, Gibberella zeae, Irpex lacteus, Volvariella volvacea,* or *Piromyces* sp. Cbh2 polypeptide. In one embodiment, all of the heterologous cellulases in the co-culture are secreted, and in another embodiment, all of the heterologous cellulases in the co-culture are tethered. In addition, other cellulases, such as externally added cellulases can be present in the co-culture.

According to the methods described herein, a host cell or group of host cells can comprise a vector or vectors which encode and express a combination of heterologous cellulases including a cellulase selected from the group consisting of *Cochliobolus heterostrophus, Gibberella zeae, Irpex lacteus, Volvariella volvacea,* and *Piromyces* sp. Cbh2. For example, a single host cell may express *C. formosanus* endoglucanase I, *S. fibuligera* β-glucosidase I, *T. emersonii* Cbh1, and a Cbh2 selected from the group consisting of *Cochliobolus heterostrophus* C4 cel7; *Gibberella zeae* K59 cel6; *Irpex lacteus* MC-2 cex3; *Volvariella volvacea* cbhII-I; and *Piromyces* sp. E2 cel6A. Alternatively, a group of cells could express a combination of cellulases, for example such that a first host cell expresses *C. formosanus* endoglucanase I, a second host cell expresses *S. fibuligera* β-glucosidase I, a third host cell expresses *T. emersonii* Cbh1, and a fourth host cell expresses a Cbh2 selected from the group consisting of *Cochliobolus heterostrophus* C4 cel7; *Gibberella zeae* K59 cel6; *Irpex lacteus* MC-2 cex3; *Volvariella volvacea* cbhII-I; and *Piromyces* sp. E2 cel6A. Similarly, a first host cell can express both *C. formosanus* endoglucanase I and *S. fibuligera* β-glucosidase I and a second host cell can express both *T. emersonii* Cbh1, and a Cbh2 selected from the group consisting of *Cochliobolus heterostrophus* C4 cel7; *Gibberella zeae* K59 cel6; *Irpex lacteus* MC-2 cex3; *Volvariella volvacea* cbhII-I; and *Piromyces* sp. E2 cel6A. In another embodiment, a single host cell or group of host cells may express *T. reesi* endoglucanase I, *S. fibuligera* β-glucosidase I, *T. emersonii* Cbh1, and a Cbh2 selected from the group consisting of *Cochliobolus heterostrophus* C4 cel7; *Gibberella zeae* K59 cel6; *Irpex lacteus* MC-2 cex3; *Volvariella volvacea* cbhII-1; and *Piromyces* sp. E2 cel6A.

EXAMPLES

Materials and Methods

Media and Strain Cultivation

*Escherichia coli* strain DH5a (Invitrogen), or NEB 5 alpha (New England Biolabs) was used for plasmid transformation and propagation. Cells were grown in LB medium (5 g/L yeast extract, 5 g/L NaCl, 10 g/L tryptone) supplemented with ampicillin (100 mg/L), kanamycin (50 mg/L), or zeocin (20 mg/L). When zeocin selection was desired LB was adjusted to pH 7.0. Also, 15 g/L agar was added when solid media was desired.

Yeast strains were routinely grown in YPD (10 g/L yeast extract, 20 g/L peptone, 20 g/L glucose), YPC (10 g/L yeast extract, 20 g/L peptone, 20 g/L cellobiose), or YNB+glucose (6.7 g/L Yeast Nitrogen Base without amino acids, and supplemented with appropriate amino acids for strain, 20 g/L glucose) media with either G418 (250 mg/L unless specified) or zeocin (200 mg/L unless specified) for selection. 15 g/L agar was added for solid media.

Molecular Methods

Standard protocols were followed for DNA manipulations (Sambrook et al. 1989). PCR was performed using Phusion polymerase (New England Biolabs) for cloning, and Taq polymerase (New England Biolabs) for screening transformants, and in some cases Advantage Polymerase (Clontech) for PCR of genes for correcting auxotrophies. Manufacturers guidelines were followed as supplied. Restriction enzymes were purchased from New Englad Biolabs and digests were set up according to the supplied guidelines. Ligations were performed using the Quick ligation kit (New England Biolabs) as specified by the manufacturer. Gel purification was performed using either Qiagen or Zymo research kits, PCR product and digest purifications were performed using Zymo research kits, and Qiagen midi and miniprep kits were used for purification of plasmid DNA.

Yeast Transformation

A protocol for electrotransformation of yeast was developed based on Cho, K. M.; Yoo, Y. J. and Kang, H. S., *Enzyme And Microbial Technology,* 25: 23-30, (1999) and Ausubel, F. M., et al., Current Protocols in Molecular Biology. USA: John Wiley and Sons, Inc. (1994). Linear fragments of DNA are created by restriction enzyme digestion utilizing unique restriction sites within the plasmid. The fragments are purified by precipitation with 3M sodium acetate and ice cold ethanol, subsequent washing with 70% ethanol, and resuspension in USB dH2O (DNAse and RNAse free, sterile water) after drying in a 70° C. vacuum oven.

Yeast cells, e.g., *Saccharomyces cerevisiae,* for transformation are prepared by growing to saturation in 5 mL YPD cultures. 4 mL of the culture is sampled, washed 2× with cold distilled water, and resuspended in 640 μL cold distilled water. 80 μL, of 100 mM Tris-HCl, 10 mM EDTA, pH 7.5 (10× TE buffer—filter sterilized) and 80 μL of 1M lithium acetate, pH 7.5 (10× liAc—filter sterilized) is added and the cell suspension is incubated at 30° C. for 45 minutes with gentle shaking. 20 μl, of 1M DTT is added and incubation continues for 15 minutes. The cells are then centrifuged, washed once with cold distilled water, and once with electroporation buffer (1M sorbitol, 20 mM HEPES), and finally resuspended in 267 μL electroporation buffer.

For electroporation, 10 μg of linearized DNA (measured by estimation on gel) is combined with 50 μL of the cell suspension in a sterile 1.5 mL microcentrifuge tube. The mixture is then transferred to a 0.2 cm electroporation cuvette, and a pulse of 1.4 kV (200Ω, 25 µF) is applied to the sample using, e.g., the Biorad Gene Pulser device. 1 mL of YPD with 1M sorbitol adjusted to pH 7.0 (YPDS) is placed in the cuvette and the cells are allowed to recover for ~3 hrs. 100-200 µL cell suspension are spread out on YPDS agar plates with appropriate selection, which are incubated at 30° C. for 3-4 days until colonies appear.

SDS-PAGE and Gel Staining

SDS-PAGE (sodium dodecyl sulfate polyacrylamide gel electrophoresis) was carried out as described by Laemmli (Nature 227: 680-685 (1970)) on a 10% gel at 100 V. A 20 µl sample of culture supernatant was mixed with SDS-PAGE loading buffer and incubated at 95° C. for 5 minutes before loading onto the gel. After protein separation, the gels were silver stained. Silver staining was performed by incubating the gels with shaking at room temperature in 1) 30% ethanol and 0.5% acetic acid (3×30 min); 2) 20% ethanol (10 min); 3) water (10 min); 4) sodium thiosulfate (0.2 g/L) (1 min); 5) water (2×20 seconds); 6) silver nitrate (2 g/L) (30 min); 7) water (5-10 seconds); 8) 37% formaldehyde (0.7 ml/L) and potassium carbonate (anhydr.) (30 g/L) and sodium thiosulfate (10 mg/L) (2×3 min or to desired intensity); 9) Tris base (50 g/L) and 2.5% acetic acid (1 min); and 10) water.

Determination of Protein Concentration

To estimate specific activity of the Cbh2s the Bradford method (BioRad protein assay) was used as it is prescribed for use in microtiter plates, using the Gamma globulin standard. Before determination of protein concentration, supernatant samples were first subjected to the buffer exchange procedure as directed for the 2 mL Zeba desalt spin columns (Thermo Scientific).

Measurement of Cellulase Activity

An Avicel conversion assay was used to measure the cellulolytic activity of yeast strains expressing CBHs. 2% Avicel cellulose in 50 mM Na-acetate, pH 5.0 is suspended and mixed well to make the suspension homogenous. The homogenous suspension is pipetted to the tubes (0.5 ml each). 0.5 ml of sample is added to each tube on the substrate. The samples can be: enzyme in buffer, yeast culture filtrate, inactivated yeast culture filtrate (to detect the background sugars from cultivation media) or buffer for blank. The tubes are incubated at 35° C. with shaking (1000 rpm). The samples (100 µl) are then removed after a predetermined hydrolysis time, e.g., 0 h, 4 h, 24 h and 48 h, into separate tubes and spun down. 50 µl of supernatant is added to 100 µl of DNS reagent into a microplate. This mixture is then heated at 99° C. for 5 minutes. The absorbance is measured at 595 nm. The glucose equivalent formed (reducing sugars) is analyzed using DNS calibration by glucose standard.

The Dinitrosalicylic Acid Reagent Solution (DNS), 1% includes the following 3,5-dinitrosalicylic acid: 10 g; Sodium sulfite: 0.5 g; Sodium hydroxide: 10 g; water to 1 liter. The DNS is calibrated by glucose (using glucose samples with conc. 0, 1, 2, 3, 4, 5 and 6 g/l, the slope [S] is calculated, for DNS from May 8, 2007 S=0.0669). The DNS solution can be stored at 4° C. for several months.

Example 1

Cloning of Codon-Optimized Cbh2 Genes and their Expression in Saccharomyces cerevisiae Cellobiohydrolase (cbh) genes from five fungal organisms (as indicated in Table 8 below) were selected for expression in yeast. The sequences were first codon-optimized for expression in Saccharomyces cerevisiae.

The software available on the website of the University of Maryland, Baltimore County applying the CAI codon usage table suggested by Carbone et al. 2003 was utilized to generate an initial sequence that had a codon adaptation index (CAI) of 1.0, where three-letter sequences encoding for individual amino acid codons were replaced with those three-letter sequences known to be most frequently used in S. cerevisiae for the corresponding amino acid codons. The initial codon-optimized sequence generated by this software was then further modified. In particular, the software was utilized to identify certain stretches of sequence (e.g., sequences with 4, 5, 6, 7, 8, 9, or 10 contiguous A's or T's), and replace these sequences with three-letter sequences corresponding to the second most frequently utilized three-letter sequences in S. cerevisiae. In addition, for molecular cloning purposes, the website software was used to similarly replace certain restriction enzyme, including PacI, AscI, BamHI, BglII, EcoRI and XhoI. Finally other DNA software (DNAman) was used to check the DNA sequence for direct repeats, inverted repeats and mirror repeats with lengths of 10 bases or longer. These sequences were modified by manually replacing codons with "second best" codons . . . .

(SEQ ID NO: 21)

```
agctgtttcctgtgtgaaattgttatccgctcacaattccacacaacatacgagccggaagcataaagtgtaaagcctggggtgcct aatgagtgaggtaactcacattaattgcgttgcgctcactgcccgctttccagtcgggaaacctgtcgtgccagctggattaatgaat cggccaacgcgcggggagaggcggtttgcgtattgggcgctcttccgcttcctcgctcactgactcgctgcgctcggtcgttcgg ctgcggcgagcggtatcagctcactcaaaggcggtaatacggttatccacagaatcagggggataacgcaggaaagaacatgtga gcaaaaggccagcaaaaggccaggaaccgtaaaaaggccgcgttgctggcgtttttccataggctccgcccccctgacgagcat cacaaaaatcgacgctcaagtcagaggtggcgaaacccgacaggactataaagataccaggcgtttccccctggaagctccctc gtgcgctctcctgttccgaccctgccgcttaccggatacctgtccgcctttctcccttcgggaagcgtggcgctttctcaatgctcac gctgtaggtatctcagttcggtgtaggtcgttcgctccaagctgggctgtgtgcacgaaccccccgttcagcccgaccgctgcgcc ttatccggtaactatcgtcttgagtccaacccggtaagacacgacttatcgccactggcagcagccactggtaacaggattagcag agcgaggtatgtaggcggtgctacagagttcttgaagtggtggcctaactacggctacactagaaggacagtatttggtatctgcg ctctgctgaagccagttaccttcggaaaaagagttggtagctcttgatccggcaaacaaaccaccgctggtagcggtggttttttgtt tgcaagcagcagattacgcgcagaaaaaaaggatctcaagaagatcctttgatcttttctacggggtctgacgctcagtggaacga
```

-continued

```
aaactcacgttaagggattttggtcatgagattatcaaaaaggatcttcacctagatccttttaaattaaaaatgaagtttaaatcaatct aaagtatatatgagtaaacttggtctgacagttaccaatgataatcagtgaggcacctatctcagcgatctgtctatttcgttcatccat agttgcctgactccccgtcgtgtagataactacgatacgggagggcttaccatctggccccagtgctgcaatgataccgcgagacc cacgctcaccggctccagatttatcagcaataaaccagccagccggaagggccgagcgcagaagtggtcctgcaactttatccg cctccatccagtctattaattgttgccgggaagctagagtaagtagttcgccagttaatagtttgcgcaacgttgttgccattgctacag gcatcgtggtgtcacgctcgtcgtttggtatggcttcattcagctccggttcccaacgatcaaggcgagttacatgatccccatgttg tgcaaaaaagcggttagctccttcggtcctccgatcgttgtcagaagtaagttggccgcagtgttatcactcatggttatggcagcac tgcataattctcttactgtcatgccatccgtaagatgcttttctgtgactggtgagtactcaaccaagtcattctgagaatagtgtatgcg gcgaccgagttgctcttgcccggcgtcaatacgggataataccgcgccacatagcagaactttaaaagtgctcatcattggaaaac gttcttcggggcgaaaactctcaaggatcttaccgctgttgagatccagttcgatgtaacccactcgtgcacccaactgatcttcagc atcttttactttcaccagcgtttctgggtgagcaaaaacaggaaggcaaaatgccgcaaaaaagggaataagggcgacacggaaa tgttgaatactcatactcttccttttttcaatattattgaagcatttatcaggttattgtctcatgagcggatacatatttgaatgtatttagaa aaataaacaaatagggggttccgcgcacatttccccgaaaagtgccacctgacgtctaagaaaccattattatcatgacattaacctat aaaaataggcgtatcacgaggccctttcgtctcgcgcgtttcggtgatgacggtgaaaacctctgacacatgcagctcccggagac ggtcacagcttgtctgtaagcggatgccgggagcagacaagcccgtcagggcgcgtcagcgggtgttggcgggtgtcgggct ggcttaactatgcggcatcagagcagattgtactgagagtgcaccataacgcatttaagcataaacacgcactatgccgttatctca tgtatatatatatacaggcaacacgcagatataggtgcgacgtgaacagtgagctgtatgtgcgcagctcgcgttgcattttcggaa gcgctcgtatcggaaacgctttgaagttcctattccgaagttcctattctctagctagaaagtataggaacttcagagcgcttttgaaa accaaaagcgctctgaagacgcacttcaaaaaaccaaaaacgcaccggactgtaacgagctactaaaatattgcgaataccgctt ccacaaacattgctcaaaagtatctctttgctatatatctctgtgctatatccctatataacctacccatccacctttcgctccttgaacttg catctaaactcgacctctacattttttatgtttatctctagtattactcttagacaaaaaaattgtagtaagaactattcatagagtgaatc gaaaacaatacgaaaatgtaaacatttcctatacgtagtatatagagacaaaatagaagaaaccgttcataattttctgaccaatgaa gaatcatcaacgctatcactttctgttcacaaagtatgcgcaatccacatcggtatagaatataatcggggatgcctttatcttgaaaaa atgcacccgcagatcgctagtaatcagtaaacgcgggaagtggagtcaggctttttttatggaagagaaaatagacaccaaagta gccttcttctaaccttaacggacctacagtgcaaaaagttatcaagagactgcattatagagcgcacaaaggagaaaaaaagtaat ctaagatgattgttagaaaaatagcgctctcgggatgcattttgtagaacaaaaagaagtatagattctttgttggtaaaatagcgc tctcgcgttgcatttctgttctgtaaaaatgcagctcagattctttgtttgaaaaattagcgctctcgcgttgcatttttgttttacaaaaatg aagcacagattatcgttggtaaaatagcgctttcgcgttgcatttctgttctgtaaaaatgcagctcagattctttgtttgaaaaattagc gctctcgcgttgcattttgttctacaaaatgaagcacagatgcttcgttaacaaagatatgctattgaagtgcaagatggaaacgcag aaaatgaaccggggatgcgacgtgcaagattacctatgcaatagatgcaatagtttctccaggaaccgaaatacatacattgtcttc cgtaaagcgctagactatatattattatacaggttcaaatatactatctgtttcagggaaaactcccaggttcggatgttcaaaattcaat gatgggtaacaagagcttttcaattcatcatttttttttattcttttttttgatttcggtttctttgaaattttttttgattcggtaatctccgaacag aaggaagaacgaaggaaggagcacagacttagattggtatatatacgcatatgtagtgttgaagaaacatgaaattgcccagtatt cttaacccaactgcacagaacaaaaaccgaaacgaagataaatcatgtcgaaagctacatataaggaacgtgctgctactcatcct agtcctgttgctgccaagctatttaatatcatgcacgaaaagcaaacaaacttgtgtgatcattggatgttcgtaccaccaaggaatt actggagttagttgaagcattaggtcccaaaatttgtttactaaaaacacatgtggatatcttgactgatttttccatggagggcacagt taagccgctaaaggcattatccgccaagtacaatttttttactcttcgaagacagaaaatttgctgacattggtaatacagtcaaattgca gtactctgcgggtgtatacagaatagcagaatgggcagacattacgaatgcacacggtgtggtgggcccaggtattgttagcggtt tgaagcaggcggcagaagaagtaacaaaggaacctagaggccttttgatgttagcagaattgtcatgcaagggctccctatctact ggagaatatactaagggtactgttgacattgcgaagagcgacaaagattttgttatcggctttattgctcaaagagacatgggtgaa
```

-continued

```
gagatgaaggttacgattggttgattatgacacccggtgtgggtttagatgacaagggagacgcattgggtcaacagtatagaacc gtggatgatgtggtctctacaggatctgacattattattgttggaagaggactatttgcaaagggaagggatgctaaggtagaggt gaacgttacagaaaagcaggctgggaagcatatttgagaagatgcggccagcaaaactaaaaaactgtattataagtaaatgcat gtatactaaactcacaaattagagcttcaatttaattatatcagttattaccctatgcggtgtgaaataccgcacagatgcgtaaggag aaaataccgcatcaggcgccattcgccattcaggctgcgcaactgttgggaagggcgatcggtgcgggcctcttcgctattacgc cagctggcgaagggggatgtgctgcaaggcgattaagttgggtaacgccagggttttcccagtcacgacgttgtaaaacgacg gccagtgccaagctttctaactgatctatcc aaaactgaaaattacattatgattaggtttatcacaggcaaatgtaatttgtggtatttt gccgttcaaaatctgtagaattttctcattggtcacattacaacctgaaaatactttatctacaatcataccattatataacatgtcccctt aatactaggatcaggcatgaacgcatcacagacaaaatcttcttgacaaacgtcacaattgatccctccccatccgttatcacaatga caggtgtcattttgtgctcttatgggacgatccttattaccgctttcatccggtgatagaccgccacagaggggcagagagcaatcat cacctgcaaaccttctatacactcacatctaccagtgtacgaattgcattcagaaaactgtttgcattcaaaaataggtagcatacaa ttaaaacatggcgggcacgtatcattgccatatcttgtgcagttagacgcgaattttttcgaagaagtaccttcaaagaatggggtctc atcttgttttgcaagtaccactgagcaggataataatagaaatgataatatactatagtagagataacgtcgatgacttcccatactgta attgcttttagttgtgtatttttagtgtgcaagtttctgtaaatcgattaattttttttcttcctcttttttattaaccttaattttttatttagattcct gacttcaactcaagacgcacagatattataacatctgcacaataggcatttgcaagaattactcgtgagtaaggaaagagtgagga actatcgcatacctgcatttaaagatgccgatttgggcgcgaatccttttattttggatcaccctcatactattatcagggccagaaaaa ggaagtgtttccctccttcttgaattgatgttaccctc ataaagcacgtggcctcttatcgagaaagaaattaccgtcgctcgtgatttgt ttgcaaaagaacaaaactgaaaaaacccagacacgctcgacttcctgtatcctattgattgcagcttccaatttcgtcacacaaca aggtcctagcgacggctcacaggttttgtaacaagcaatcgaaggttctggaatggcgggaaagggtttagtaccacatgctatga tgcccactgtgatctccagagcaaagttcgttcgatcgtactgttactctctctctttcaaacagaattgtccgaatcgtgtgacaacaa cagcctgttctcacacactattcttctaaccaagggggtggtttagtttagtagaacctcgtgaaacttacatttacatatatataaact tgcataaattggtcaatgcaagaaatacatatttggtcttttctaattcgtagtttttcaagttcttagatgctttcttttttctcttttttacagat catcaaggaagtaattatctacttttttacaacaaatataaaacttaattaaacaatggccaagaagttgttcattaccgctgccttagctg ccgcagtgcttgctgcaccagtgatcgaagagagacaaaattgcggagccgtctggacacagtgcggaggcaacggctggcaa ggcccaacatgttgtgcttctggctcaacgtgcgtggcacagaacgagtggtattcccagtgccttccaaactcccaggtgacttctt caacaaccccagctcaacgtctacttcacagagatccacaagtacctatctagcacaaccagaagtggctcatcctcatctagca gtacgacccctccacccgtatcaagtcctgtcacgagtatccctggcggagcaacctcaacagccagttattccggcaatcctttct ctggagtgagattatttgcaaacgactattatagatcagaggttcacaaccttgcaattccttctatgacgggaaccctagccgcaaa ggatccgccgtagcagaagtccctagtttccaatggcttgacagaaacgttacaatagatacacttatggtacagactttatctcag gttagagctttgaataaggccggtgccaacccaccttatgctgcccaattagtagtctatgacttgccagatagagactgtgctgccg cagcttctaatggtgaattttccatcgcaaatggcggagctgcaaactatagatcatacattgatgcaataagaaaacacatcattga gtattctgatattagaataatccttgtgattgaaccagactccatggctaatatggttaccaacatgaatgtagccaagtgttctaacgc agatccacataccatgagctaaccgtatatgcattaaaacaactgaatctacctaacgttgctatgtacttagatgccggtcatgccg gatggttgggctggcctgcaaatatccaacccgcagctgaattgttcgctggaatctacaacgacgccggaaagcccgctgccgt tagaggcttagccacaaatgttgcaaattacaacgcttggtcaattgctagtgcccatcttatacctcaccaaatcctaactacgatg agaaacattacatgaagcattttcccccattgttaaactccgctggattcctgccagattcatcgtggataccggtagaaacggcaa acaaccaactggacaacaacaatggggagattggtgtaacgtcaagggaaccggcttcggcgtcaggcctacggcaaacaccg gacacgagctagtcgacgcttttgtatgggttaagccaggtggcgaaagtgacgaacaagtgacacgagtgctgcaagatacg attaccactgtggtctgtccgacgctttacagcccgccccgaggctggacaatggttccaggcttattttgaacaattgttaacgaa cgcaaatccaccattctaaggcgcgccgaattcgagagactcgagactgaatcggatcgatcccgggcccgtcgagggatctgc gatagatcaattttttcttttctctttccccatcctttacgctaaaataatagtttatttttatttttgaatatttttttatttatacgtatatataga
```

-continued

```
ctattatttatcttttaatgattattaagattttttattaaaaaaaattcgctcctctataatgcctttatgcagttttttttcccattcgatatttc
tatgttcgggttcagcgtattttaagtttaataactcgaaaattctgcgttcgttaaagcttgcatgcctgcaggtcgactctagaggatc
cccgggtaccgagctcgaattaattcgtaatcatggtcat.
```

The resulting plasmids are summarized below in Tables 8 and 9.

TABLE 8

Cbh2 plasmid descriptions.

| Organism & Gene: | Expression plasmid: | Theoretical enzyme size Da* |
|---|---|---|
| Cochliobolus heterostrophus C4 cel7 | pRDH150 | 41647.29 |
| Gibberella zeae K59 cel6 | pRDH151 | 49032.64 |

TABLE 8-continued

Cbh2 plasmid descriptions.

| Organism & Gene: | Expression plasmid: | Theoretical enzyme size Da* |
|---|---|---|
| Irpex lacteus MC-2 cex3 | pRDH152 | 47388.73 |
| Volvariella volvacea cbhII-I | pRDH153 | 46981.60 |
| Piromyces sp. E2 cel6A | pRDH154 | 53914.95 |

TABLE 9

Cbh2 plasmid sequences.

```
pRDH150
agctgtttcctgtgtgaaattgttatccgctcacaattccacacaacatacgagccggaagcataaagtgtaaagcctggggtgcctaatgagt
gaggtaactcacattaattgcgttgcgctcactgcccgctttccagtcgggaaacctgtcgtgccagctggattaatgaatcggccaacgcgc
ggggagaggcggtttgcgtattgggcgctcttccgcttcctcgctcactgactcgctgcgctcggtcgttcggctgcggcgagcggtatcag
ctcactcaaaggcggtaatacggttatccacagaatcaggggataacgcaggaaagaacatgtgagcaaaaggccagcaaaaggccagg
aaccgtaaaaaggccgcgttgctggcgtttttccataggctccgcccccctgacgagcatcacaaaaatcgacgctcaagtcagaggtggc
gaaacccgacaggactataaagataccaggcgtttccccctggaagctccctcgtgcgctctcctgttccgaccctgccgcttaccggatac
ctgtccgcctttctccctccggaagcgtggcgctttctcaatgctcacgctgtaggtatctcagttcggtgtaggtcgttcgctccaagctggg
ctgtgtgcacgaaccccccgttcagcccgaccgctgcgccttatccggtaactatcgtcttgagtccaacccggtaagacacgacttatcgcc
actggcagcagccactggtaacaggattagcagagcgaggtatgtaggcggtgctacagagttcttgaagtggtggcctaactacggctac
actagaaggacagtatttggtatctgcgctctgctgaagccagttaccttcggaaaaagagttggtagctcttgatccggcaaacaaaccacc
gctggtagcggtggtttttttgttgcaagcagcagattacgcgcagaaaaaaaggatctcaagaagatcctttgatatttctacgggggtctga
cgctcagtggaacgaaaactcacgttaagggattttggtcatgagattatcaaaaaggatcttcacctagatccttttaaattaaaaatgaagtttt
aaatcaatctaaagtatatatgagtaaacttggtctgacagttaccaatgcttaatcagtgaggcacctatctcagcgatctgtctatttcgttcatc
catagttgcctgactccccgtcgtgtagataactacgatacgggagggcttaccatctggccccagtgctgcaatgataccgcgagacccac
gctcaccggctccagatttatcagcaataaaccagccagccggaagggccgagcgcagaagtggtcctgcaactttatccgcctccatcca
gtctattaattgttgccgggaagctagagtaagtagttcgccagttaatagtttgcgcaacgttgttgccattgctacaggcatcgtggtgtcac
gctcgtcgtttggtatggcttcattcagctccggttcccaacgatcaaggcgagttacatgatccccatgttgtgcaaaaaagcggttagctc
cttcggtcctccgatcgttgtcagaagtaagttggccgcagtgttatcactcatggttatggcagcactgcataattctcttactgtcatgccatcc
gtaagatgcttttctgtgactggtgagtactcaaccaagtcattctgagaatagtgtatgcggcgaccgagttgctcttgcccggcgtcaatac
gggataataccgcgccacatagcagaactttaaaagtgctcatcattggaaaacgttcttcggggcgaaaactctcaaggatcttaccgctgtt
gagatccagttcgatgtaacccactcgtgcacccaactgatcttcagcatcttttactttcaccagcgtttctgggtgagcaaaaacaggaagg
caaaatgccgcaaaaaagggaataagggcgacacggaaatgttgaatactcatactcttcctttttcaatattattgaagcatttatcagggttat
tgtctcatgagcggatacatatttgaatgtatttagaaaaataaacaaataggggttccgcgcacatttccccgaaaagtgccacctgacgtcta
agaaaccattattatcatgacattaacctataaaaataggcgtatcacgaggccctttcgtctcgcgcgtttcggtgatgacggtgaaaacctct
gacacatgcagaccccggagacggtcacagcttgtctgtaagcggatgccgggagcagacaagcccgtcagggcgcgtcagcgggtgtt
ggcgggtgtcggggctggcttaactatgcggcatcagagcagattgtactgagagtgcaccataacgcatttaagcataaacacgcactatg
ccgttcttctcatgtatatatatacaggcaacacgcagatataggtgcgacgtgaacagtgagctgtatgtgcgcagctcgcgttgcattttc
ggaagcgctcgttttcggaaacgctttgaagttcctattccgaagttcctattctctagctagaaagtataggaacttcagagcgcttttgaaaac
caaaagcgctctgaagacgcactttcaaaaaaccaaaaacgcaccggactgtaacgagctactaaaatattgcgaataccgcttccacaaa
cattgctcaaaagtatctctttgctatatatctctgtgctatatccctatataacctacccatccacctttcgctccttgaacttgcatctaaactcgac
ctctacattttttatgtttatctctagtattactctttagacaaaaaaattgtagtaagaactattcatagagtgaatcgaaaacaatacgaaaatgta
aacatttcctatacgtagtatatagagacaaagaaagaaaccgttcataattttctgaccaatgaagaatcatcaacgctatcactttctgttca
caaagtatgcgcaatccacatcggtatagaatataatcggggatgcctttatcttgaaaaaatgcacccgcagctcgctagtaatcagtaaac
gcgggaagtggagtcaggctttttttatggaagagaaaatagacaccaaagtagccttcttctaacctaacggacctacagtgcaaaaagtt
atcaagagactgcattatagagcgcacaaaggagaaaaaagtaatctaagatgctttgttagaaaaatagcgctctcgggatgcatttttgta
gaacaaaaaagaagtatagattctttggttggtaaaatagcgctctcgcgttgcatttctgttctgtaaaaatgcagctcagattctttgtttgaaaaa
ttagcgctctcgcgttgcattttttgttttacaaaaatgaagcacagattcttcgttggtaaaatagcgctttcgcgttgcatttctgttctgtaaaaat
gcagctcagattctttgtttgaaaaattagcgctctcgcgttgcattttgttctacaaaatgaagcacagatgcttcgttaacaaagatatgctatt
gaagtgcaagatggaaacgcagaaaatgaaccggggatgcgacgtgcaagattacctatgcaatagatgcaatagtttctccaggaaccg
aaatacatacattgtcttccgtaaagcgctagactatatattattacaggtcaaatatactatctgtttcagggaaaatcccaggttcggatgt
tcaaaattcaatgatgggtaacaagagctttcaattcatcatttttttttattctttttttttgatttcggtttctttgaaatttttttgattcggtaatc
tccgaacagaaggaagaacgaaggaaggagcacagacttagattggtatatatacgcatatgtagtgttgaagaaacatgaaattgcccagtattct
taacccaactgcacagaacaaaaaccgaaacgaagataaatcatgtcgaaagctacatataaggaacgtgctgctactcatcctagtcctgtt
gctgccaagctatttaatatcatgcacgaaaagcaaacaaacttgtgtgcttcattggatgttcgtaccaccaaggaattactggagttagttga
agcattaggtcccaaaattttgtttactaaaaaacacatgtggatatctttgcctgatttttcccatggagggccacagttaagcgctaaaggcattatc
cgccaagtacaatttttactcttcgaagacagaaaattgctgacattggtaatacagtcaaattgcagtactctgcgggtgtatacagaatagc
agaatgggcagacattacgaatgcacacggtgtggtgggcccaggtattgttagcgtttgaagcaggcggcagaagaagtaacaaagga
acctagaggcctttgatgttagcagaattgtcatgcaagggctccctatctactggagaatatactaagggtactgttgacattgcgaagagc
gacaaagattttgttatcggctttattgctcaaagagacatgggtggaagagtagaggttacgattggttgattatgacaccgtggtggttt
agatgacaagggagacgcattgggtcaacagtatagaaccgtggatgatggtctctacaggatctgacattattattgttggaagaggact
atttgcaaagggaagggatgctaaggtagagggtgaacgttacagaaaagcaggctgggaagcatatttgagaagatgcggccagcaaa
actaaaaaactgtattataagtaaatgcatgtatactaaactcacaaattagagcttcaatttaattatatcagttattaccctatgcggtgtgaaat
accgcacagatgcgtaaggagaaaataccgcatcaggcgccattcgccattcaggctgcgcaactgttgggaagggcgatcggtgcggg
```

TABLE 9-continued

Cbh2 plasmid sequences.

cctcttcgctattacgccagctggcgaaggggggatgtgctgcaaggcgattaagttgggtaacgccagggttttcccagtcacgacgttgt
aaaacgacggccagtgccaagctttctaactgatctatccaaaactgaaaattacattcttgattaggttttatcacaggcaaatgtaatttgtggt
attttgccgttcaaaatctgtagaattttctccattggtcacattacaacctgaaaatactttatctacaatcataccattcttataacatgtccccttaat
actaggatcaggcatgaacgcatcacagacaaaatcttcttgacaaacgtcacaattgatccctccccatccgttatcacaatgacaggtgtca
ttttgtgctcttatgggacgatccttattaccgctttcatccggtgatagaccgccacagagggcagagagcaatcatcacctgcaaacccttt
ctatacactcacatctaccagtgtacgaattgcattcagaaaactgtttgcattcaaaaataggtagcatacaattaaaacatggcgggcacgta
tcattgccctttatcttgtgcagttagacgcgaatttttcgaagaagtaccttcaaagaatggggtctcatcttgttttttgcaagtaccactgagcag
gataataatagaaatgataatatactatagtagagataacgtcgatgactttcccatactgtaattgcttttagttgtgtattttagtgtgcaagtttct
gtaaatcgattaattttttttttttctttcctctttttattaaccttaattttattttagattcctgacttcaactcaagacgcacagatattataacatctgc
acaataggcatttgcaagaattactcgtgagtaaggaaagagtgaggaactatcgcatacctgcatttaaagatgccgatttgggcgcgaatcctt
tattttggcttcaccctcatactattatcagggccagaaaaaggaagtgtttccctccttcttgaattgatgttaccctcataaagcacgtggcctc
ttatcgagaaagaaattaccgtcgctcgtgatttgtttgcaaaaagaacaaaactgaaaaaaacccagacacgctcgacttcctgtcttcctattg
attgcagcttccaatttcgtcacacaacaaggtcctagcgacggctcacaggttttgtaacaagcaatcgaaggttctggaatggcgggaaa
gggtttagtaccacatgctatgatgcccactgtgatctcagagcaaagttcgttcgatcgtactgttactctctctcttttcaaacagaattgtccg
aatcgtgtgacaacaacagcctgttctcacacactcttttctctcaaccaaggggagtgttttagtttagtagaacctcgtgaaacttacatttacat
atatataaacttgcataaattggtcaatgcaagaaatacatattttggtctttttctaattcgtagtttttcaagttcttagatgctttctttttctcttttttt
acagatcatcaaggaagtaattatctacttttttacaacaaatataaaactttaattaaAATGTTGTCTAACGTTTTTTTGACTG
CTGCTTTGGCTGCTGGTTTGGCTCAAGCTTTGCCACAAGCTACTCCAACTCCAACTGC
TGCTCCATCTGGTAATCCATTTGCTGGTAAGAATTTTTACGCTAACCCATATTATTCT
TCAGAAGTTCATACTTTGGCTATGCCATCTTTGCCAGCTTCATTGAAACCAGCTGCTA
CTGCTGTTGCTAAAGTTGGTTCTTTTGTTTGGATGGATACTATGGCTAAGTTCCATT
GATGGATACTTACTTGGCTGATATTAAAGCTAAAAATGCTGCTGGTGCTAATTTGAT
GGGTACTTTCGTTGTTTATGATTTGCCAGATAGAGATTGTACTTTTAGCTTCTAAT
GGTGAATTGAAAATTGATGAAGGTGGTGTTGAAAAATACAAGACACAATACATTGA
TAAGATTGCTGCTATTATCAAAAGTACCCAGATGTTAAGATTAATTTGGCTATTGA
ACCAGATTCTTTGGCTAATATGGTTACTAATATGGGTGTTCAAAAATGTTCTAGAGCT
GCTCCATATTACAAAGAATTGACTGCTTATGCTTTGAAAACTTTGAACTTGAACAAC
GTTGACATGTATATGGATGGTGGTCATGCTGGTTGGTTGGGTTGGGATGCTAATATT
GGTCCAACTGCTAAATTGTTTGCTGAAGTTTACAAAGCTGCTGGTTCTCCAAGAGGT
GTTAGAGGTATTGTTACAAACGTTTCTAATTACAACGCTTTGAGAGTTTCTTCTTGTC
CATCTATTACTCAAGGTAACAAGAATTGTGATGAAGAAAGATACATTAATGCTTTGG
CTCCATTGTTGAAAAATGAAGGTTTTCCAGCTCATTTTATTGTTGATCAAGGTAGATC
AGGTAAAGTTCCAACTAATCAACAAGAATGGGGTGATTGGTGTAATGTTTCTGGTGC
TGGTTTTGGTACTAGACCAACTACTAATACTGGTAATGCTTTGATTGATGCTATTGTT
TGGGTTAAACCAGGTGGTGAATCTGATGGTACTTCTGATACTTCTGCTGCAAGATAT
GATGCTCATTGTGGTAGAAATTCTGCTTTTAAACCAGCTCCAGAAGCTGGTACTTGG
TTTCAAGCTTACTTTGAAATGTTGTTGAAGAATGCTAATCCAGCTTTGGCATTATAAg
gcgcgccgaattcgagagactcgagactgaatcggatcgatcccgggcccgtcgagggatctgcgatagatcaattttttcttttctcttccc
catccttacgctaaaataatagtttatttttattttttgaatatttttatttatatacgtatatatatagactattattatctttaatgattattaagat
ttttattaaaaaaaaatcgctcctcttttaatgcctttatgcagttttttttttcccattcgatatttctatgttcgggttcagcgtattttaagtttaat
aactcgaaaattctgcgttcgttaaagcttgcatgcctgcaggtcgactctagaggatccccgggtaccgagctcgaattaattcgtaatcatggtcat
(SEQ ID NO: 37)

pRDH151
agctgtttcctgtgtgaaattgttatccgctcacaattccacacaacatacgagccggaagcataaagtgtaaagcctggggtgcctaatgagt
gagctaactcacattaattgcgttgcgctcactgcccgctttccagtcgggaaacctgtcgtgccagctggcattaatgaatcggccaacgcgc
ggggagaggcggtttgcgtattgggcgctcttccgcttcctcgctcactgactcgctgcgctcggtcgttcggctgcggcgagcggtatcag
ctcactcaaaggcggtaatacggttatccacagaatcaggggataacgcaggaaagaacatgtgagcaaaaggccagcaaaaggccagg
aaccgtaaaaaggccgcgttgctggcgtttttccataggctccgcccccctgacgagcatcacaaaaatcgacgctcaagtcagaggtggc
gaaacccgacaggactataaagataccaggcgtttccccctggaagctccctcgtgcgctctcctgttccgaccctgccgcttaccggatac
ctgtccgcctttctcccttcgggaagcgtggcgctttctcaatgctcacgctgtaggtatctcagttcggtgtaggtcgttcgctccaagctggg
ctgtgtgcacgaaccccccgttcagcccgaccgctgcgccttatccggtaactatcgtcttgagtccaacccggtaagacacgacttatcgcc
actggcagcagccactggtaacaggattagcagagcgaggtatgtaggcggtgctacagagttcttgaagtggtggcctaactacggctac
actagaaggacagtatttggtatctgcgctctgctgaagccagttaccttcggaaaaagagttggtagctcttgatccggcaaacaaaccacc
gctggtagcggtggtttttttgtttgcaagcagcagattacgcgcagaaaaaaaggatctcaagaagatcctttgatcttttctacggggtctga
cgctcagtggaacgaaaactcacgttaagggattttggtcatgagattatcaaaaaggatcttcacctagatccttttaaattaaaaatgaagttt
taaatcaatctaaagtatatatgagtaaacttggtctgacagttaccaatgcttaatcagtgaggcacctatctcagcgatctgtctatttcgttcatc
catagttgcctgactccccgtcgtgtagataactacgatacgggagggcttaccatctggccccagtgctgcaatgataccgcgagacccac
gctcaccggctccagatttatcagcaataaaccagccagccggaagggccgagcgcagaagtggtcctgcaactttatccgcctccatcca
gtctattaattgttgccgggaagctagagtaagtagttcgccagttaatagtttgcgcaacgttgttgccattgctacaggcatcgtggtgtcac
gctcgtcgtttggtatggcttcattcagctccggttcccaacgatcaaggcgagttacatgatcccccatgttgtgcaaaaaagcggttagctc
cttcggtcctccgatcgttgtcagaagtaagttggccgcagtgttatcactcatggttatggcagcactgcataattctcttactgtcatgccatcc
gtaagatgcttttctgtgactggtgagtactcaaccaagtcattctgagaatagtgtatgcggcgaccgagttgctcttgcccggcgtcaatac
gggataataccgcgccacatagcagaactttaaaagtgctcatcattggaaaacgttcttcggggcgaaaactctcaaggatcttaccgctgtt
gagatccagttcgatgtaacccactcgtgcacccaactgatcttcagcatcttttactttcaccagcgtttctgggtgagcaaaaacaggaagg
caaaatgccgcaaaaaagggaataagggcgacacggaaatgttgaatactcatactcttcctttttcaatattattgaagcatttatcagggttat
tgtctcatgagcggatacatatttgaatgtatttagaaaaataaacaaataggggttccgcgcacatttccccgaaaagtgccacctgacgtcta
agaaaccattattatcatgacattaacctataaaaataggcgtatcacgaggccctttcgtctcgcgcgtttcggtgatgacggtgaaaacctct
gacacatgcagctcccggagacggtcacagcttgtctgtaagcggatgccgggagcagacaagcccgtcagggcgcgtcagcgggtgtt
ggcgggtgtcggggctggcttaactatgcggcatcagagcagattgtactgagagtgcaccataacctttaagcataaacacgcactatg
ccgttcttctcatgtatatatatatacaggcaacacgcagatataggtgcgacgtgaacagtgagctgtatgtgcgcagctcgcgttgcatttttc
ggaagcgctcgttttcggaaacgctttgaagttcctattccgaagttcctattctctagctagaaagtataggaacttcagagcgcttttgaaaac
caaaagcgctctgaagacgcacttcaaaaaaccaaaaacgcaccggactgtaacgagctactaaaatattgcgaataccgcttccacaaa
cattgctcaaaagtatctctttgctatatatctctgtgctatatccctatataacctacccatccacctttcgctccttgaacttgcatctaaactcgac
ctctacattttttatgtttatcctagtattactcttagacaaaaaaattgtagtaagaactattcatagagtgaatcgaaaacaatacgaaaatgta
aacatttcctatacgtagtatatagagacaaaatagaagaaaccgttcataattttctgaccaatgaagaatcatcaacgctatcactttctgttca
caaagtatgcgcaatccacatcggtatagaatataatcggggatgcctttatcttgaaaaaatgcacccgcagcttcgctagtaatcagtaaac
gcgggaagtggagtcaggcttttttttatggaagagaaaatagacaccaaagtagccttcttctaaccttaacggacctacagtgcaaaaagtt TABLE 9-continued Cbh2 plasmid sequences.

atcaagagactgcattatagagcgcacaaaggagaaaaaagtaatctaagatgctttgttagaaaaatagcgctctcgggatgcattttgta
gaacaaaaaagaagtatagattctttgttggtaaaatagcgctctcgcgttgcatttctgttctgtaaaaatgcagctcagattctttgtttgaaaaa
ttagcgctctcgcgttgcattttgttttacaaaaatgaagcacagattcttcgttggtaaaatagcgctttcgcgttgcatttctgttctgtaaaaat
gcagctcagattctttgtttgaaaaattagcgctctcgcgttgcattttgttctacaaaatgaagcacagatgcttcgttaacaaagatatgctatt
gaagtgcaagatggaaacgcagaaaatgaaccggggatgcgacgtgcaagattacctatgcaatagatgcaatagttctccaggaaccg
aaatacatacattgtcttccgtaaagcgctagactatatattattatacaggttcaaatatactatctgtttcagggaaaactcccaggttcggatgt
tcaaaattcaatgatgggtaacaagagcttttcaattcatcattttttttttattcttttttttgatttcggtttcttttgaaattttttttgattcggtaatc
tccgaacagaaggaagaacgaaggaaggagcacagacttagattggtatatatacgcatatgtagtgttgaagaaacatgaaattgcccagtattct
taacccaactgcacagaacaaaaaccgaaacgaagataaatcatgtcgaaagctacatataaggaacgtgctgctactcatcctagtcctgtt
gctgccaagctatttaatatcatgcacgaaaagcaaacaaacttgtgtgcttcattggatgttcgtaccaccaaggaattactggagttagttga
agcattaggtcccaaaatttgtttactaaaaacacatgtggatatcttgactgattttccatggagggcacagttaagccgctaaaggcattatc
cgccaagtacaatttttactcttcgaagacagaaaattgctgacattggtaatacagtcaaattgcagtactctgcgggtgtatacagaatagc
agaatgggcagacattacgaatgcacacggtgtggtgggcccaggtattgttagcggtttgaagcaggcggcagaagaagtaacaaagga
acctagaggccttttgatgttagcagaattgtcatgcaagggctccctatctactggagaatatactaagggtactgttgacattgcgaagagc
gacaaagattttgttatcggcttattgctcaaagagacatgggtggagagatgaaggttacgattggttgattatgacaccggtgtgggttt
agatgacaagggagacgcattgggtcaacagtatagaaccgtggatgatgtggtcttcacaggatctgacattattattgttggaagaggact
atttgcaaagggaagggatgctaaggtagagggtgaacgttacagaaaagcaggctgggaagcatatttgagaagatgcggccagcaaa
actaaaaaactgtattataagtaaatgcatgtatactaaactcacaaattagagcttcaatttaattatatcagttattaccctatgcggtgtgaaat
accgcacagatgcgtaaggagaaaataccgcatcaggcgccattcgccattcaggctgcgcaactgttgggaagggcgatcggtgcggg
cctcttcgctattacgccagctggcgaaggggggatgtgctgcaaggcgattaagttgggtaacgccagggttttcccagtcacgacgttgt
aaaacgacggccagtgccaagctttctaactgatctatccaaaactgaaaattacattcttgattaggtttatcacaggcaaatgtaatttgtggt
attttgccgttcaaaatctgtagaattttctcattggtcacattacaacctgaaaatactttatctacaatcataccattcttataacatgtcccttaat
actaggatcaggcatgaactgtcacagacaaaatcttcttgacaaacgtcacaattgatccctcccatccgttatcacaatgacaggtgtca
ttttgtgctcttatgggacgatccttattaccgctttcatccggtgatagaccgccacagagggggcagagagcaatcatcacctgcaaaccctt
ctatacactcacatctaccagtgtacgaattgcattcagaaaactgtttgcattcaaaaataggtagcatacaattaaaacatggcgggcacgta
tcattgcccttatcttgtgcagttagacgcgaattttttcgaagaagtaccttcaaagaatgggtctcatcttgttttgcaagtaccactgagcag
gataataatagaaatgataatatactatagtagagataacgtcgatgacttcccatactgcatttgcttttagttgtgtatttttagtgtgcaagtttct
gtaaatcgattaatttttttttcttcctctttttattaaccttaatttttattagattcctgacttcaactcaagacgcacagatattataacatctgc
acaataggcatttgcaagaattactcgtgagtaaggaaagagtgaggaactatcgcatacctgcatttaaagatgccgatttgggcgcgaatcctt
tattttggcttcaccctcatactattatcagggcagaaaaggaagtgtttccctccttcttgaattgatgttaccctcataaagcacgtggcctc
ttatcgagaaagaaattaccgtcgctcgtgatttgtttgcaaaaagaacaaaactgaaaaaaaccagacacgctcgacttcctgtcttcctattg
attgcagcttccaatttcgtcacacaacaaggtcctagcgacggctcacaggttttgtaacaagcaatcgaaggttctggaatggcgggaaa
gggtttagtaccacatgctatgatgcccactgtgatctccagagcaaagttcgttcgatcgtactgttactctctctcttttcaaacagaattgtccg
aatcgtgtgacaacaacagcctgttctcacacactcttttcttctaaccaagggggtggtttagtttagtagaacctcgtgaaacttacattttacat
atatataaacttgcataaattggtcaatgcaagaaatacatatttggtcttttctaattcgtagtttttcaagttcttagatgctttctttttctctttttt
acagatcatcaaggaagtaattatctacttttttacaacaaatataaacttaattaaAATGACTGCTTACAAATTGTTTTTGG
CTGCTGCTTTTGCTGCTACTGTTTGGCTGCTCCAGTTGAAGAAAGACAATCTTGTTC
TAATGGTGTTTGGTCACAATGTGGTGGTCAAAATTGGTCTGGTACTCCATGTTGTACA
TCTGGTAACAAGTGTGTTAAGGTTAATGATTTCTACTCTCAATGTCAACCAGGTTCTG
CTGATCCATCTCCAACTTCTACTATTGTTTCTGCTACTACTAAAGCTACTACTAC
AGGTTCTGGTGGTTCTGTTACTTCTCCACCACCAGTTGCTACAAACAATCCATTTTCT
GGTGTTGATTGTGGGCAAACAATTATTACAGATCAGAAGTTTTCTACTTTGGCTATTC
CAAAATTGTCTGGTGCTATGGCTACTGCTGCTGCAAAAGTTGCTGATGTTCCATCTTT
TCAATGGATGGATACTTACGATCATATTTCTTTCATGGAAGTTCTTTGGCTGATATT
AGAAAAGCAAACAAAGCAGGTGGTAATTATGCTGGTCAATTCGTTGTTTATGATTTG
CCAGATAGAGATTGTGCTGCTGCTGCTTCTAATGGTGAATACTCTTTGGATAAAGAT
GGTAAAAACAAGTACAAAGCTTATATTGCTGATCAAGGTATTTTGCAAGATTACTCT
GATACTAGAATCATTTTGGTTATTGAACCAGATTCTTTAGCTAACATGGTTACTAATA
TGAATGTTCCAAAATGTGCTAATGCTGCTTCTGCTTACAAAGAATTGACTATTCATGC
TTTGAAAGAATTGAATTTGCCAAACGTTTCAATGTATATTGATGCTGGTCATGGTGGT
TGGTTGGGTTGGCCAGCTAATTTGCCACCTGCTGCTCAATTGTATGGTCAATTGTACA
AAGATGCTGGTAAACCATCTAGATTGAGAGGTTTGGTTACTAATGTTTCTAATTACA
ACGCTTGGAAATTATCTTCTAAGCCAGATTATACTGAATCTAACCCAAATTACGATG
AACAAAAGTACATTCATGCTTTATCTCCATTGTTGGAACAAGAAGGTTGGCCAGGCG
CTAAGTTCATTGTTGATCAAGGTAGATCAGGTAAACAACCAACTGGTCAAAAAGCTT
GGGGTGATTGGTGTAATGCTCCAGGTACTGGTTTTGGTTTAAGGACCATCTGCTAATA
CTGGTGATGCTTTGGTTGATGCTTTTGTTTGGGTTAAACCAGGTGGTGAATCTGATGG
TACTTCTGATACTTCTGCTGCAAGATATGATTATCATTGTGGTATTGATGGTGCTGTT
AAACCAGCTCCAGAAGCTGGTACTTGGTTTCAAGCTTACTTTGAACAATTGTTGAAG
AATGCTAATCCATCTTTCTTGTTATAAggcgcgccgaattcgagagactcgagactgaatcggatcgatcccggg
cccgtcgagggatctgcgatagatcaattttttctttctctttcccatccttacgctaaaataatagtttatttattttttgaatattttttatttta
tatacgtatatatatagactatttttatctctttaatgattattaagatttttattaaaaaaaaaattcgctcctcttttaatgcctttatgcagttttttttttc
ccattcgatatttctatgttcgggtttcagcgtatttttaagtttaataactcgaaaattctgcgttcgttaaagcttgcatgcctgcaggtcgactctagagg
atccccgggtaccgagctcgaattaattcgtaatcatggtcat (SEQ ID NO: 38)

pRDH152
agctgtttcctgtgtgaaattgttatccgctcacaattccacacaacatacgagccggaagcataaagtgtaaagcctggggtgcctaatgagt
gagctaactcacattaattgcgttgcgctcactgcccgctttccagtcgggaaacctgtcgtgccagctggattaatgaatcggccaacgcgc
ggggagaggcggtttgcgtattgggcgctcttccgcttcctcgctcactgactcgctgcgctcggtcgttcggctgcggcgagcggtatcag
ctcactcaaaggcggtaatacggttatccacagaatcaggggataacgcaggaaagaacatgtgagcaaaaggccagcaaaaggccagg
aaccgtaaaaaggccgcgttgctggcgtttttccataggctccgcccccctgacgagcatcacaaaaatcgacgctcaagtcagaggtggc
gaaacccgacaggactataaagataccaggcgtttccccctggaagctccctcgtgcgctctcctgttccgaccctgccgcttaccggatac
ctgtccgcctttctcccttcgggaagcgtggcgctttctcaatgctcacgctgtaggtatctcagttcggtgtaggtcgttcgctccaagctggg
ctgtgtgcacgaaccccccgttcagcccgaccgctgcgccttatccggtaactatcgtcttgagtccaacccggtaagacacgacttatcgcc
actggcagcagccactggtaacaggattagcagagcgaggtatgtaggcggtgctacagagttcttgaagtggtggcctaactacggctac
actagaaggacagtatttggtatctgcgctctgctgaagccagttaccttcggaaaaagagttggtagctcttgatccggcaaacaaaccacc
gctggtagcggtggtttttttgtttgcaagcagcagattacgcgcagaaaaaaaggatctcaagaagatcctttgatcttttctacggggtctga
cgctcagtggaacgaaaactcacgttaagggattttggtcatgagattatcaaaaaggatcttcacctagatccttttaaattaaaaatgaagtttt TABLE 9-continued Cbh2 plasmid sequences.

aaatcaatctaaagtatatatgagtaaacttggtctgacagttaccaatgcttaatcagtgaggcacctatctcagcgatctgtctatttcgttcatc
catagagcctgactccccgtcgtgtagataactacgatacgggagggcttaccatctggccccagtgctgcaatgataccgcgagacccac
gctcaccggctccagatttatcagcaataaaccagccagccgagcagggccgagcgcagaagtggtcctgcaactttatccgcctccatcca
gtctattaattgttgccgggaagctagagtaagtagttcgccagttaatagtttgcgcaacgttgttgccattgctacaggcatcgtggtgtcac
gctcgtcgtttggtatggcttcattcagctccggttcccaacgatcaaggcgagttacatgatccccatgttgtgcaaaaaagcggttagctc
cttcggtcctccgatcgttgtcagaagtaagttggccgcagtgttatcactcatggttatggcagcactgcataattctcttactgtcatgccatcc
gtaagatgcttttctgtgactggtgagtactcaaccaagtcattctgagaatagtgttgcggcgaccgagttgctcttgcccggcgtcaatac
gggataataccgcgccacatagcagaactttaaaagtgctcatcattggaaaacgttcttcgggggcgaaaactctcaaggatcttaccgctgtt
gagatccagttcgatgtaaaccactcgtgcacccaactgatcttcagcatcttttactttcaccagcgtttctgggtgagcaaaaacaggaagg
caaaatgccgcaaaaaagggaataagggcgacacggaaatgttgaatactcatactcttcctttttcaatattattgaagcatttatcagggttat
tgtctcatgagcgggatacatatttgaatgtatttagaaaaataaacaaatagggttccgcgcacatttccccgaaaagtgccacctgacgtcta
agaaaccattattatcatgacattaacctataaaaataggcgtatcacgaggccctttcgtctcgcgcgtttcggtgatgacggtgaaaacctct
gacacatgcagctcccggagacggtcacagcttgtctgtaagcggatgccgggagcagacaagcccgtcagggcgcgtcagggtgtt
ggcgggtgtcggggctggcttaactatgcggcatcagagcagattgtactgagagtgcaccataacgcatttaagcataaacacgcactatg
ccgttcttctctcatgtatatatatatacaggcaacacgcagatataggtgcgacgtgaacagtgagctgtatgtgcgcagctcgcgttgcatttc
ggaagcgctcgttttcggaaacgctttgaagttcctattccgaagttcctattctctagctagaaagtataggaacttcagagcgcttttgaaaac
caaaagcgctctgaagacgcactttcaaaaaaccaaaaacgcaccggactgtaacgagctactaaaatattgcgaataccgcttccacaaa
cattgctcaaaagtatctctttgctatatatctctgtgctatatccctatataacctacccatccacctttcgctccttgaacttgcatctaaactcgac
ctctacatttttttatgtttatctctagtattactctttagacaaaaaatttgtagtaagaactattcatagagtgaatcgaaaacaatacgaaaatgta
aacattttcctatacgtagtatatagagacaaaatagaagaaaccgttcataatttctgaccaatgaagaatcatcaacgctatcacttttctgttca
caaagtatgcgcaatccacatcggtatagaatataatcggggatgcctttatcttgaaaaaatgcacccgcagcttcgctagtaatcagtaaac
gcgggaagtggagtcaggcttttttatggaagagaaaatagacaccaaagtagccttcttctaaccttaacggacctacagtcaaaaagtt
atcaagagactgcattatagagcgcacaaaggagaaaaaagtaatctaagatgcttgtttagaaaaatagcgactcgggatgcattttttgta
gaacaaaaaagaagtatagatctcttttgttggtaaaaatagcgctctcgcgttgcatttctgttctgtaaaaatgcagctcagattctttgtttgaaaaa
ttagcgctctcgcgttgcatttttgtttacaaaaatgaagcacagattcttcgttggtaaaatagcgctttcgcgttgcatttctgttctgtaaaaat
gcagctcagattctttgtttgaaaaattagcgctctcgcgttgcattttttgttctacaaaatgaagcacagatgcttcgttaacaaagatatgctatt
gaagtgcaagatggaaacgcagaaaatgaaccggggatgcgacgtgcaagatttacctatgcaatagtttctccaggaaccg
aaatacatacattgtcttccgtaaagcgctagactatatattattatacaggttcaaatatactatctgtttcagggaaaactcccaggttcggatgt
tcaaaattcaatgatgggtaacaagagcttttcaattcatcattttttttattctttttttttttgatttcggtttctttgaaatttttttgattcggtaat
ctccgaacagaaggaagaacgaaggaaggagcacagacttagattggtatatatacgcatatgtagtgttgaagaaacatgaaattgcccagtattct
taacccaactgcacagaacaaaaccgaaacgaagataaaatcatgtcgaaagctacatataaggaacgtgctgctactcatcctagtcctgtt
gctgccaagctatttaatatcatgcacgaaaagcaaaacaaacttgtgtgcttcattggatgttcgtaccaccaaggaattactggagttagttga
agcattaggtcccaaaatttgtttactaaaaacacatgtggatatcttgactgatttttccatggagggcacagttaagccgctaaaggcattatc
cgccaagtacaattttttactcttcgaagacagaaaatttgctgacattggtaatacagtcaaattgcagtactctgcgggtgtatacagaatagc
agaatgggcagacattacgaatgcacacggtgtggtgggcccaggtattgttagcggtttgaagcaggcggcagaagaagtaacaaagga
acctagaggccttttgatgttagcagaattgtcatgcaagggctccctatctactgggagaatatactaagggtactgttgacattgcgaagagc
gacaaagattttgttatcggctttattgctcaaagagacatgggtggaagagatgaaggttacgattggttgattatgacacccggtgtgggttt
agatgacaagggagacgcattgggtcaacagtatagaaccgtggatgatggtctctacaggatcgtgacattattattgttggaagaggact
atttgcaaagggaagggatgctaaggtagagggtgaacgttacagaaaagcaggctgggaagcatatttgagaagatgcggccagcaaa
actaaaaaactgtattataagtaaatgcatgtatactaaactcacaaattagacgttcaattttaattatatcagttattaccctatggtgtgaaat
accgcacagatgcgtaaggagaaaataccgcatcaggcgccattcgccattcaggctgcgcaactgttgggaagggcgatcggtgcggg
cctcttcgctattacgccagctggcgaaggggggatgtgctgcaaggcgattaagttgggtaacgccagggttttcccagtcacgacgttgt
aaaacgacggccagtgccaagctttctaactgatctatccaaaactgaaaattacattcttgattaggtttatcacaggcaaatgtaatttgtggt
attttgccgttcaaaatctgtagaattttctcattggtgcacattacaaccttatcctacaatcataccattcttataacatgtccccttaat
actaggatcaggcatgaacgcatcacagacaaaatcttcttgacaaacgtcacaattgatccctcccatccgttatcacaatgacaggtgtca
ttttgtgctcttatgggacgatcctttattaccgctttcatccggtgatagaccgccacagaggggcagagagcaatcatcacctgcaaacccttt
ctatacactcacatctaccagtgtacgaattgcattcagaaaactgtttgcattcaaaaataggtagcatacaattaaaacatggcgggcacgta
tcattgccctatctttgtgcagttagacgcgaatttttcgaagaagtaccttcaaagaaagtgggggtctcatctttgttttgcaagtaccactgagcag
gataataataagaaatgataatatactatagtagagataacgtcgatgacttcccatactgtaattgctttttagttgtgtattttttagtgtgcaagtttct
gtaaatcgattaattttttttttttcttcctcttttttattaaccttaattttatttttagattcctgacttcaactcaagacgcacagatattataacatctgc
acaataggcatttgcaagaattactcgtgagtaaggaaaagagtgaggaactatcgcatacctgcatttaaagatgccgatttgggcgcgaatcctt
tattttggctcaccctcatactattatcagggcagaaaaaggaagtgttttccctcctcttgattgatctttacctcataaagcacgtggcctc
ttatcgagaaagaaattaccgtcgctcgtgatttgtttgcaaaagaacaaaactgaaaaaaccccagacacgctcgacttcctgtcttcctattg
attgcagcttccaatttcgtcacacaacaaggtcctagcgacggctcacaggtttgtaacaagcaatcgaaggttctggaatggcgggaaa
gggtttagtaccacatgctatgatgcccactgtgatctcagagcaaagttcgttcgatcgtactgttactctctctctttcaaacagaattgtccg
aatcgtgtgacaacaacagcctgttctcacacactctttcttctaaccaagggggtggtttagtttagtagaacctcgtgaaacttacatttacat
atatataaacttgcataaattggtcaatgcaagaaatacatatttggtcttttctaaaaatcgtagttttcaagttcgtctagatgctttcttttttctcttttttt
acagatcatcaaggaagtaattatctactttttacaacaaatataaaacTTAATTAAAATGAAGTCTGCTGCTTTTTTG
GCTGCTTTAGCTGCTATTTTGCCAGCTTACGTTGCTGGTCAAGCTCAAACTTGGGCTC
AATGTGGTGGTATTGGTTTTACTGGTCCAACTACTTGTGTTGCTGGTTCTGTTTGTAC
TAAACAAAACGATTACTACTCTCAATGTATTCCAGGTTCTGCTACTACTCCAACTTCT
GCTCCAACATCTGCACCAACTTCTCAACCATCACAACCATCTTCTACTTCATCTGCTC
CATCTGGTCCATCTTCTACACCAACTCCATCTGCTAACAATCCATGGACTGGTTATCA
AATTTACTTGTCTCCATACTATGCTAATGAAGTTGCTGCAGCTGCTAAAGCTATTACT
GATCCAACTTTGGCTGCTAAAGCAGCTTCTGTTGCTAATATTCCAAATTTCACTTGGT
TGGATTCTGTTTCTAAAATTGCTGATTTGAAAACTTATTTGGCTGATGCTTCTGCTTT
GGGTAAATCTTCTGGTCAAAAGCAATTGTTGCAAATTGTTGTTTATGATTTGCCAGAT
AGAGATTGTGCTGCAAAAGCTTCTAATGGTGAATTTTCTATTGCTGATAATGGTTTGG
CTAACTACCAAAACTACATTGATCAAATTGTTGCTGCTTAAACAATTTCCAGATGT
TAGAGTTGTTGCTGTTATTGAACCAGATTCTTTGGCTAATTTGGTTACAAATTTAAAC
GTTCAAAAGTGTGCTAATGCTAAATCTACTTACTTGACTGCTGTTAATTATGCTTTGA
AGCAATTATCTTCTGTTGGTGTTTATCAATATATGGATGCTGGTCATGCTGGTTGGTT
GGGTTGGCCAGCTAATTTAACTCCAGCTGCTCAATTGTTTGCTCAAGTTTATTCTGAT
GCTGGTAAATCTCCATTCATTAAGGGTTTGGCTACTAATGTTGCTAATTACAATGCTT
TGTCTGCTGCTTCTCCAGATCCAATTACTCAAGGTGATCAAATTACGATGAAATTCA
TTACATTAATGCTTTGGCTCCAGCTTTGCAATCTGCTGGTTTTCCAGCTACTTTTATTG
TTGATCAAGGTAGATCAGGTCAACAAAATCATAGACAACAATGGGGTGATTGGTGT
AACATTAAAGGTGCTGGTTTTGGTACTAGACCAACTACTAATACTGGTTCTCTTTGA

TABLE 9-continued

Cbh2 plasmid sequences.

```
TTGATTCTATTGTTTGGGTTAAACCAGGTGGTGAATCTGATGGTACTTCTAATTCTTC
ATCTCCAAGATTTGATTCTACTTGTTCTTTGTCTGATGCTACTCAACCAGCTCCAGAA
GCTGGTACTTGGTTTCAAGCTTACTTTGAAACTTTGGTTTCTAAAGCTAATCCACCAT
TGTTATAAGGCGCGCCgaattcgagagactcgagactgaatcggatcgatcccgggcccgtcgagggatctgcgatagatc
aattttttcttttctctttccccatccttttacgctaaaataatagtttatttttttttttgaatatttttttatttatatacgtatatatagactattattt
atcttttaatgattattaagattttttattaaaaaaaaattcgctcctcttttaatgcctttatgcagtttttttttcccattcgatatttctatgttcgggt
tcagcgtattttaagtttaataactcgaaaattctgcgttcgttaaagcttgcatgcctgcaggtcgactctagaggatccccgggtaccgagctcgaatta
attcgtaatcatggtcat (SEQ ID NO: 39)

pRDH153
agctgtttcctgtgtgaaattgttatccgctcacaattccacacaacatacgagccggaagcataaagtgtaaagcctggggtgcctaatgagt
gagctaactcacattaattgcgttgcgctcactgcccgctttccagtcgggaaacctgtcgtgccagctggattaatgaatcggccaacgcgc
ggggagaggcggtttgcgtattgggcgctcttccgcttcctcgctcactgactcgctgcgctcggtcgttcggctgcggcgagcggtatcag
ctcactcaaaggcggtaatacggttatccacagaatcaggggataacgcaggaaagaacatgtgagcaaaaggccagcaaaaggccagg
aaccgtaaaaaggccgcgttgctggcgtttttccataggctccgcccccctgacgagcatcacaaaaatcgacgctcaagtcagaggtggc
gaaacccgacaggactataaagataccaggcgtttccccctggaagctccctcgtgcgctctcctgttccgaccctgccgcttaccggatac
ctgtccgcctttctcccttcgggaagcgtggcgctttctcaatgctcacgctgtaggtatctcagttcggtgtaggtcgttcgctccaagctggg
ctgtgtgcacgaaccccccgttcagcccgaccgctgcgccttatccggtaactatcgtcttgagtccaacccggtaagacacgacttatcgcc
actggcagcagccactggtaacaggattagcagagcgaggtatgtaggcggtgctacagagttcttgaagtggtggcctaactacggctac
actagaaggacagtatttggtatctgcgctctgctgaagccagttaccttcggaaaaagagttggtagctcttgatccggcaaacaaaccacc
gctggtagcggtggtttttttgtttgcaagcagcagattacgcgcagaaaaaaaggatctcaagaagatcctttgatcttttctacggggtctga
cgctcagtggaacgaaaactcacgttaagggattttggtcatgagattatcaaaaaggatcttcacctagatccttttaaattaaaaatgaagtttt
aaatcaatctaaagtatatatgagtaaacttggtctgacagttaccaatgcttaatcagtgaggcacctatctcagcgatctgtctatttcgttcatc
catagttgcctgactccccgtcgtgtagataactacgatacgggagggcttaccatctggccccagtgctgcaatgataccgcgagacccac
gctcaccggctccagatttatcagcaataaaccagccagccggaagggccgagcgcagaagtggtcctgcaactttatccgcctccatcca
gtctattaattgttgccgggaagctagagtaagtagttcgccagttaatagtttgcgcaacgttgttgccattgctacaggcatcgtggtgtcac
gctcgtcgtttggtatggcttcattcagctccggttcccaacgatcaaggcgagttacatgatcccccatgttgtgcaaaaaagcggttagctc
cttcggtcctccgatcgttgtcagaagtaagttggccgcagtgttatcactcatggttatggcagcactgcataattctcttactgtcatgccatcc
gtaagatgcttttctgtgactggtgagtactcaaccaagtcattctgagaatagtgtatgcggcgaccgagttgctcttgcccggcgtcaatac
gggataataccgcgccacatagcagaactttaaaagtgctcatcattggaaaacgttcttcggggcgaaaactctcaaggatcttaccgctgtt
gagatccagttcgatgtaacccactcgtgcacccaactgatcttcagcatcttttactttcaccagcgtttctgggtgagcaaaaacaggaagg
caaaatgccgcaaaaaagggaataagggcgacacggaaatgttgaatactcatactcttcctttttcaatattattgaagcatttatcagggttat
tgtctcatgagcggatacatatttgaatgtatttagaaaaataaacaaataggggttccgcgcacatttccccgaaaagtgccacctgacgtcta
agaaaccattattatcatgacattaacctataaaaataggcgtatcacgaggccctttcgtctcgcgcgtttcggtgatgacggtgaaaacctct
gacacatgcagctcccggagacggtcacagcttgtctgtaagcggatgccgggagcagacaagcccgtcagggcgcgtcagcgggtgtt
ggcgggtgtcggggctggcttaactatgcggcatcagagcagattgtactgagagtgcaccataaacgcatttaagcataaacacgcactatg
ccgttcttctcatgtatatatatatacaggcaacacgcagatataggtgcgacgtgaacagtgagctgtatgcgcagacgcgttgcattttc
ggaagcgctcgttttcggaaacgctttgaagttcctattccgaagttcctattctctagtagaaagtataggaacttcagagcgcttttgaaaac
caaaagcgctctgaagacgcactttcaaaaaaccaaaaacgcaccggactgtaacgagctactaaaatattgcgaataccgcttccacaaa
cattgctcaaaagtatctctttgctaaggaacggttttataaataccatccacctccaccttttcgctcctttgcatctcaaactcgac
ctctacattttttatgtttatctctagtattactctttagacaaaaaaattgtagtaagaaccatattcatagaggtgaatcgaaaacaatacgaaaatgta
aacatttcctatacgtagtatatagagacaaaatagaagaaaccgttcataattttctgaccaatgaagaatcatcaacgctatcactttctgttca
caaagtatgcgcaatccacatcggtatagaatataatcggggatgcctttatcttgaaaaaatgcacccgcagcttcgctagtaatcagtaaac
gcgggaagtggagtcaggcttttttttatggaagagaaatagacaccaaagtagccttcttaacgaccttaccttaacgcagtgcgcaaaagtt
atcaagagactgcattatagagcgcacaaaggagaaaaaaagtaatctaagatgctttgttagaaaaatagcgctctcgcggatgcatttttgta
gaacaaaaaagaagtatagattcttttgttggtaaaatagcgctctcgcgttgcatttctgttctgtaaaaatgcagctcagattctttgtttgaaaaa
ttagcgctctcgcgttgcattttgtttcacaaaaatgaagcacagattcttcgttggtaaaatagcgctttcgcgttgcatttctgttctgtaaaaat
gcagctcagattctttgtttgaaaaattagcgctctcgcgttgcattttgttctacaaaatgaagcacagatgcttcgttaacaaagatatgctatt
gaagtgcaagatggaaacgcagaaaatgaaccggggatgcgacgtgcaagattacctatgcaatagatgcaatagtttctccaggaaccg
aaatacatacattgtcttccgtaaagcgctagactatatattattatacaggttcaaatatactatctgtttcagggaaaactcccaggttcggatgt
tcaaaattcaatgatgggtaacaagagcttttcaattcatcatttttttttttattcttttttttgatttcggtttctttgaaatttttttgattcggtaat
ctccgaacagaaggaagaacgaaggaaggagcacagacttagattggtatatatacgcatatgtagtgttgaagaaacatgaaattgcccagtattct
taacccaactgcacagaacaaaaaccgaagaatatcatgtcgaaagctacatataaggaacgtgctgctactcatcctagtcctgtt
gctgccaagctatttaatatcatgcacgaaaagcaaacaaacttgtgtgcttcattggatgttcgtaccaccaaggaattactggagttagttga
agcattaggtcccaaaatttgtttactaaaaacacatgtggatatcttgactgatttttccatggagggcacagttaagccgctaaaggcattatc
cgccaagtacaattttttactcttcgaagacagaaaatttgctgacattggtaatacagtcaaattgcagtactctgcgggtgtatacagaatagc
agaatgggcagacattacgaatgcacacggtgtggtgggcccaggtattgttagcggtttgaagcggatagttggttgattatgacacccggtgtgggttt
agatgacaagggagacgcattgggtcaacagtatagaaccgtggatgatgtggtctctacaggatctgacattattattgttggaagaggact
atttgcaaagggaagggatgctaaggtagaggggtacaggtacagaaggtgaagcaggtagtttgagaagatgcggcagcagcaaa
actaaaaaactgtattataagtaaatgcatgtatactaaactcacaaattagagcttcaatttaattatatcagttattacccctatgcggtgtgaaat
accgcacagatgcgtaaggagaaaataccgcatcaggcgccattcgccattcaggctgcgcaactgttgggaagggcgatcggtgcggg
cctcttcgctattacgccagctggcgaaggggggatgtgctgcaaggcgattaagttgggtaacgccagggttttcccagtcacgacgttgt
aaaacgacggccagtgccaagcttctcaactgatctatccaaaactgaaatttcttttagtttctcacagcatcttttgtggt
attttgccgttcaaaatctgtagaattttctcattgtcacattacaacctgaaaatacttttctacaatcatccaccattcttataacatgtcccttaat
actaggatcaggcatgaacgcatcacagacaaaatcttcttgacaaacgtcacaattgatccctccccatccgttatcacaatgacaggtgtca
ttttgtgctcttatgggacgatcctattaccgctttcatccggtgatagaccgccacagaggggcagagagcaatcatcacctgcaaacccttt
ctatacactccatgtaccagtgtacgaattgcattcagaaaatacttcattcaaaaatagtagcactaaataagatttaaaacatgggggcacgta
tcattgccctttatcttgtgcagttagacgcgaatttttcgaagaagtaccttcaaagaatggggtctcatcttgttttgcaagtaccactgagcag
gataataatagaaatgataatatactatagtagagataacgtcgatgacttcccatactgtaattgcttttagttgtgtatttttagtgtgcaagtttct
gtaaatcgattaattttttttcttcctcttttattaaccttaattttattttagattcctgacttcaactcaagacgcacagatattataacatctgc
acaataggcatttgcaagaattactcgtgagtaaggaaagagtgaggaactatcctgcattaaagatgccgatttgggcgcgaatcctttattt
tggcttcaccctcatactattatcagggccagaaaaaggaagtgtttccctccttcttgaattgatgttaccctcataaagcacgtggcctc
ttatcgagaaagaaattaccgtcgctcgtgatttgtttgcaaaaagaacaaaactgaaaccacccagacacgctcgacttcctgtcttcctattg
attgcagcttccaatttcgtcacacaacaaggtcctagcgacggctcacaggtttttgtaacaagcaatcgaaggttctggaatggcgggaaa
gggtttagtaccacatgctatgatgcccactgtgatctccagagcaaagttcgttcgatcgtactgttactctctctcttttcaaacagaattgtccg
aatcgtgtgacaacaacagcctgttctcacacactcttttcttctaaccaagggggtggtttagtttagtagaacctcgtgaaacttacatttacat
```

TABLE 9-continued

Cbh2 plasmid sequences.

atatataaacttgcataaattggtcaatgcaagaaatacatatttggtcttttctaattcgtagtttttcaagttcttagatgctttcttttctctttttt
acagatcatcaaggaagtaattatctactttttacaacaaatataaaacttaattaaAATGTCTAGATTCTCTGCTTTGACTG
CTTTGTTGTTGTCTTTGCCATTGTTGGCTATTGCTCAATCTCCATTGTATGGTCAATGT
GGTGGTAATGGTTGGACTGGTCCAAAAACTTGTGTTTCTGGTGCTACTTGTACTGTTA
TTAATGATTGGTATTGGCAATGTTTGCCAGGTAATGGTCCAACTTCTTCTTCTCCAAC
TTCTACTCCAACTACAACTACTACTACTGGTGGTCCACAACCAACTGTTCCAGCTGCT
GGTAATCCATATACTGGTTACGAAATTTACTTGTCTCCATATTATGCTGCTGAAGCTC
AAGCTGCTGCTGCTCAAATTTCTGATGCTACTCAAAAAGCTAAAGCTTTGAAAGTTG
CTCAAATTCCAACTTTTACTTGGTTTGATGTTATTGCTAAAACTTCTACTTTGGGTGA
TTATTTGGCTGAAGCTTCTGCTTTGGGTAAATCTTCTGGTAAAAAGTACTTGGTTCAA
ATTGTTGTTTATGATTTGCCAGATAGAGATTGTGCTGCTTTGGCTTCTAATGGTGAAT
TTTCTATTGCTAACAACGGTTTGAACAATTACAAAGGTTACATTGATCAATTGGTTGC
ACAAATTAAGAAATACCCAGATGTTAGAGTTGTTGCTGTTATTGAACCAGATTCTTT
GGCTAATTTGGTTACAAATTTGAACGTTTCTAAGTGTGCTAATGCTCAAACTGCTTAC
AAAGCTGGTGTTACTTATGCTTTGCAACAATTGAACTCTGTTGGTGTTTACATGTATT
TGGATGCTGGTCATGCTGGTTGGTTGGGTTGGCCAGCTAATTTGAATCCAGCTGCTC
AATTGTTTTCTCAATTGTATAGAGATGCTGGTTCTCCACAATACGTTAGAGGTTTGGC
TACTAATGTTGCTAATTACAATGCTTTGTCTGCTTCTTCACCAGATCCAGTTACTCAA
GGTAATCCAAATTACGATGAATTGCATTACATTAATGCTTTGGCTCCAGCTTTGCAAT
CTGGTGGTTTTCCAGCTCATTTTATTGTTGATCAAGGTAGATCAGGTGTTCAAAACAT
TAGACAACAATGGGGTGATTGGTGTAATGTTAAAGGTGCTGGTTTTGGTCAAAGACC
AACTTTATCTACTGGTTCTTCTTTGATTGATGCTATTGTTTGGATTAAACCAGGTGGT
GAATGTGATGGTACTACTAATACATCTTCTCCAAGATATGATTCTCATTGTGGTTTGT
CTGATGCTACTCCAAATGCTCCTGAAGCTGGTCAATGGTTTCAAGCTTACTTTGAAAC
TTTGGTTAGAAATGCTTCTCCACCATTGTTATAAggcgcgccgaattcgagagactcgagactgaatcgga
tcgatcccgggcccgtcgagggatctgcgatagatcaatttttttcttttctctttcccatccttttacgctaaaataatagtttatttttattttttgaata
tttttttatttatatacgtatatatagactattatttatctttaatgattattaagattttattaaaaaaaaattcgctcctcttttaatgcctttatgca
gtttttttttcccattcgatatttctatgttcgggttcagcgtatttttaagtttaataactcgaaaattctgcgttcgttaaagcttgcatgcctgcaggtc
gactctagaggatccccgggtaccgagctcgaattaattcgtaatcatggtcat (SEQ ID NO: 40)

pRDH154
agctgtttcctgtgtgaaattgttatccgctcacaattccacacaacatacgagccggaagcataaagtgtaaagcctggggtgcctaatgagt
gagctaactcacattaattgcgttgcgctcactgcccgctttccagtcgggaaacctgtcgtgccagctggattaatgaatcggccaacgcgc
ggggagaggcggtttgcgtattgggcgctcttccgcttcctcgctcactgactcgctgcgctcggtcgttcggctgcggcgagcggtatcag
ctcactcaaaggcggtaatacggttatccacagaatcaggggataacgcaggaaagaacatgtgagcaaaaggccagcaaaaggccagg
aaccgtaaaaaggccgcgttgctggcgtttttccataggctccgcccccctgacgagcatcacaaaaatcgacgctcaagtcagaggtggc
gaaacccgacaggactataaagataccaggcgtttccccctggaagctccctcgtgcgctctcctgttccgaccctgccgcttaccggatac
ctgtccgcctttctcccttcgggaagcgtggcgctttctcaatgctcacgctgtaggtatctcagttcggtgtaggtcgttcgctccaagctggg
ctgtgtgcacgaaccccccgttcagcccgaccgctgcgccttatccggtaactatcgtcttgagtccaacccggtaagacacgacttatcgcc
actggcagcagccactggtaacaggattagcagagcgaggtatgtaggcggtgctacagagttcttgaagtggtggcctaactacggctac
actagaaggacagtatttggtatctgcgctctgctgaagccagttaccttcggaaaaagagttggtagctcttgatccggcaaacaaaccacc
gctggtagcggtggtttttttgtttgcaagcagcagattacgcgcagaaaaaaaggatctcaagaagatcctttgatcttttctacggggtctga
cgctcagtggaacgaaaactcacgttaagggattttggtcatgagattatcaaaaaggatcttcacctagatccttttaaattaaaaatgaagtttt
aaatcaatctaaagtatatatgagtaaacttggtctgacagttaccaatgcttaatcagtgaggcacctatctcagcgatctgtctatttcgttcatc
catagttgcctgactccccgtcgtgtagataactacgatacgggagggcttaccatctggccccagtgctgcaatgataccgcgagacccac
gctcaccggctccagatttatcagcaataaaccagccagccggaagggccgagcgcagaagtggtcctgcaactttatccgcctccatcca
gtctattaattgttgccgggaagctagagtaagtagttcgccagttaatagtttgcgcaacgttgttgccattgctacaggcatcgtggtgtcac
gctcgtcgtttggtatggcttcattcagctccggttcccaacgatcaaggcgagttacatgatcccccatgttgtgcaaaaaagcggttagctc
cttcggtcctccgatcgttgtcagaagtaagttggccgcagtgttatcactcatggttatggcagcactgcataattctcttactgtcatgccatcc
gtaagatgcttttctgtgactggtgagtactcaaccaagtcattctgagaatagtgtatgcggcgaccgagttgctcttgcccggcgtcaatac
gggataataccgcgccacatagcagaactttaaaagtgctcatcattggaaaacgttcttcggggcgaaaactctcaaggatcttaccgctgtt
gagatccagttcgatgtaacccactcgtgcacccaactgatcttcagcatcttttactttcaccagcgtttctgggtgagcaaaaacaggaagg
caaaatgccgcaaaaaagggaataagggcgacacggaaatgttgaatactcatactcttcctttttcaatattattgaagcatttatcagggttat
tgtctcatgagcggatacatatttgaatgtatttagaaaaataaacaaataggggttccgcgcacatttccccgaaaagtgccacctgacgtcta
agaaaccattattatcatgacattaacctataaaaataggcgtatcacgaggccctttcgtctcgcgcgtttcggtgatgacggtgaaaacctct
gacacatgcagctcccggagacggtcacagcttgtctgtaagcggatgccgggagcagacaagcccgtcagggcgcgtcagcgggtgtt
ggcgggtgtcggggctggcttaactatgcggcatcagagcagattgtactgagagtgcaccataacgcatttaagcataaacacgcactatg
ccgttcttctcatgtatatatatatacaggcaacacgcagatataggtgcgacgtgaacagtgagctgtatgcgcagctcgcgttgcattttc
ggaagcgctcgttttcggaaacgctttgaagttcctattccgaagttcctattctctagctagaaagtataggaacttcagagcgcttttgaaaac
caaaagcgctctgaagacgcactttcaaaaaaccaaaaacgcaccggactgtaacgagctactaaaatattgcgaataccgcttccacaaa
cattgctcaaaagtatctctttgctatatatctctgtgctatatccctatacccaccctcgcttcttgaacttgcatctaaactcgac
ctctacattttttatgtttatctctagtattactctttagacaaaaaaattgtagtaagaactattcatagagtgaatcgaaaacaatacgaaaatgta
aacatttcctatacgtagtatatagagacaaaatagaagaaaccgttcataattttctgaccaatgaagaatcatcaacgctatcactttctgttca
caagtatgcgcaatccacatcggtatagaatataatcggggatgcctttatcttgaaaaaatgcacccgcagcttcgctagtaatcagtaaac
gcgggaagtggagtcaggcttttttatgaagaaatagacaccaaagtagccttcttctaacctttaaccgaccttacagtgcaaaagtt
atcaagagactgcattatagagcgcacaaaggagaaaaaaagtaatctaagatgctttgttagaaaaatagcgctctcgggatgcatttttgta
gaacaaaaaagaagtatagattctttgttggtaaaatagcgctctcgcgttgcatttctgttctgtaaaaatgcagctcagattctttgtttgaaaaa
ttagcgctctcgcgttgcattttgttttacaaaaatgaagcacagattcttcgttggtaaaatagcgctttcgcgttgcatttctgttctgtaaaaat
gcagctcagattctttgtttgaaaaattagcgctctcgcgttgcattttgttctacaaaatgaagcacagatgcttcgttaacaaagatgctatt
gaagtgcaagatggaaacgcagaaaatgaaccgggatgcgacgtgcaagattacctatgcaatgcatgcaatagttctctcaggaaccg
aaatacatacattgtcttccgtaaagcgctagactatatattattatacaggttcaaatatactatctgtttcagggaaaactcccaggtcggatgt
tcaaaattcaatgatgggtaacaagagcttttcaattcatcatttttttttattcttttttttgatttcggtttctttgaaattttttgattcggtaatc
tccgaacagaaggaagaacgaaggaaggagcacagacttagattggtatatatacgcatatgtagtgttgaagaaacatgaaattgcccagtattct
taacccaactgcacagaacaaaaaccgaaagaaaacatgtgaaacactacatataaggaacgtgctgctactcatcctagtcctgtt
gctgccaagctatttaatatcatgcacgaaaagcaaacaaacttgtgtgcttcattggatgttcgtaccaccaaggaattactggagttagttga
agcattaggtcccaaaatttgtttactaaaaacacatgtggatatcttgactgatttttccatggagggcacagttaagccgctaaaggcattatc
cgccaagtacaattttttactcttcgaagacagaaaatttgctgacattggtaatacagtcaaattgcagtactctgcgggtgtatacagaatagc
agaatgggcagacattacgaatgcacacggtgtggtgggcccaggtattgttagcggtttgaagcaggcggcagaagaagtaacaaagga

TABLE 9-continued

Cbh2 plasmid sequences.

```
acctagaggcctttgatgttagcagaattgtcatgcaagggctccctatctactggagaatatactaagggtactgttgacattgcgaagagc
gacaaagattttgttatcggctttattgctcaaagagacatgggtggaagagatgaaggttacgattggttgattatgacacccggtgtgggttt
agatgacaagggagacgcattgggtcaacagtatagaaccgtggatgatgtggtctctacaggatctgacattattattgttggaagaggact
atttgcaaagggaagggatgctaaggtagagggtgaacgttacagaaaagcaggctgggaagcatatttgagaagatgcggccagcaaa
actaaaaaactgtattataagtaaatgcatgtatactaaactcacaaattagagcttcaatttaattatatcagttattaccctatgcggtgtgaaat
accgcacagatgcgtaaggagaaaataccgcatcaggcgccattcgccattcaggctgcgcaactgttgggaagggcgatcggtgcggg
cctcttcgctattacgccagctggcgaagggggatgtgctgcaaggcgattaagttgggtaacgccagggttttcccagtcacgacgttgt
aaaacgacggccagtgccaagctttctaactgatctatccaaaactgaaaattacattcttgattaggtttatcacaggcaaatgtaatttgtggt
attttgccgttcaaaatctgtagaattttctcattggtcacattacaacctgaaaatactttatctacaatcataccattcttataacatgtcccttaat
actaggatcaggcatgaacgcatcacagacaaaatcttcttgacaaacgtcacaattgatccctccccatccgttatcacaatgacaggtgtca
ttttgtgctcttatgggacgatccttattaccgctttcatccggtgatagaccgccacagagggcagagagcaatcatcacctgcaaacctt
ctatacactcacatctaccagtgtacgaattgcattcagaaaactgtttgcattcaaaaataggtagcatacaattaaaacatggcgggcacgta
tcattgcccttatcttgtgcagttagacgcgaattttcgaagaagtaccttcaaagaatgggtctcatcttgttttgcaagtaccactgagcag
gataataatagaaatgataatatactatagtagagataacgtcgatgacttcccatactgtaattgcttttagttgtgtattttagtgtgcaagtttct
gtaaatcgattaatttttttttttcttttcctcttttttattaaccttaattttttagattcctgacttcaactcaagacgcacagatattataacatctgc
acaataggcatttgcaagaattactcgtgagtaaggaaagagtgaggaactatcgcatacctgcatttaaagatgccgatttgggcgcgaatcctt
tattttggcttcaccctcatactattatcagggccagaaaaaggaagtgtttccctccttcttgaattgatgttaccctcataaagcacgtggcctc
ttatcgagaaagaaattaccgtcgctcgtgatttgtttgcaaaaagaacaaaactgaaaaaacccagacacgctcgacttcctgtcttcctattg
attgcagcttccaatttcgtcacacaacaaggtcctagcgaccgctcacaggttttgtaacaagcaatcgaaggttctggaatggcgggaaa
gggtttagtaccacatgctatgatgcccactgtgatctccagagcaaagttcgttcgatcgtactgttactctctctctttcaaacagaattgtccg
aatcgtgtgacaacaacagcctgttctcacacactcttttcttctaaccaagggggtggtttagtttagtagaacctcgtgaaacttacatttacat
atatataaacttgcataaattggtcaatgcaagaaatacatatttggtcttttctaattcgtagtttttcaagttcttagatgctttcttttttctcttttt
acagatcatcaaggaagtaattatctactttttacaacaaatataaaactttaattaaAATGAAGGCTTCTATTGCTTTGACTG
CTATTGCTGCTTTGGCTGCTAATGCTTCTGCTGCTTGTTTTTCTGAAAGATTGGGTTAT
CCATGTTGTAGAGGTAATGAAGTTTTCTACACTGATAATGATGGTGATTGGGGTGTT
GAAAATGGTAATTGGTGTGGTATTGGTGGTGCTTCTGCTACTACTTGTTGGTCACAA
GCTTTAGGTTACCCTTGTTGTACTTCTACTTCTGATGTTGCTTTACGTTGATGGTGACG
GTAACTGGGGTGTCGAAAACGGTAACTGGTGCGGTATAATTGCAGGTGGTAATTCTT
CTAACAACAACTCTGGTTCTACTATTAATGTTGGTGATGTTACTATTGGTAACCAATA
CACTCATACTGGTAATCCATTTGCTGGTCATAAATTCTTTATTAACCCATACTATACT
GCTGAAGTTGATGGTGCTATTGCTCAAATTTCTAATGCTTCTTTGAGAGCTAAAGCTG
AAAAGATGAAAGAATTTTCTAACGCTATTTGGTTGGATACTATTAAGAATATGAACG
AATGGTTGGAAAAGAATTTGAAATATGCTTTGGCTGAACAAAATGAAACTGGTAAG
ACTGTTTTGACAGTTTTTGTTGTTTATGATTTGCCAGGTAGAGATTGTCATGCTTTAG
CTTCTAATGGTGAATTGTTGGCTAATGATTCTGATTGGGCAAGATATCAATCTGAAT
ACATTGATGTTATTGAAGAAAAGTTGAAAACTTACAAGTCTCAACCAGTTGTTTTGG
TTGTTGAACCAGATTCTTTGGCTAATATGGTTACAAATTTGGATTCTACTCCAGCTTG
TAGAGATTCTGAAAAATACTATATGGATGGTCATGCTTACTTGATTAAAAAGTTGGG
TGTTTTGCCACATGTTGCAATGTATTTGGATATTGGTCATGCTTTTTGGTTGGGTTGG
GATGATAATAGATTGAAAGCTGGTAAAGTTTACTCTAAGGTTATTCAATCTGGTGCT
CCAGGTAATGTTAGAGGTTTTGCTTCTAATGTTGCTAATTATACTCCATGGGAAGATC
CAACTTTGTCTAGAGGTCCAGATACTGAATGGAATCCATGTCCAGATGAAAAAAGAT
ACATTGAAGCAATGTACAAAGATTTTAAGTCTGCTGGTATTAAGTCTGTTTACTTCAT
TGATGATACTTCTAGAAATGGTCATAAGACTGATAGAACTCATCCAGGTGAATGGTG
TAATCAAACAGGTGTTGGTATTGGTGCTAGACCACAAGCTAATCCAATTTCTGGTAT
GGATTACTTGGATGCTTTTTATTGGGTTAAACCATTGGGTGAATCTGATGGTTATTCT
GATACTACTGCTGTCAGATATGATGGTTATTGTGGTCATGCTACTGCTATGAAACCA
GCTCCTGAAGCTGGTCAATGGTTTCAAAAACATTTCGAACAAGGTTTGGAAAATGCT
AATCCACCATTGTTATAAggcgcgccgaattcgagagactcgagactgaatcggatcgatcccgggcccgtcgagggat
ctgcgatagatcaattttttctttctctttccccatcctttacgctaaaataatagttttattttattttttgaatatttttttatttatatacgtatatat
agactattatttatcttttaatgattattaagattttttattaaaaaaaaattcgctcctcttttaatgcctttatgcagttttttttttcccattcgatattt
ctatgttcgggttcagcgtattttaagtttaataactcgaaaattctgcgttcgttaaagcttgcatgcctgcaggtcgactctagaggatccccgggtacc
gagctcgaattaattcgtaatcatggtcat (SEQ ID NO: 41)
```

The plasmids were all transformed to *S. cerevisiae* (strain Y294), and transformants were confirmed with PCR. Along with the reference strain containing a plasmid without a heterologous cellulase and a strain expressing the Clcbh2b (pMU784), the five cbh2 containing strains were tested for protein production. The strains were grown in double strength SC$^{-URA}$ medium (3.4 g/L YNB; 3 g/L amino acid dropout pool without uracil; 10 g/L ammonium sulfate; 20 g/L glucose) that was buffered to pH 6 (20 g/L succinic acid; 12 g/L NaOH, set pH to 6 with NaOH). Glucose was added after autoclaving of the other components from a 50% glucose stock solution. 10 mL cultures in 125 mL Erlenmeyer flasks were grown at 30° C. for three days. Three flasks were inoculated for each strain. After incubation, samples were taken for analysis. After centrifugation of the samples, 12 μl of each was taken, added to 5 μl of protein loading buffer and boiled for 5 minutes. The samples were subsequently loaded on a 10% SDS-PAGE and separated, followed by silver staining (FIG. 2).

The theoretical enzyme size was estimated for each of the heterologous genes using the Compute pI/Mw tool available at the ExPasy Bioformatic Resource Portal. The results are listed in Table 5. FIG. 2 shows that bands in the expected size range were visible for *C. heterostrophus* CELT (pRDH151) and *Piromyces* sp. CEL6A (pRDH154). In addition, *V. volvacea* CBHII-I appears as a diffuse band in the 130 KDa range. This size is greater than the predicted enzyme size, and the diffuse band was seen on several gels.

Example 2

Avicel Hydrolysis in Yeast Expressing a Heterologous Cbh2

All strains were then tested for activity using the high-throughput Avicel conversion method using an Avicel concentration of 1% (or 10 g/L). The Dintrosalicylic Acid Reagent Solution (DNS) used for the assay procedure contained phenol which, according to literature, renders greater sensitivity. Activity data can be seen in FIG. 3. From the activity data it is apparent that the strain expressing *C. heterostrophus* CEL7 (pRDH150) and *V. volvacea* CBHII-I (pRDH153) yielded appreciable amounts of activity on Avicel. The *Piromyces* sp. CEL6A-expressing strain also showed some activity.

Example 3

Specific Activity of Cbh2s Expressed Heterologously in Yeast

To estimate the specific activity of the Cbh2s, the Bradford method (BioRad protein assay) was used as it is prescribed for microtiter plates, using the Gamma globulin standard. Supernatants samples were first subjected to the buffer exchange procedure as directed for the 2 mL Zeba desalt spin columns (Thermo Scientific). The amount of protein detected by the protein assay seemed to agree with what was seen on the SDS-PAGE.

The average amount of protein present in the REF strain samples was then subtracted from the amount of protein measured in the other samples to give an indication of the amount of heterologously expressed Cbh2 that was present in each sample (FIG. 4). Next, the specific activity of each CBH was estimated by dividing the activity (FIG. 3) by the amount of CBH present (FIG. 4) and expressed in "percentage degradation per µg protein" (FIG. 5). *C. heterostrophus* CEL7 (pRDH150) and *V. volvacea* CBHII-I (pRDH153) had 2.6 times and 1.5 times greater specific activity than ClCbh2b on Avicel.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. An isolated polynucleotide comprising a nucleic acid which encodes a cellobiohydrolase or a functional fragment thereof, wherein at least 70% of the codons of said nucleic acid is codon-optimized for expression in a heterologous yeast host cell and wherein the cellobiohydrolase has an amino acid sequence of SEQ ID NO: 11, SEQ ID NO: 12, SEQ ID NO: 13, SEQ ID NO: 14, or SEQ ID NO: 15.

2. The isolated polynucleotide of claim 1, wherein the fragment of the cellobiohydrolase is a cellobiohydrolase cellulose-binding module (CBM).

3. The isolated polynucleotide of claim 1, wherein said polynucleotide is operably associated with a heterologous nucleic acid.

4. The isolated polynucleotide of claim 3, wherein the heterologous nucleic acid encodes a signal peptide, a secretion signal, or a carbohydrate binding module.

5. A vector comprising the isolated polynucleotide of claim 1.

6. The vector of claim 5 further comprising an S. cerevisiae Phosphoglycerate Kinase (PGK1) promoter, an S. cerevisiae Phosphoglycerate Kinase (PGK1) terminator or both an S. cerevisiae Phosphoglycerate Kinase (PGK1) promoter, and an S. cerevisiae Phosphoglycerate Kinase (PGK1) terminator.

7. A host cell comprising the isolated polynucleotide of claim 1.

8. A method of fermenting cellulose comprising culturing the host cell of claim 7 in medium that contains crystalline cellulose under suitable conditions for a period sufficient to allow saccharification and fermentation of the cellulose.

9. The method of claim 8, wherein said host cell produces ethanol.

10. The isolated polynucleotide of claim 1, wherein the nucleic acid is as set forth in SEQ ID NO: 6, SEQ ID NO:7, SEQ ID NO:8, SEQ ID NO:9, or SEQ ID NO: 10.

11. The isolated polynucleotide of claim 2, wherein the CBM comprises an amino acid sequence selected from the group consisting of SEQ ID NO: 26, SEQ ID NO: 29, SEQ ID NO: 32, SEQ ID NO: 35, and SEQ ID NO: 36.

12. The isolated polynucleotide of claim 1, wherein the heterologous yeast host cell is Saccharomyces cerevisiae.

13. The isolated polynucleotide of claim 4, wherein said signal peptide is the S. cerevisiae alpha mating factor signal sequence.

14. The isolated polynucleotide of claim 4, wherein said carbohydrate binding module is the carbohydrate binding module of T. reesei Cbh I, T. reesei Cbh2, Gibberella zeae Cbh2, Irpex lacteus Cbh2, Volvariella volvacea Cbh2, or Piromyces sp. Cbh2.

15. The isolated polynucleotide of claim 3, wherein said polynucleotide and said heterologous nucleic acid encode a fusion protein.

16. The isolated polynucleotide of claim 15, wherein said fusion protein is fused via a linker sequence.

17. The vector of claim 5, wherein the vector comprises the sequence of any one of SEQ ID NOs: 37-41.

18. The isolated polynucleotide of claim 1, wherein the cellobiohydrolase is a Cochliobolus heterostrophus or Volvariella volvacea cellobiohydrolase.

19. The isolated polynucleotide of claim 1, wherein at least 95% of the codons of said nucleic acid are codon-optimized for expression in the heterologous yeast host cell.

20. The isolated polynucleotide of claim 1, wherein about 100% of the codons of said nucleic acid are codon-optimized for expression in the heterologous yeast host cell.

* * * * *

SEQUENCE LISTING

<160> NUMBER OF SEQ ID NOS: 41

<210> SEQ ID NO 1
<211> LENGTH: 1369
<212> TYPE: DNA
<213> ORGANISM: Artificial Sequence
<220> FEATURE:
<223> OTHER INFORMATION: Cochliobolus heterostrophus C4 cel7

<400> SEQUENCE: 1

```
cttcttggtt ctcaaagatg ctctccaacg tctttcttac cgctgccctc gcagccggcc      60
tggctcaggc cctgccccag gccacgccta ccccaaccgc tgcgccctct ggcaacccct     120
tcgcgggcaa gaacttctac gccaacccat actactcgtc tgaagtccac accctggcca     180
tgccctcgct tccagcctcg ctgaagcctg ctgctaccgc cgtggccaag gtcggatcat     240
tcgtgtggat ggacaccatg gccaaggttc ctctcatgga cacctacctc gcagacatca     300
aggccaagaa cgctgctggc gcaaacctca tgggtacttt tgtcgtctac gaccttcccg     360
accgtgactg cgccgctctg gcctccaacg gtgaactcaa gattgacgag ggtggtgtcg     420
agaagtacaa gacccagtac attgacaaga ttgccgccat catcaagaag taccccgacg     480
tcaagatcaa ccttgccatt gagcccgatt cccttgccaa catggtcacc aacatgggtg     540
tgcagaagtg ctcgcgcgcc gccccatact acaaggagct cactgcctac gccctcaaga     600
cgctcaactt caacaacgtc gacatgtaca tggacgtgtg ccacgccggt tggctcggct     660
gggacgccaa cattggccct accgcaaagc ttttcgcaga ggtctacaag gctgctggct     720
ctccccgtgg cgtccgtggt atcgtcacca acgtcagcaa ctacaacgct ctccgcgtct     780
cctcctgccc atccatcacc caaggaaaca agaactgcga cgaggagcgc tacatcaacg     840
ccttggctcc tcttctcaag aacgagggtt tccctgctca cttcatcgtc gaccagggcc     900
gctccggaaa ggtgcctact aaccagcagg agtggggtga ctggtgcaac gtctcaggtg     960
```

```
ctggattcgg tacccgtccc accaccaaca ctggcaatgc cctcattgat gccatcgtct    1020
gggtcaagcc cggtggcgag tctgacggta cctctgacac cagcgctgcc cgctacgatg    1080
cccactgcgg caggaacagc gctttcaagc ccgctcctga ggctggaacc tggttccagg    1140
cttacttcga gatgcttctc aagaacgcta accctgctct tgcttaagtg tctggttctt    1200
ttgaataagc ttgggtagat tgttagaagg gaaaattagt ctgcgagtgg tctttcaccg    1260
cagattctgg tggattgtaa atatggcttt ggaactagaa taggcaacgt ttgatgttgc    1320
agttcgtgta aatattatac cttttggagc taaaaaaaaa aaaaaaaa                 1369

<210> SEQ ID NO 2
<211> LENGTH: 1581
<212> TYPE: DNA
<213> ORGANISM: Artificial Sequence
<220> FEATURE:
<223> OTHER INFORMATION: Gibberella zeae K59 cel6

<400> SEQUENCE: 2
atgacggcct acaagctttt cctggctgct gcttttgcag ccactgctct cgcagctcct      60
gttgaagagc gtcagtcttg cagcaacgga gtctggtgag tgtttgcagc catctttta     120 aagaattaat tactcacata cccataggtc tcaatgtggt ggtcagaact ggagcggtac     180
tccttgctgc accagtggaa acaagtgtgt caaggtcaac gacttctact cccaatgcca     240
gcctggatcc gcagacccct ctcccacgag caccattgtc agtgccacaa ccaccaaggc     300
tactaccact ggtagtggag gctctgtcac ctcgcctcct cctgttgcca ccaacaatcc     360
cttctctggc gttgatctgt gggccaacaa ctactaccgc tccgaggtca gcactctcgc     420
tatccccaag ctgagcggtg ccatggccac cgctgctgcc aaggtcgccg atgttccttc     480
tttccagtgg atgtgagtta cgagtccctt tggatatata cctctttact aaccacgata     540
gggacactta tgaccacatc tccttcatgg aggactctct tgccgatatc cgcaaggcca     600
acaaggctgg tggcaactac gctggtcagt cgtcgtccta cgatcttccc gaccgtgact     660
gtgctgctgc tgcctccaac ggagagtact cccttgacaa ggatggcaag aacaagtaca     720
aggcctacat tgcagatcaa gggatccttc aggactactc tgacacccgc atcattctcg     780
ttatcggtta gtccacctga ttgactccga cttagttcct actaacagcc atttagagcc     840
tgattctctt gctaacatgg tcaccaacat gaacgtcccc aagtgcgcca acgctgctag     900
cgcttacaag gagctcacca ttcacgccct caaggagctc aaccttccca acgtctccat     960
gtacatcgat gcaggtcacg gtggctggct gggatggccc gccaaccttc ctcctgccgc    1020
ccagctctac ggtcagctct acaaggatgc cggcaagcca tctcgcctcc gaggtctcgt    1080
caccaacgtc tccaactaca cgcctggaa gctgtcctcc aagcccgact acactgagag    1140
caaccccaac tacgacgagc agaagtacat ccacgctcta tctcctcttc tggagcagga    1200
gggctggccc ggtgccaagt catcgtcga ccagggccga tctggtaagc agcccactgg    1260
ccagaaggct tggggtgact ggtgcaacgc tcccggaact ggattcggtc ccgacccctc    1320
tgccaacact ggcgatgccc tcgtcgacgc tttcgtctgg gtcaagcctg tggtgagtc    1380 tgatggtacc tctgatacct ctgctgctcg ctacgactac cactgcggta ttgacggcgc    1440
tgtcaagtaa gttttataat acaaatcctc aagttaaccc tcatactaac cccgataact    1500
aggcccgctc ctgaggctgg aacctggttc caggcttact ttgagcagct tctcaagaac    1560 gccaaccccct ctttcctgta a                                             1581
```

-continued

```
<210> SEQ ID NO 3
<211> LENGTH: 2493
<212> TYPE: DNA
<213> ORGANISM: Artificial Sequence
<220> FEATURE:
<223> OTHER INFORMATION: Irpex lacteus MC-2 cex3

<400> SEQUENCE: 3
ccgcacccca gcatagcaac agcttttcg tcggcaagat attaagcacg gtcatggagt      60
tttcaacgac ttaaccgagc ttgtaccgaa gtggacggca gttcgctgaa cgttcgggtg     120 tgcttttac aacccgtcgt tgaaaataat gtgtaggtat ggccgtagcc tcatgacccc     180
actcataacg tccgtcgttc agcaactgac cctcccccga cgtctatccg ctaacaatgc     240
tcgggtctac gccggaatta tggtattctt ccactggtgg gcctgaacga tgcaaaacgg     300
tgcttctgat gagcccacct ctgtattatt tccggtatat aagaagtggt atcgtcggct     360
agggttctac aggatccaca tcccactgag acgaatccac tgcaagtgca atgaagtccg     420
ctgctttcct cgctgctctc gccgccatcc tcccagccta tgtcgctggc caagcccaga     480
cttgggcaca gtgcggtggt atcggcttca gtacgttact accttctcc ttctactggt      540 ctgttactta ctgaacttgc ctatcatagc tggtcctacc acttgcgttg ccggctccgt     600
ctgcacgaag cagaatgatt actactctca gtgcatgtaa gtacgaatcc accttttgc      660 aagaactact gacttatgat ggggtatagt cctggatctg ctactactcc cacatctgca     720
cctacatctg cacccacctc ccagccttcg cagccatctt ccacctcctc tgctccttcc     780
ggtccttcct ctaccccac gccctctgcc aacaacccat ggactggcta ccaggtatgc     840
gggcgatcca ttgtaactct aaaaatctct ttctgacctg acctgggcat agatctactt     900
gagcccttac tacgctaacg aggttgctgc cgccgccaag gcaatcacgg accccaccct     960
cgccgccaag gctgccagcg ttgctaacat cccgaacttc acttggttgg gtgagtgtga    1020
cattgacaag agaaggaaac gacttcctaa ttacccgcat agactccgtc tccaagatcg    1080
ctgatcttaa gacataccct gctgacgcaa gtgcactggg caagtccagc ggtcagaagc    1140
aactcctcca gattgtcgta tacgatcttc ccgaccgtga ttgcgctgct aaggcctcca    1200
atggagagtt cagcattgct gacaacggcc tggccaacta ccagaactac atcgaccaga    1260
tcgttgctgc tgtcaagcgt aagtctcgac gaggcagttc acttcgcttt gcatactgag    1320
cctgttcgcc acagaattcc ctgacgttcg ggtcgtggct gtcattgagc ccgactctct    1380
tgccaacttg gtcaccaact tgaacgtgca gaagtgcgct aacgccaaga gcacctacct    1440
cactgccgtc aactacgctt tgaagcagct ctcctcagtt ggcgtgtacc agtacatgga    1500
cgcaggtcac gccggatggc tcggttggcc cgccaacttg accccgccg ctcagctgtt     1560 cgctcaagtt tactctgatg ccggaaagtc gccattcatc aagggtcttg ctaccagtac    1620
gttttcattt cgttttgttc gatcactcaa gactgacccg cttgaatcgc aaagacgtcg    1680
ccaactacaa cgccttgagc gcggcctcac ccgatcccat cacccagggt gaccccaact    1740
acgatgaaat ccactacatc aacgtaagcc cgtttaaccg tacaatgcga tgtgtactaa    1800
tcaaaccaaa tcccgcaggc tctcgctccg gctctccagt ccgctggctt ccctgctacc    1860
ttcatcgtcg atcaaggccg ttccggtcag cagaaccacc gacaacagtg gggtgactgg    1920
tgcaacatca agggtgctgg gttcggtacc cgcccgacca ccaacactgg ttcttcgctc    1980
atcgactcca tcgtttgggt gaagcccgga ggtgaatccg acggtacctc gaactcgtct    2040
tcgccccgtt tcgactccac ttgctctttg gtaagttcgg ccttctgttc gtcaaactga    2100
```

```
gtgtgatgct aactcatcgt gcttgcagtc ggatgctact cagcccgctc ctgaggccgg    2160
tacatggttc caggcttact tcgagactct cgtctccaag ccaacccac cgctctaagc     2220 gtatcgtacc tgctttcaaa atgtggctga acggcataga acagctgctc ttggggttct    2280
cttcacttga tcgcgatttt tatataccctg tattttatgt agcataaaaa gtaaaacagc   2340
cgcagaaatg cattcgcttt tcacttgtac cgcgtcttgt tcttgtgcca aatgctctcg    2400
cgtcctaccg agttcatctt tcgatatcag tgagcggcca gcatcgaaac gaccactgcg    2460
ttagtttgtc tggcgacatc tgcatgcaag cta                                 2493

<210> SEQ ID NO 4
<211> LENGTH: 1453
<212> TYPE: DNA
<213> ORGANISM: Artificial Sequence
<220> FEATURE:
<223> OTHER INFORMATION: Volvariella volvacea cbhII-I

<400> SEQUENCE: 4
tgattgcaag ccacatatcc cagagatgtc caggttttct gctcttactg ctctcctttt    60
atctttgcca ctactggcta ttgctcagtc cccgttgtat gggcaatgtg gtggcaacgg    120
ctggactggc ccaaagacct gtgtatcagg tgcaacttgt acagtgatca atgactggta    180
ttggcaatgc ctgccaggaa atggcccaac ttcttcttca ccaacttcca cacctaccac    240
caccacaact acaggggac ctcaaccaac cgtaccagca gcagggaatc cttatactgg     300
atacgagatt tacttgagtc cttattacgc tgctgaggct caagctgcgg ctgcccaaat    360
ttctgatgcc acgcagaagg ccaaagccct gaaggtcgca caaatcccca cattcacctg    420
gtttgatgtt attgcaaaga cctccacact cggtgattat ttggccgaag cgagcgcact    480
tgggaaatcc tctggaaaga aatacctcgt tcaaatcgtt gtatatgact tgccagatcg    540
ggattgcgct gctctggctt cgaatggaga gtttagcatc gcaaacaatg gctcaacaa    600 ctacaagggc tacatcgatc aattggttgc tcagatcaag aaatacctg atgtccgagt     660 cgtggctgtt attgaacccg actccttggc caatctcgtt accaatctca atgttagcaa    720
gtgtgccaat gcacaaacag cctacaaggc tggtgtcacg tacgctctcc agcagctcaa    780
ctctgttggc gtctatatgt acctcgatgc tggacatgcg ggttggctcg gatggcctgc    840
caacttgaat cccgctgcgc aactgttctc tcaattgtac agagatgctg gaagtcccca    900
atatgtccgt ggcctagcta ccaatgttgc caactacaac gcactctctg ccagcagccc    960
cgacccagtc acacaaggca atcccaacta tgacgaactt cattacatca acgcactcgc    1020
gccagctctc caatccggtg gcttccctgc ccacttcatt gtcgaccaag gccgatcagg    1080
agttcagaac atcagacaac aatggggcga ctggtgcaac gtcaagggtg caggctttgg    1140
ccagcgtcca actcttagca caggttcatc ccttatcgac gccattgtct ggattaaacc    1200
cggaggcgaa tgcgacggta caaccaacac atcgtcacct cgctatgatt ctcactgtgg    1260
tctttctgat gctacacccca atgccccaga agctggccaa tggttccagg cttacttcga    1320
gaccttagtc cgtaacgcca gcccaccctct ttgagtgtgc agtgtagata ccagatatac    1380
aaggccccga gtgtgataca acagaataaa taatccctt ttgctcctct caaaaaaaaa     1440
aaaaaaaaaa aaa                                                       1453

<210> SEQ ID NO 5
<211> LENGTH: 1920
<212> TYPE: DNA
<213> ORGANISM: Artificial Sequence
```

<220> FEATURE:
<223> OTHER INFORMATION: Piromyces sp. E2 cel6A
<220> FEATURE:
<221> NAME/KEY: misc_feature
<222> LOCATION: (1886)..(1886)
<223> OTHER INFORMATION: n is a, c, g, or t
<220> FEATURE:
<221> NAME/KEY: misc_feature
<222> LOCATION: (1906)..(1906)
<223> OTHER INFORMATION: n is a, c, g, or t

<400> SEQUENCE: 5

```
aaatcttaat tataattaat aatatcattt tcatttatt atatttatac tttgtttcat    60
gaaataataa taaacaacat tttcccaata gttttaaaat catttttac ttttctcaaa    120
tttatcgaac aattaaaaac tataaaagga gcaattttc atttaatta ttttcttcat    180
taattaaaaa attattttct ctggaagaaa ataaatataa tagaaaaaaa taaaagaaa    240
aggaaattac aaaaaaacaa aattaaataa tatatattga tttatatatt aattaaaaat    300
aatatatttt taaatttatt atcaacaaaa aaaaaaaatt tttaatcaaa aaatgaaggc    360
ttctattgct ttaactgcta ttgccgctct tgctgctaac gcttctgctg cttgtttctc    420
tgaaagactt ggttatccat gttgcagagg taatgaagtt ttttacaccg ataatgatgg    480
tgattggggt gttgaaaatg gtaactggtg tggtattggt ggtgcttctg ctactacctg    540
ctggtctcaa gctttaggtt acccatgttg tacttctact tccgatgttg cctatgttga    600
tggtgatggc aattggggtg ttgaaaatgg taattggtgt ggtattattg ctggtggtaa    660
ttcaagcaac aacaacagtg gtagtaccat taatgttggt gatgttacca ttggtaatca    720
atacactcac actggtaatc cattcgctgg tcacaaattc ttcattaatc catactacac    780
tgctgaagtc gatggtgcca tcgctcaaat ttctaacgct tctcttagag ctaaggctga    840
aaaaatgaaa gaattctcta atgctatctg gttagatact attaagaata tgaatgaatg    900
gttagaaaag aatcttaaat acgctcttgc tgaacaaaat gaaactggta agaccgtttt    960
aaccgttttc gttgtttacg atttaccagg tcgtgattgt catgctcttg cttccaatgg   1020
tgaacttctt gccaacgaca gtgattgggc tcgttaccaa tcggaataca ttgatgtcat   1080
tgaagaaaaa ttaaagactt acaagagtca accagttgtt cttgttgttg aaccagattc   1140
tcttgctaac atggttacta atcttgattc tactccagct tgtcgtgatt ctgaaaagta   1200
ttacatggat ggtcatgctt acttaattaa aaagcttggt gttcttccac atgttgctat   1260
gtaccttgat attggtcatg ctttctggtt aggatgggat gataaccgtt taaaggctgg   1320
taaggtttac tccaaggtta ttcaatctgg tgctccaggt aatgttcgtg gtttcgcttc   1380
taacgttgct aactacactc catgggaaga tccaactctt tctcgtggtc agacactga   1440
atggaatcca tgtccagatg aaaagagata cattgaagcc atgtacaagg acttcaagtc   1500
tgctggtatt aaatccgttt acttcattga tgatacttct cgtaatggtc acaaaaccga   1560
ccgtactcat ccaggagaat ggtgtaacca accggagtt ggtattggtg ctcgtccaca   1620
agccaatcca atctctggta tggactacct tgatgctttc tactgggtta aaccactcgg   1680
tgaatccgat ggttactccg atactacagc cgttcgttat gatggttatt gtggtcatgc   1740
tactgccatg aaaccagcac cagaagccgg tcaatggttc caaaagcact tgaacaagg   1800
tcttgaaaat gctaatccac cactctaatc atattaacat taaataatat acattatata   1860
catatagaaa gaaacatgaa tattantatt aacataatca tacttnttaa ataaattatt   1920
```

<210> SEQ ID NO 6

<211> LENGTH: 1190
<212> TYPE: DNA
<213> ORGANISM: Artificial Sequence
<220> FEATURE:
<223> OTHER INFORMATION: Cochliobolus heterostrophus C4 cel7

<400> SEQUENCE: 6

| | | | | | |
|---|---|---|---|---|---|
| ttaattaaaa | tgttgtctaa | cgttttttg | actgctgctt | tggctgctgg | tttggctcaa | 60 |
| gctttgccac | aagctactcc | aactccaact | gctgctccat | ctggtaatcc | atttgctggt | 120 |
| aagaattttt | acgctaaccc | atattattct | tcagaagttc | atactttggc | tatgccatct | 180 |
| ttgccagctt | cattgaaacc | agctgctact | gctgttgcta | agttggttc | ttttgtttgg | 240 |
| atggatacta | tggctaaagt | tccattgatg | gatacttact | tggctgatat | aaagctaaa | 300 |
| aatgctgctg | gtgctaattt | gatgggtact | ttcgttgttt | atgatttgcc | agatagagat | 360 |
| tgtgctgctt | tagcttctaa | tggtgaattg | aaaattgatg | aaggtggtgt | tgaaaaatac | 420 |
| aagacacaat | acattgataa | gattgctgct | attatcaaaa | agtacccaga | tgttaagatt | 480 |
| aatttggcta | ttgaaccaga | ttcttttggct | aatatgggtta | ctaatatggg | tgttcaaaaa | 540 |
| tgttctagag | ctgctccata | ttacaaagaa | ttgactgctt | atgctttgaa | aactttgaac | 600 |
| ttcaacaacg | ttgacatgta | tatggatggt | ggtcatgctg | ttggttggg | ttgggatgct | 660 |
| aatattggtc | aactgctaa | attgtttgct | gaagtttaca | agctgctgg | ttctccaaga | 720 |
| ggtgttagag | gtattgttac | aaacgtttct | aattacaacg | ctttgagagt | ttcttcttgt | 780 |
| ccatctatta | ctcaaggtaa | caagaattgt | gatgaagaaa | gatacattaa | tgctttggct | 840 |
| ccattgttga | aaaatgaagg | ttttccagct | cattttattg | ttgatcaagg | tagatcaggt | 900 |
| aaagttccaa | ctaatcaaca | agaatggggt | gattggtgta | atgtttctgg | tgctggtttt | 960 |
| ggtactagac | caactactaa | tactggtaat | gctttgattg | atgctattgt | ttgggttaaa | 1020 |
| ccaggtggtg | aatctgatgg | tacttctgat | acttctgctg | caagatatga | tgctcattgt | 1080 |
| ggtagaaatt | ctgcttttaa | accagctcca | gaagctggta | cttggtttca | agcttacttt | 1140 |
| gaaatgttgt | tgaagaatgc | taatccagct | ttggcattat | aaggcgcgcc | | 1190 |

<210> SEQ ID NO 7
<211> LENGTH: 1394
<212> TYPE: DNA
<213> ORGANISM: Artificial Sequence
<220> FEATURE:
<223> OTHER INFORMATION: Gibberella zeae K59 cel6

<400> SEQUENCE: 7

| | | | | | |
|---|---|---|---|---|---|
| ttaattaaaa | tgactgctta | caaattgttt | ttggctgctg | cttttgctgc | tactgctttg | 60 |
| gctgctccag | ttgaagaaag | acaatcttgt | tctaatggtg | tttggtcaca | atgtggtggt | 120 |
| caaaattggt | ctggtactcc | atgttgtaca | tctggtaaca | agtgtgttaa | ggttaatgat | 180 |
| ttctactctc | aatgtcaacc | aggttctgct | gatccatctc | caacttctac | tattgtttct | 240 |
| gctactacta | ctaaagctac | tactacaggt | tctggtggtt | ctgttacttc | tccaccacca | 300 |
| gttgctacaa | acaatccatt | ttctggtgtt | gatttgtggg | caaacaatta | ttacagatca | 360 |
| gaagtttcta | ctttggctat | tccaaaattg | tctggtgcta | tggctactgc | tgctgcaaaa | 420 |
| gttgctgatg | ttccatcttt | tcaatggatg | gatacttacg | atcatatttc | tttcatggaa | 480 |
| gattctttgg | ctgatattag | aaaagcaaac | aaagcaggtg | gtaattatgc | tggtcaattc | 540 |
| gttgtttatg | atttgccaga | tagagattgt | gctgctgctg | cttctaatgg | tgaatactct | 600 |
| ttggataaag | atggtaaaaa | caagtacaaa | gcttatattg | ctgatcaagg | tattttgcaa | 660 |

```
gattactctg atactagaat cattttggtt attgaaccag attctttagc taacatggtt    720
actaatatga atgttccaaa atgtgctaat gctgcttctg cttacaaaga attgactatt    780
catgctttga aagaattgaa tttgccaaac gtttcaatgt atattgatgc tggtcatggt    840
ggttggttgg gttggccagc taatttgcca cctgctgctc aattgtatgg tcaattgtac    900
aaagatgctg gtaaaccatc tagattgaga ggtttggtta ctaatgtttc taattacaac    960
gcttggaaat tatcttctaa gccagattat actgaatcta acccaaatta cgatgaacaa   1020
aagtacattc atgctttatc tccattgttg gaacaagaag gttggccagg cgctaagttc   1080
attgttgatc aaggtagatc aggtaaacaa ccaactggtc aaaaagcttg gggtgattgg   1140
tgtaatgctc caggtactgg ttttggttta agaccatctg ctaatactgg tgatgctttg   1200
gttgatgctt ttgtttgggt taaaccaggt ggtgaatctg atggtacttc tgatacttct   1260
gctgcaagat atgattatca ttgtggtatt gatggtgctg ttaaaccagc tccagaagct   1320
ggtacttggt ttcaagctta ctttgaacaa ttgttgaaga atgctaatcc atcttcttg    1380 ttataaggcg cgcc                                                    1394
```

<210> SEQ ID NO 8
<211> LENGTH: 1379
<212> TYPE: DNA
<213> ORGANISM: Artificial Sequence
<220> FEATURE:
<223> OTHER INFORMATION: Irpex lacteus MC-2 cex3

<400> SEQUENCE: 8

```
ttaattaaaa tgaagtctgc tgctttttg gctgctttag ctgctatttt gccagcttac      60
gttgctggtc aagctcaaac ttgggctcaa tgtggtggta ttggttttac tggtccaact    120
acttgtgttg ctggttctgt ttgtactaaa caaaacgatt actactctca atgtattcca    180
ggttctgcta ctactccaac ttctgctcca acatctgcac caacttctca accatcacaa    240
ccatcttcta cttcatctgc tccatctggt ccatcttcta caccaactcc atctgctaac    300
aatccatgga ctggttatca aatttacttg tctccatact atgctaatga agttgctgca    360
gctgctaaag ctattactga tccaactttg gctgctaaag cagcttctgt tgctaatatt    420
ccaaatttca cttggttgga ttctgttttct aaaattgctg atttgaaaac ttatttggct    480
gatgcttctg cttttgggta aatcttctggt caaaagcaat gttgcaaat tgttgtttat    540 gatttgccag atagagattg tgctgcaaaa gcttctaatg gtgaatttc tattgctgat    600 aatggttttg ctaactacca aaactacatt gatcaaattg ttgctgctgt taaacaattt    660
ccagatgtta gagttgttgc tgttattgaa ccagattctt ggctaatttt ggttacaaat    720
ttaaacgttc aaaagtgtgc taatgctaaa tctacttact tgactgctgt taattatgct    780
ttgaagcaat tatcttctgt tggtgtttat caatatatgg atgctggtca tgctggttgg    840
ttgggttggc cagctaattt aactccagct gctcaattgt ttgctcaagt ttattctgat    900
gctggtaaat ctccattcat taagggtttg gctactaatg ttgctaatta caatgctttg    960
tctgctgctt ctccagatcc aattactcaa ggtgatccaa attacgatga aattcattac   1020
attaatgctt tggctccagc tttgcaatct gctggttttc cagctacttt tattgttgat   1080
caaggtagat caggtcaaca aaatcataga caacaatggg gtgattggtg taacattaaa   1140
ggtgctggtt ttggtactag accaactact aatactggtt cttcttttgat tgattctatt   1200 gtttgggtta aaccaggtgg tgaatctgat ggtacttcta attcttcatc tccaagattt   1260
```

| | |
|---|---|
| gattctactt gttctttgtc tgatgctact caaccagctc cagaagctgg tacttggttt | 1320 |
| caagcttact ttgaaacttt ggtttctaaa gctaatccac cattgttata aggcgcgcc | 1379 |

<210> SEQ ID NO 9
<211> LENGTH: 1349
<212> TYPE: DNA
<213> ORGANISM: Artificial Sequence
<220> FEATURE:
<223> OTHER INFORMATION: Volvariella volvacea cbhII-I

<400> SEQUENCE: 9

| | |
|---|---|
| ttaattaaaa tgtctagatt ctctgctttg actgctttgt tgttgtcttt gccattgttg | 60 |
| gctattgctc aatctccatt gtatggtcaa tgtggtggta atggttggac tggtccaaaa | 120 |
| acttgtgttt ctggtgctac ttgtactgtt attaatgatt ggtattggca atgtttgcca | 180 |
| ggtaatggtc caacttcttc ttctccaact tctactccaa ctacaactac tactactggt | 240 |
| ggtccacaac caactgttcc agctgctggt aatccatata ctggttacga aatttacttg | 300 |
| tctccatatt atgctgctga agctcaagct gctgctgctc aaatttctga tgctactcaa | 360 |
| aaagctaaag cttttgaaagt tgctcaaatt ccaacttttta cttggtttga tgttattgct | 420 |
| aaaacttcta ctttgggtga ttatttggct gaagcttctg ctttgggtaa atcttctggt | 480 |
| aaaaagtact tggttcaaat tgttgtttat gatttgccag atagagattg tgctgctttg | 540 |
| gcttctaatg gtgaattttc tattgctaac aacggtttga caattacaa aggttacatt | 600 |
| gatcaattgg ttgcacaaat taagaaatac ccagatgtta gagttgttgc tgttattgaa | 660 |
| ccagattctt tggctaattt ggttacaaat ttgaacgttt ctaagtgtgc taatgctcaa | 720 |
| actgcttaca agctggtgt tacttatgct ttgcaacaat tgaactctgt tggtgtttac | 780 |
| atgtatttgg atgctggtca tgctggttgg ttgggttggc cagctaatttt gaatccagct | 840 |
| gctcaattgt tttctcaatt gtatagagat gctggttctc cacaatacgt tagaggtttg | 900 |
| gctactaatg ttgctaatta caatgctttg tctgcttctt caccagatcc agttactcaa | 960 |
| ggtaatccaa attacgatga attgcattac attaatgctt tggctccagc tttgcaatct | 1020 |
| ggtggttttc cagctcattt tattgttgat caaggtagat caggtgttca aaacattaga | 1080 |
| caacaatggg gtgattggtg taatgttaaa ggtgctggtt ttggtcaaag accaactta | 1140 |
| tctactggtt cttctttgat tgatgctatt gtttggatta accaggtgg tgaatgtgat | 1200 |
| ggtactacta atacatcttc tccaagatat gattctcatt gtggtttgtc tgatgctact | 1260 |
| ccaaatgctc ctgaagctgg tcaatggttt caagcttact ttgaaacttt ggttagaaat | 1320 |
| gcttctccac cattgttata aggcgcgcc | 1349 |

<210> SEQ ID NO 10
<211> LENGTH: 1496
<212> TYPE: DNA
<213> ORGANISM: Artificial Sequence
<220> FEATURE:
<223> OTHER INFORMATION: Piromyces sp. E2 cel6A

<400> SEQUENCE: 10

| | |
|---|---|
| ttaattaaaa tgaaggcttc tattgctttg actgctattg ctgctttggc tgctaatgct | 60 |
| tctgctgctt gtttttctga aagattgggt tatccatgtt gtagaggtaa tgaagttttc | 120 |
| tacactgata tgatggtga ttggggtgtt gaaaatggta attggtgtgg tattggtggt | 180 |
| gcttctgcta ctacttgttg gtcacaagct ttaggttacc cttgttgtac ttctacttct | 240 |
| gatgttgctt acgttgatgg tgacggtaac tggggtgtcg aaaacggtaa ctggtgcggt | 300 |

-continued

```
ataattgcag gtggtaattc ttctaacaac aactctggtt ctactattaa tgttggtgat    360
gttactattg gtaaccaata cactcatact ggtaatccat ttgctggtca taaattcttt    420
attaacccat actatactgc tgaagttgat ggtgctattg ctcaaatttc taatgcttct    480
ttgagagcta aagctgaaaa gatgaaagaa ttttctaacg ctatttggtt ggatactatt    540
aagaatatga acgaatggtt ggaaaagaat ttgaaatatg ctttggctga caaaatgaa    600 actggtaaga ctgttttgac agttttttgtt gtttatgatt tgccaggtag agattgtcat    660
gctttagctt ctaatggtga attgttggct aatgattctg attgggcaag atatcaatct    720
gaatacattg atgttattga agaaaagttg aaaacttaca agtctcaacc agttgttttg    780
gttgttgaac cagattcttt ggctaatatg gttacaaatt tggattctac tccagcttgt    840
agagattctg aaaaatacta tatggatggt catgcttact tgattaaaaa gttgggtgtt    900
ttgccacatg ttgcaatgta tttggatatt ggtcatgctt tttggttggg ttgggatgat    960
aatagattga agctggtaa agtttactct aaggttattc aatctggtgc tccaggtaat   1020
gttagaggtt ttgcttctaa tgttgctaat tatactccat gggaagatcc aactttgtct   1080
agaggtccag atactgaatg gaatccatgt ccagatgaaa aaagatacat tgaagcaatg   1140
tacaaagatt ttaagtctgc tggtattaag tctgtttact tcattgatga tacttctaga   1200
aatggtcata agactgatag aactcatcca ggtgaatggt gtaatcaaac aggtgttggt   1260
attggtgcta gaccacaagc taatccaatt tctggtatgg attacttgga tgcttttat    1320 tgggttaaac cattgggtga atctgatggt tattctgata ctactgctgt cagatatgat   1380
ggttattgtg gtcatgctac tgctatgaaa ccagctcctg aagctggtca atggtttcaa   1440
aaacatttcg aacaaggttt ggaaaatgct aatccaccat tgttataagg cgcgcc       1496
```

<210> SEQ ID NO 11
<211> LENGTH: 389
<212> TYPE: PRT
<213> ORGANISM: Cochliobolus heterostrophus

<400> SEQUENCE: 11

```
Met Leu Ser Asn Val Phe Leu Thr Ala Ala Leu Ala Ala Gly Leu Ala
1               5                   10                  15

Gln Ala Leu Pro Gln Ala Thr Pro Thr Pro Thr Ala Ala Pro Ser Gly
            20                  25                  30

Asn Pro Phe Ala Gly Lys Asn Phe Tyr Ala Asn Pro Tyr Tyr Ser Ser
        35                  40                  45

Glu Val His Thr Leu Ala Met Pro Ser Leu Pro Ala Ser Leu Lys Pro
    50                  55                  60

Ala Ala Thr Ala Val Ala Lys Val Gly Ser Phe Val Trp Met Asp Thr
65                  70                  75                  80

Met Ala Lys Val Pro Leu Met Asp Thr Tyr Leu Ala Asp Ile Lys Ala
                85                  90                  95

Lys Asn Ala Ala Gly Ala Asn Leu Met Gly Thr Phe Val Val Tyr Asp
            100                 105                 110

Leu Pro Asp Arg Asp Cys Ala Ala Leu Ala Ser Asn Gly Glu Leu Lys
        115                 120                 125

Ile Asp Glu Gly Gly Val Glu Lys Tyr Lys Thr Gln Tyr Ile Asp Lys
    130                 135                 140

Ile Ala Ala Ile Ile Lys Lys Tyr Pro Asp Val Lys Ile Asn Leu Ala
145                 150                 155                 160
```

```
Ile Glu Pro Asp Ser Leu Ala Asn Met Val Thr Asn Met Gly Val Gln
            165                 170                 175

Lys Cys Ser Arg Ala Ala Pro Tyr Tyr Lys Glu Leu Thr Ala Tyr Ala
            180                 185                 190

Leu Lys Thr Leu Asn Phe Asn Asn Val Asp Met Tyr Met Asp Gly Gly
            195                 200                 205

His Ala Gly Trp Leu Gly Trp Asp Ala Asn Ile Gly Pro Thr Ala Lys
            210                 215                 220

Leu Phe Ala Glu Val Tyr Lys Ala Gly Ser Pro Arg Gly Val Arg
225                 230                 235                 240

Gly Ile Val Thr Asn Val Ser Asn Tyr Asn Ala Leu Arg Val Ser Ser
            245                 250                 255

Cys Pro Ser Ile Thr Gln Gly Asn Lys Asn Cys Asp Glu Glu Arg Tyr
            260                 265                 270

Ile Asn Ala Leu Ala Pro Leu Leu Lys Asn Glu Gly Phe Pro Ala His
            275                 280                 285

Phe Ile Val Asp Gln Gly Arg Ser Gly Lys Val Pro Thr Asn Gln Gln
            290                 295                 300

Glu Trp Gly Asp Trp Cys Asn Val Ser Gly Ala Gly Phe Gly Thr Arg
305                 310                 315                 320

Pro Thr Thr Asn Thr Gly Asn Ala Leu Ile Asp Ala Ile Val Trp Val
            325                 330                 335

Lys Pro Gly Gly Glu Ser Asp Gly Thr Ser Asp Thr Ser Ala Ala Arg
            340                 345                 350

Tyr Asp Ala His Cys Gly Arg Asn Ser Ala Phe Lys Pro Ala Pro Glu
            355                 360                 365

Ala Gly Thr Trp Phe Gln Ala Tyr Phe Glu Met Leu Leu Lys Asn Ala
            370                 375                 380

Asn Pro Ala Leu Ala
385

<210> SEQ ID NO 12
<211> LENGTH: 457
<212> TYPE: PRT
<213> ORGANISM: Gibberella zeae

<400> SEQUENCE: 12

Met Thr Ala Tyr Lys Leu Phe Leu Ala Ala Phe Ala Ala Thr Ala
1               5                   10                  15

Leu Ala Ala Pro Val Glu Glu Arg Gln Ser Cys Ser Asn Gly Val Trp
            20                  25                  30

Ser Gln Cys Gly Gly Gln Asn Trp Ser Gly Thr Pro Cys Cys Thr Ser
            35                  40                  45

Gly Asn Lys Cys Val Lys Val Asn Asp Phe Tyr Ser Gln Cys Gln Pro
        50                  55                  60

Gly Ser Ala Asp Pro Ser Pro Thr Ser Thr Ile Val Ser Ala Thr Thr
65                  70                  75                  80

Thr Lys Ala Thr Thr Thr Gly Ser Gly Gly Ser Val Thr Ser Pro Pro
            85                  90                  95

Pro Val Ala Thr Asn Asn Pro Phe Ser Gly Val Asp Leu Trp Ala Asn
            100                 105                 110

Asn Tyr Tyr Arg Ser Glu Val Ser Thr Leu Ala Ile Pro Lys Leu Ser
            115                 120                 125

Gly Ala Met Ala Thr Ala Ala Ala Lys Val Ala Asp Val Pro Ser Phe
            130                 135                 140
```

```
Gln Trp Met Asp Thr Tyr Asp His Ile Ser Phe Met Glu Asp Ser Leu
145                 150                 155                 160

Ala Asp Ile Arg Lys Ala Asn Lys Ala Gly Gly Asn Tyr Ala Gly Gln
                165                 170                 175

Phe Val Val Tyr Asp Leu Pro Asp Arg Asp Cys Ala Ala Ala Ala Ser
            180                 185                 190

Asn Gly Glu Tyr Ser Leu Asp Lys Asp Gly Lys Asn Lys Tyr Lys Ala
        195                 200                 205

Tyr Ile Ala Asp Gln Gly Ile Leu Gln Asp Tyr Ser Asp Thr Arg Ile
    210                 215                 220

Ile Leu Val Ile Glu Pro Asp Ser Leu Ala Asn Met Val Thr Asn Met
225                 230                 235                 240

Asn Val Pro Lys Cys Ala Asn Ala Ala Ser Ala Tyr Lys Glu Leu Thr
                245                 250                 255

Ile His Ala Leu Lys Glu Leu Asn Leu Pro Asn Val Ser Met Tyr Ile
            260                 265                 270

Asp Ala Gly His Gly Gly Trp Leu Gly Trp Pro Ala Asn Leu Pro Pro
        275                 280                 285

Ala Ala Gln Leu Tyr Gly Gln Leu Tyr Lys Asp Ala Gly Lys Pro Ser
    290                 295                 300

Arg Leu Arg Gly Leu Val Thr Asn Val Ser Asn Tyr Asn Ala Trp Lys
305                 310                 315                 320

Leu Ser Ser Lys Pro Asp Tyr Thr Glu Ser Asn Pro Asn Tyr Asp Glu
                325                 330                 335

Gln Lys Tyr Ile His Ala Leu Ser Pro Leu Leu Glu Gln Glu Gly Trp
            340                 345                 350

Pro Gly Ala Lys Phe Ile Val Asp Gln Gly Arg Ser Gly Lys Gln Pro
        355                 360                 365

Thr Gly Gln Lys Ala Trp Gly Asp Trp Cys Asn Ala Pro Gly Thr Gly
    370                 375                 380

Phe Gly Leu Arg Pro Ser Ala Asn Thr Gly Asp Ala Leu Val Asp Ala
385                 390                 395                 400

Phe Val Trp Val Lys Pro Gly Gly Glu Ser Asp Gly Thr Ser Asp Thr
                405                 410                 415

Ser Ala Ala Arg Tyr Asp Tyr His Cys Gly Ile Asp Gly Ala Val Lys
            420                 425                 430

Pro Ala Pro Glu Ala Gly Thr Trp Phe Gln Ala Tyr Phe Glu Gln Leu
        435                 440                 445

Leu Lys Asn Ala Asn Pro Ser Phe Leu
    450                 455

<210> SEQ ID NO 13
<211> LENGTH: 457
<212> TYPE: PRT
<213> ORGANISM: Irpex lacteus

<400> SEQUENCE: 13

Met Thr Ala Tyr Lys Leu Phe Leu Ala Ala Ala Phe Ala Ala Thr Ala
1               5                   10                  15

Leu Ala Ala Pro Val Glu Glu Arg Gln Ser Cys Ser Asn Gly Val Trp
            20                  25                  30

Ser Gln Cys Gly Gly Gln Asn Trp Ser Gly Thr Pro Cys Cys Thr Ser
        35                  40                  45

Gly Asn Lys Cys Val Lys Val Asn Asp Phe Tyr Ser Gln Cys Gln Pro
```

```
            50                  55                  60
Gly Ser Ala Asp Pro Ser Pro Thr Ser Thr Ile Val Ser Ala Thr Thr
 65                  70                  75                  80

Thr Lys Ala Thr Thr Thr Gly Ser Gly Gly Ser Val Thr Ser Pro Pro
                 85                  90                  95

Pro Val Ala Thr Asn Asn Pro Phe Ser Gly Val Asp Leu Trp Ala Asn
             100                 105                 110

Asn Tyr Tyr Arg Ser Glu Val Ser Thr Leu Ala Ile Pro Lys Leu Ser
             115                 120                 125

Gly Ala Met Ala Thr Ala Ala Lys Val Ala Asp Val Pro Ser Phe
         130                 135                 140

Gln Trp Met Asp Thr Tyr Asp His Ile Ser Phe Met Glu Asp Ser Leu
145                 150                 155                 160

Ala Asp Ile Arg Lys Ala Asn Lys Ala Gly Gly Asn Tyr Ala Gly Gln
                 165                 170                 175

Phe Val Val Tyr Asp Leu Pro Asp Arg Asp Cys Ala Ala Ala Ala Ser
             180                 185                 190

Asn Gly Glu Tyr Ser Leu Asp Lys Asp Gly Lys Asn Lys Tyr Lys Ala
             195                 200                 205

Tyr Ile Ala Asp Gln Gly Ile Leu Gln Asp Tyr Ser Asp Thr Arg Ile
210                 215                 220

Ile Leu Val Ile Glu Pro Asp Ser Leu Ala Asn Met Val Thr Asn Met
225                 230                 235                 240

Asn Val Pro Lys Cys Ala Asn Ala Ala Ser Ala Tyr Lys Glu Leu Thr
                 245                 250                 255

Ile His Ala Leu Lys Glu Leu Asn Leu Pro Asn Val Ser Met Tyr Ile
                 260                 265                 270

Asp Ala Gly His Gly Gly Trp Leu Gly Trp Pro Ala Asn Leu Pro Pro
                 275                 280                 285

Ala Ala Gln Leu Tyr Gly Gln Leu Tyr Lys Asp Ala Gly Lys Pro Ser
             290                 295                 300

Arg Leu Arg Gly Leu Val Thr Asn Val Ser Asn Tyr Asn Ala Trp Lys
305                 310                 315                 320

Leu Ser Ser Lys Pro Asp Tyr Thr Glu Ser Asn Pro Asn Tyr Asp Glu
                 325                 330                 335

Gln Lys Tyr Ile His Ala Leu Ser Pro Leu Leu Glu Gln Glu Gly Trp
             340                 345                 350

Pro Gly Ala Lys Phe Ile Val Asp Gln Gly Arg Ser Gly Lys Gln Pro
             355                 360                 365

Thr Gly Gln Lys Ala Trp Gly Asp Trp Cys Asn Ala Pro Gly Thr Gly
         370                 375                 380

Phe Gly Leu Arg Pro Ser Ala Asn Thr Gly Asp Ala Leu Val Asp Ala
385                 390                 395                 400

Phe Val Trp Val Lys Pro Gly Gly Glu Ser Asp Gly Thr Ser Asp Thr
                 405                 410                 415

Ser Ala Ala Arg Tyr Asp Tyr His Cys Gly Ile Asp Gly Ala Val Lys
                 420                 425                 430

Pro Ala Pro Glu Ala Gly Thr Trp Phe Gln Ala Tyr Phe Glu Gln Leu
                 435                 440                 445

Leu Lys Asn Ala Asn Pro Ser Phe Leu
450                 455
```

<210> SEQ ID NO 14

```
<211> LENGTH: 442
<212> TYPE: PRT
<213> ORGANISM: Volvariella volvacea

<400> SEQUENCE: 14
```

| | | | | | | | | | | | | | | |
|---|---|---|---|---|---|---|---|---|---|---|---|---|---|---|
| Met | Ser | Arg | Phe | Ser | Ala | Leu | Thr | Ala | Leu | Leu | Ser | Leu | Pro | Leu |
| 1 | | | | 5 | | | | | 10 | | | | | 15 |
| Leu | Ala | Ile | Ala | Gln | Ser | Pro | Leu | Tyr | Gly | Gln | Cys | Gly | Gly | Asn | Gly |
| | | | 20 | | | | | 25 | | | | | 30 | | |
| Trp | Thr | Gly | Pro | Lys | Thr | Cys | Val | Ser | Gly | Ala | Thr | Cys | Thr | Val | Ile |
| | | | 35 | | | | | 40 | | | | | 45 | | |
| Asn | Asp | Trp | Tyr | Trp | Gln | Cys | Leu | Pro | Gly | Asn | Gly | Pro | Thr | Ser | Ser |
| | 50 | | | | | 55 | | | | | 60 | | | | |
| Ser | Pro | Thr | Ser | Thr | Pro | Thr | Thr | Thr | Thr | Thr | Gly | Gly | Pro | Gln |
| 65 | | | | | 70 | | | | | 75 | | | | | 80 |
| Pro | Thr | Val | Pro | Ala | Ala | Gly | Asn | Pro | Tyr | Thr | Gly | Tyr | Glu | Ile | Tyr |
| | | | | 85 | | | | | 90 | | | | | 95 | |
| Leu | Ser | Pro | Tyr | Tyr | Ala | Ala | Glu | Ala | Gln | Ala | Ala | Ala | Gln | Ile |
| | | | | 100 | | | | | 105 | | | | | 110 | |
| Ser | Asp | Ala | Thr | Gln | Lys | Ala | Lys | Ala | Leu | Lys | Val | Ala | Gln | Ile | Pro |
| | | 115 | | | | | 120 | | | | | 125 | | | |
| Thr | Phe | Thr | Trp | Phe | Asp | Val | Ile | Ala | Lys | Thr | Ser | Thr | Leu | Gly | Asp |
| | 130 | | | | | 135 | | | | | 140 | | | | |
| Tyr | Leu | Ala | Glu | Ala | Ser | Ala | Leu | Gly | Lys | Ser | Ser | Gly | Lys | Lys | Tyr |
| 145 | | | | | 150 | | | | | 155 | | | | | 160 |
| Leu | Val | Gln | Ile | Val | Val | Tyr | Asp | Leu | Pro | Asp | Arg | Asp | Cys | Ala | Ala |
| | | | 165 | | | | | 170 | | | | | 175 | | |
| Leu | Ala | Ser | Asn | Gly | Glu | Phe | Ser | Ile | Ala | Asn | Asn | Gly | Leu | Asn | Asn |
| | | 180 | | | | | 185 | | | | | 190 | | | |
| Tyr | Lys | Gly | Tyr | Ile | Asp | Gln | Leu | Val | Ala | Gln | Ile | Lys | Lys | Tyr | Pro |
| | | 195 | | | | | 200 | | | | | 205 | | | |
| Asp | Val | Arg | Val | Val | Ala | Val | Ile | Glu | Pro | Asp | Ser | Leu | Ala | Asn | Leu |
| | 210 | | | | | 215 | | | | | 220 | | | | |
| Val | Thr | Asn | Leu | Asn | Val | Ser | Lys | Cys | Ala | Asn | Ala | Gln | Thr | Ala | Tyr |
| 225 | | | | | 230 | | | | | 235 | | | | | 240 |
| Lys | Ala | Gly | Val | Thr | Tyr | Ala | Leu | Gln | Gln | Leu | Asn | Ser | Val | Gly | Val |
| | | | 245 | | | | | 250 | | | | | 255 | | |
| Tyr | Met | Tyr | Leu | Asp | Ala | Gly | His | Ala | Gly | Trp | Leu | Gly | Trp | Pro | Ala |
| | | | 260 | | | | | 265 | | | | | 270 | | |
| Asn | Leu | Asn | Pro | Ala | Ala | Gln | Leu | Phe | Ser | Gln | Leu | Tyr | Arg | Asp | Ala |
| | | 275 | | | | | 280 | | | | | 285 | | | |
| Gly | Ser | Pro | Gln | Tyr | Val | Arg | Gly | Leu | Ala | Thr | Asn | Val | Ala | Asn | Tyr |
| | 290 | | | | | 295 | | | | | 300 | | | | |
| Asn | Ala | Leu | Ser | Ala | Ser | Ser | Pro | Asp | Pro | Val | Thr | Gln | Gly | Asn | Pro |
| 305 | | | | | 310 | | | | | 315 | | | | | 320 |
| Asn | Tyr | Asp | Glu | Leu | His | Tyr | Ile | Asn | Ala | Leu | Ala | Pro | Ala | Leu | Gln |
| | | | | 325 | | | | | 330 | | | | | 335 | |
| Ser | Gly | Gly | Phe | Pro | Ala | His | Phe | Ile | Val | Asp | Gln | Gly | Arg | Ser | Gly |
| | | | 340 | | | | | 345 | | | | | 350 | | |
| Val | Gln | Asn | Ile | Arg | Gln | Gln | Trp | Gly | Asp | Trp | Cys | Asn | Val | Lys | Gly |
| | | 355 | | | | | 360 | | | | | 365 | | | |
| Ala | Gly | Phe | Gly | Gln | Arg | Pro | Thr | Leu | Ser | Thr | Gly | Ser | Ser | Leu | Ile |
| | 370 | | | | | 375 | | | | | 380 | | | | |
| Asp | Ala | Ile | Val | Trp | Ile | Lys | Pro | Gly | Gly | Glu | Cys | Asp | Gly | Thr | Thr |

Asn Thr Ser Ser Pro Arg Tyr Asp Ser His Cys Gly Leu Ser Asp Ala
            405                 410                 415

Thr Pro Asn Ala Pro Glu Ala Gly Gln Trp Phe Gln Ala Tyr Phe Glu
            420                 425                 430

Thr Leu Val Arg Asn Ala Ser Pro Pro Leu
            435                 440

<210> SEQ ID NO 15
<211> LENGTH: 491
<212> TYPE: PRT
<213> ORGANISM: Piromyces sp.

<400> SEQUENCE: 15

Met Lys Ala Ser Ile Ala Leu Thr Ala Ile Ala Ala Leu Ala Ala Asn
1               5                   10                  15

Ala Ser Ala Ala Cys Phe Ser Glu Arg Leu Gly Tyr Pro Cys Cys Arg
            20                  25                  30

Gly Asn Glu Val Phe Tyr Thr Asp Asn Asp Gly Asp Trp Gly Val Glu
            35                  40                  45

Asn Gly Asn Trp Cys Gly Ile Gly Gly Ala Ser Ala Thr Thr Cys Trp
        50                  55                  60

Ser Gln Ala Leu Gly Tyr Pro Cys Cys Thr Ser Thr Ser Asp Val Ala
65              70                  75                  80

Tyr Val Asp Gly Asp Gly Asn Trp Gly Val Glu Asn Gly Asn Trp Cys
            85                  90                  95

Gly Ile Ile Ala Gly Gly Asn Ser Ser Asn Asn Ser Gly Ser Thr
            100                 105                 110

Ile Asn Val Gly Asp Val Thr Ile Gly Asn Gln Tyr Thr His Thr Gly
            115                 120                 125

Asn Pro Phe Ala Gly His Lys Phe Phe Ile Asn Pro Tyr Tyr Thr Ala
        130                 135                 140

Glu Val Asp Gly Ala Ile Ala Gln Ile Ser Asn Ala Ser Leu Arg Ala
145             150                 155                 160

Lys Ala Glu Lys Met Lys Glu Phe Ser Asn Ala Ile Trp Leu Asp Thr
            165                 170                 175

Ile Lys Asn Met Asn Glu Trp Leu Glu Lys Asn Leu Lys Tyr Ala Leu
            180                 185                 190

Ala Glu Gln Asn Glu Thr Gly Lys Thr Val Leu Thr Val Phe Val Val
            195                 200                 205

Tyr Asp Leu Pro Gly Arg Asp Cys His Ala Leu Ala Ser Asn Gly Glu
        210                 215                 220

Leu Leu Ala Asn Asp Ser Asp Trp Ala Arg Tyr Gln Ser Glu Tyr Ile
225             230                 235                 240

Asp Val Ile Glu Glu Lys Leu Lys Thr Tyr Lys Ser Gln Pro Val Val
            245                 250                 255

Leu Val Val Glu Pro Asp Ser Leu Ala Asn Met Val Thr Asn Leu Asp
            260                 265                 270

Ser Thr Pro Ala Cys Arg Asp Ser Glu Lys Tyr Tyr Met Asp Gly His
        275                 280                 285

Ala Tyr Leu Ile Lys Lys Leu Gly Val Leu Pro His Val Ala Met Tyr
            290                 295                 300

Leu Asp Ile Gly His Ala Phe Trp Leu Gly Trp Asp Asp Asn Arg Leu
305             310                 315                 320

```
Lys Ala Gly Lys Val Tyr Ser Lys Val Ile Gln Ser Gly Ala Pro Gly
                325                 330                 335

Asn Val Arg Gly Phe Ala Ser Asn Val Ala Asn Tyr Thr Pro Trp Glu
            340                 345                 350

Asp Pro Thr Leu Ser Arg Gly Pro Asp Thr Glu Trp Asn Pro Cys Pro
        355                 360                 365

Asp Glu Lys Arg Tyr Ile Glu Ala Met Tyr Lys Asp Phe Lys Ser Ala
    370                 375                 380

Gly Ile Lys Ser Val Tyr Phe Ile Asp Asp Thr Ser Arg Asn Gly His
385                 390                 395                 400

Lys Thr Asp Arg Thr His Pro Gly Glu Trp Cys Asn Gln Thr Gly Val
                405                 410                 415

Gly Ile Gly Ala Arg Pro Gln Ala Asn Pro Ile Ser Gly Met Asp Tyr
            420                 425                 430

Leu Asp Ala Phe Tyr Trp Val Lys Pro Leu Gly Glu Ser Asp Gly Tyr
        435                 440                 445

Ser Asp Thr Thr Ala Val Arg Tyr Asp Gly Tyr Cys Gly His Ala Thr
    450                 455                 460

Ala Met Lys Pro Ala Pro Glu Ala Gly Gln Trp Phe Gln Lys His Phe
465                 470                 475                 480

Glu Gln Gly Leu Glu Asn Ala Asn Pro Pro Leu
                485                 490

<210> SEQ ID NO 16
<211> LENGTH: 19
<212> TYPE: PRT
<213> ORGANISM: Artificial Sequence
<220> FEATURE:
<223> OTHER INFORMATION: S. cerevisiae alpha mating factor signal
      sequence

<400> SEQUENCE: 16

Met Arg Phe Pro Ser Ile Phe Thr Ala Val Leu Phe Ala Ala Ser Ser
1               5                   10                  15

Ala Leu Ala

<210> SEQ ID NO 17
<211> LENGTH: 42
<212> TYPE: PRT
<213> ORGANISM: Artificial Sequence
<220> FEATURE:
<223> OTHER INFORMATION: optimized linker 1

<400> SEQUENCE: 17

Gly Gly Gly Gly Ser Gly Gly Gly Gly Ser Ala Trp His Pro Gln Phe
1               5                   10                  15

Gly Gly Glu Asn Leu Tyr Phe Gln Gly Asp Tyr Lys Asp Asp Asp Lys
            20                  25                  30

Gly Gly Gly Gly Ser Gly Gly Gly Gly Ser
        35                  40

<210> SEQ ID NO 18
<211> LENGTH: 144
<212> TYPE: DNA
<213> ORGANISM: Artificial Sequence
<220> FEATURE:
<223> OTHER INFORMATION: optimized linker 1

<400> SEQUENCE: 18
ggaggaggtg gttcaggagg tggtgggtct gcttggcatc cacaatttgg aggaggcggt     60
```

```
ggtgaaaatc tgtatttcca gggaggcgga ggtgattaca aggatgacga caaaggaggt    120
ggtggatcag gaggtggtgg ctcc                                           144
```

<210> SEQ ID NO 19
<211> LENGTH: 37
<212> TYPE: PRT
<213> ORGANISM: Artificial Sequence
<220> FEATURE:
<223> OTHER INFORMATION: optimized linker 2

<400> SEQUENCE: 19

```
Gly Gly Gly Gly Ser Gly Gly Gly Gly Ser Trp Ser His Pro Gln Phe
1               5                   10                  15

Glu Lys Gly Gly Glu Asn Leu Tyr Phe Gln Gly Gly Gly Gly Ser
            20                  25                  30

Gly Gly Gly Gly Ser
        35
```

<210> SEQ ID NO 20
<211> LENGTH: 117
<212> TYPE: DNA
<213> ORGANISM: Artificial Sequence
<220> FEATURE:
<223> OTHER INFORMATION: optimized linker 2

<400> SEQUENCE: 20

```
ggtggcggtg gatctggagg aggcggttct ggtctcacc cacaatttga aagggtgga      60 gaaaacttgt actttcaagg cggtggtgga ggttctggcg aggtggctc cggctca       117
```

<210> SEQ ID NO 21
<211> LENGTH: 8452
<212> TYPE: DNA
<213> ORGANISM: Artificial Sequence
<220> FEATURE:
<223> OTHER INFORMATION: pMU784

<400> SEQUENCE: 21

```
agctgtttcc tgtgtgaaat tgttatccgc tcacaattcc acacaacata cgagccggaa    60
gcataaagtg taaagcctgg ggtgcctaat gagtgaggta actcacatta attgcgttgc   120
gctcactgcc cgctttccag tcgggaaacc tgtcgtgcca gctggattaa tgaatcggcc   180
aacgcgcggg gagaggcggt ttgcgtattg ggcgctcttc cgcttcctcg ctcactgact   240
cgctgcgctc ggtcgttcgg ctgcggcgag cggtatcagc tcactcaaag gcggtaatac   300
ggttatccac agaatcaggg gataacgcag gaaagaacat gtgagcaaaa ggccagcaaa   360
aggccaggaa ccgtaaaaag gccgcgttgc tggcgttttt ccataggctc cgcccccctg   420
acgagcatca caaaaatcga cgctcaagtc agaggtggcg aaacccgaca ggactataaa   480
gataccaggc gtttccccct ggaagctccc tcgtgcgctc tcctgttccg accctgccgc   540
ttaccggata cctgtccgcc tttctccctt cgggaagcgt ggcgctttct caatgctcac   600
gctgtaggta tctcagttcg gtgtaggtcg ttcgctccaa gctgggctgt gtgcacgaac   660
cccccgttca gcccgaccgc tgcgccttat ccggtaacta tcgtcttgag tccaacccgg   720
taagacacga cttatcgcca ctggcagcag ccactggtaa caggattagc agagcgaggt   780
atgtaggcgg tgctacagag ttcttgaagt ggtggcctaa ctacggctac actagaagga   840
cagtatttgg tatctgcgct ctgctgaagc cagttacctt cggaaaaaga gttggtagct   900
cttgatccgg caaacaaacc accgctggta gcggtggttt ttttgtttgc aagcagcaga   960
```

```
ttacgcgcag aaaaaaagga tctcaagaag atcctttgat cttttctacg gggtctgacg   1020
ctcagtggaa cgaaaactca cgttaaggga ttttggtcat gagattatca aaaggatct    1080 tcacctagat cctttaaat taaaaatgaa gttttaaatc aatctaaagt atatatgagt    1140
aaacttggtc tgacagttac caatgcttaa tcagtgaggc acctatctca gcgatctgtc   1200
tatttcgttc atccatagtt gcctgactcc ccgtcgtgta gataactacg atacgggagg   1260
gcttaccatc tggccccagt gctgcaatga taccgcgaga cccacgctca ccggctccag   1320
atttatcagc aataaaccag ccagccggaa gggccgagcg cagaagtggt cctgcaactt   1380
tatccgcctc catccagtct attaattgtt gccgggaagc tagagtaagt agttcgccag   1440
ttaatagttt gcgcaacgtt gttgccattg ctacaggcat cgtggtgtca cgctcgtcgt   1500
ttggtatggc ttcattcagc tccggttccc aacgatcaag gcgagttaca tgatccccca   1560
tgttgtgcaa aaaagcggtt agctccttcg gtcctccgat cgttgtcaga agtaagttgg   1620
ccgcagtgtt atcactcatg gttatggcag cactgcataa ttctcttact gtcatgccat   1680
ccgtaagatg cttttctgtg actggtgagt actcaaccaa gtcattctga aatagtgta    1740 tgcggcgacc gagttgctct tgcccggcgt caatacggga taataccgcg ccacatagca   1800
gaactttaaa agtgctcatc attggaaaac gttcttcggg gcgaaaactc tcaaggatct   1860
taccgctgtt gagatccagt tcgatgtaac ccactcgtgc acccaactga tcttcagcat   1920
cttttacttt caccagcgtt tctgggtgag caaaaacagg aaggcaaaat gccgcaaaaa   1980
agggaataag ggcgacacgg aaatgttgaa tactcatact cttcctttt caatattatt     2040 gaagcattta tcagggttat tgtctcatga gcggatacat atttgaatgt atttagaaaa   2100
ataaacaaat aggggttccg cgcacatttc cccgaaaagt gccacctgac gtctaagaaa   2160
ccattattat catgacatta acctataaaa ataggcgtat cacgaggccc tttcgtctcg   2220
cgcgtttcgg tgatgacggt gaaaacctct gacacatgca gctcccggag acggtcacag   2280
cttgtctgta agcggatgcc gggagcagac aagcccgtca gggcgcgtca gcgggtgttg   2340
gcgggtgtcg ggctggctt aactatgcgg catcagagca gattgtactg agagtgcacc    2400
ataacgcatt taagcataaa cacgcactat gccgttcttc tcatgtatat atatatacag   2460
gcaacacgca gatataggtg cgacgtgaac agtgagctgt atgtgcgcag ctcgcgttgc   2520
attttcggaa gcgctcgttt tcggaaacgc tttgaagttc ctattccgaa gttcctattc   2580
tctagctaga aagtatagga acttcagagc gcttttgaaa accaaaagcg ctctgaagac   2640
gcactttcaa aaaccaaaa acgcaccgga ctgtaacgag ctactaaaat attgcgaata    2700
ccgcttccac aaacattgct caaaagtatc tctttgctat atatctctgt gctatatccc   2760
tatataacct acccatccac ctttcgctcc ttgaacttgc atctaaactc gacctctaca   2820
ttttttatgt ttatctctag tattactctt tagacaaaaa aattgtagta agaactattc   2880
atagagtgaa tcgaaaacaa tacgaaaatg taaacatttc ctatacgtag tatatagaga   2940
caaaatagaa gaaaccgttc ataattttct gaccaatgaa gaatcatcaa cgctatcact   3000
ttctgttcac aaagtatgcg caatccacat cggtatagaa tataatcggg gatgcctta    3060 tcttgaaaaa atgcacccgc agcttcgcta gtaatcagta aacgcgggaa gtggagtcag   3120
gcttttttta tggaagagaa aatagacacc aaagtagcct tcttctaacc ttaacggacc   3180
tacagtgcaa aaagttatca agagactgca ttatagagcg cacaaaggag aaaaaaagta   3240
atctaagatg ctttgttaga aaaatagcgc tctcgggatg cattttttgta gaacaaaaaa   3300
```

```
gaagtataga ttctttgttg gtaaaatagc gctctcgcgt tgcatttctg ttctgtaaaa    3360
atgcagctca gattctttgt ttgaaaaatt agcgctctcg cgttgcattt ttgttttaca    3420
aaaatgaagc acagattctt cgttggtaaa atagcgcttt cgcgttgcat ttctgttctg    3480
taaaaatgca gctcagattc tttgtttgaa aaattagcgc tctcgcgttg cattttttgtt   3540
ctacaaaatg aagcacagat gcttcgttaa caaagatatg ctattgaagt gcaagatgga    3600
aacgcagaaa atgaaccggg gatgcgacgt gcaagattac ctatgcaata gatgcaatag    3660
tttctccagg aaccgaaata catacattgt cttccgtaaa gcgctagact atatattatt    3720
atacaggttc aaatatacta tctgtttcag ggaaaactcc caggttcgga tgttcaaaat    3780
tcaatgatgg gtaacaagag ctttttcaatt catcattttt tttttattct tttttttgat    3840
ttcggtttct ttgaaatttt tttgattcgg taatctccga acagaaggaa gaacgaagga    3900
aggagcacag acttagattg gtatatatac gcatatgtag tgttgaagaa acatgaaatt    3960
gcccagtatt cttaacccaa ctgcacagaa caaaaaccga aacgaagata aatcatgtcg    4020
aaagctacat ataaggaacg tgctgctact catcctagtc ctgttgctgc caagctattt    4080
aatatcatgc acgaaaagca aacaaacttg tgtgcttcat tggatgttcg taccaccaag    4140
gaattactgg agttagttga agcattaggt cccaaaattt gtttactaaa acacatgtg     4200
gatatcttga ctgattttc catggagggc acagttaagc cgctaaaggc attatccgcc    4260
aagtacaatt ttttactctt cgaagacaga aaatttgctg acattggtaa tacagtcaaa    4320
ttgcagtact ctgcgggtgt atacagaata gcagaatggg cagacattac gaatgcacac    4380
ggtgtggtgg gcccaggtat tgttagcggt ttgaagcagg cggcagaaga agtaacaaag    4440
gaacctagag gccttttgat gttagcagaa ttgtcatgca agggctccct atctactgga    4500
gaatatacta agggtactgt tgacattgcg aagagcgaca aagattttgt tatcggcttt    4560
attgctcaaa gagacatggg tggaagagat gaaggttacg attggttgat tatgacaccc    4620
ggtgtggggtt tagatgacaa gggagacgca ttgggtcaac agtatagaac cgtggatgat    4680
gtggtctcta caggatctga cattattatt gttggaagag gactatttgc aaagggaagg    4740
gatgctaagg tagagggtga acgttacaga aaagcaggct gggaagcata tttgagaaga    4800
tgcggccagc aaaactaaaa aactgtatta taagtaaatg catgtatact aaactcacaa    4860
attagagctt caatttaatt atatcagtta ttaccctatg cggtgtgaaa taccgcacag    4920
atgcgtaagg agaaaatacc gcatcaggcg ccattcgcca ttcaggctgc gcaactgttg    4980
ggaagggcga tcggtgcggg cctcttcgct attacgccag ctggcgaagg ggggatgtgc    5040
tgcaaggcga ttaagttggg taacgccagg gttttcccag tcacgacgtt gtaaaacgac    5100
ggccagtgcc aagctttcta actgatctat ccaaaactga aaattacatt cttgattagg    5160
tttatcacag gcaaatgtaa tttgtggtat tttgccgttc aaaatctgta gaattttctc    5220
attggtcaca ttcaacctg aaaatacttt atctacaatc ataccattct tataacatgt     5280
ccccttaata ctaggatcag gcatgaacgc atcacagaca aaatcttctt gacaaacgtc    5340
acaattgatc cctccccatc cgttatcaca atgacaggtg tcattttgtg ctcttatggg    5400
acgatcctta ttaccgcttt catccggtga tagaccgcca cagaggggca gagagcaatc    5460
atcacctgca aaccctttcta tacactcaca tctaccagtg tacgaattgc attcagaaaa   5520
ctgtttgcat tcaaaaatag gtagcataca attaaaacat ggcgggcacg tatcattgcc    5580
cttatccttgt gcagttagac gcgaattttt cgaagaagta ccttcaaaga atggggtctc    5640
atcttgtttt gcaagtacca ctgagcagga taataataga aatgataata tactatagta    5700
```

```
gagataacgt cgatgacttc ccatactgta attgctttta gttgtgtatt tttagtgtgc    5760
aagtttctgt aaatcgatta atttttttt ctttcctctt tttattaacc ttaattttta    5820
ttttagattc ctgacttcaa ctcaagacgc acagatatta taacatctgc acaataggca    5880
tttgcaagaa ttactcgtga gtaaggaaag agtgaggaac tatcgcatac ctgcatttaa    5940
agatgccgat ttgggcgcga atcctttatt ttggcttcac cctcatacta ttatcagggc    6000
cagaaaaagg aagtgtttcc ctccttcttg aattgatgtt accctcataa agcacgtggc    6060
ctcttatcga gaaagaaatt accgtcgctc gtgatttgtt tgcaaaaaga acaaaactga    6120
aaaaacccag acacgctcga cttcctgtct tcctattgat tgcagcttcc aatttcgtca    6180
cacaacaagg tcctagcgac ggctcacagg ttttgtaaca agcaatcgaa ggttctggaa    6240
tggcgggaaa gggtttagta ccacatgcta tgatgcccac tgtgatctcc agagcaaagt    6300
tcgttcgatc gtactgttac tctctctctt tcaaacagaa ttgtccgaat cgtgtgacaa    6360
caacagcctt ttctcacaca ctcttttctt ctaaccaagg gggtggttta gtttagtaga    6420
acctcgtgaa acttacattt acatatatat aaacttgcat aaattggtca atgcaagaaa    6480
tacatatttg gtcttttcta attcgtagtt tttcaagttc ttagatgctt tctttttctc    6540
tttttttacag atcatcaagg aagtaattat ctactttta caacaaatat aaaacttaat    6600
taaacaatgg ccaagaagtt gttcattacc gctgccttag ctgccgcagt gcttgctgca    6660
ccagtgatcg aagagagaca aaattgcgga gccgtctgga cacagtgcgg aggcaacggc    6720
tggcaaggcc caacatgttg tgcttctggc tcaacgtgcg tggcacagaa cgagtggtat    6780
tcccagtgcc ttccaaactc ccaggtgact tcttcaacaa cccccagctc aacgtctact    6840
tcacagagat ccacaagtac ctcttctagc acaaccagaa gtggctcatc ctcatctagc    6900
agtacgaccc ctccacccgt atcaagtcct gtcacgagta tccctggcgg agcaacctca    6960
acagccagtt attccggcaa tccttttctct ggagtgagat tatttgcaaa cgactattat    7020
agatcagagg ttcacaacct tgcaattcct tctatgacgg gaaccctagc cgcaaaggct    7080
tccgccgtag cagaagtccc tagtttccaa tggcttgaca gaaacgttac aatagataca    7140
cttatggtac agactttatc tcaggttaga gctttgaata aggccggtgc caacccacct    7200
tatgctgccc aattagtagt ctatgacttg ccagatagag actgtgctgc cgcagcttct    7260
aatggtgaat tttccatcgc aaatggcgga gctgcaaact atagatcata cattgatgca    7320
ataagaaaac acatcattga gtattctgat attagaataa tccttgtgat tgaaccagac    7380
tccatggcta atatggttac caacatgaat gtagccaagt gttctaacgc agcttccaca    7440
taccatgagc taaccgtata tgcattaaaa caactgaatc tacctaacgt tgctatgtac    7500
ttagatgccg gtcatgccgg atggttgggc tggcctgcaa atatccaacc cgcagctgaa    7560
ttgttcgctg gaatctacaa cgacgccgga aagcccgctg ccgttagagg cttagccaca    7620
aatgttgcaa attacaacgc ttggtcaatt gctagtgccc cttcttatac ctcaccaaat    7680
cctaactacg atgagaaaca ttacatagaa gcatttttcc cattgttaaa ctccgctgga    7740
ttccctgcca gattcatcgt ggataccggt agaaacggca acaaccaac tggacaacaa    7800
caatggggag attggtgtaa cgtcaaggga accggcttcg cgtcaggcc tacggcaaac    7860
accggacacg agctagtcga cgcttttgta tgggttaagc caggtggcga aagtgacgga    7920
acaagtgaca cgagtgctgc aagatacgat taccactgtg gtctgtccga cgctttacag    7980
cccgccccg aggctggaca atggttccag gcttattttg aacaattgtt aacgaacgca    8040
```

-continued

```
aatccaccat tctaaggcgc gccgaattcg agagactcga gactgaatcg gatcgatccc    8100
gggcccgtcg agggatctgc gatagatcaa ttttttcttt ttctctttcc ccatcccttta   8160 cgctaaaata atagtttatt ttattttttg aatatttttt atttatatac gtatatatag    8220
actattattt atcttttaat gattattaag atttttatta aaaaaaaatt cgctcctctt    8280
ttaatgcctt tatgcagttt tttttccca ttcgatattt ctatgttcgg gttcagcgta    8340
ttttaagttt aataactcga aaattctgcg ttcgttaaag cttgcatgcc tgcaggtcga    8400
ctctagagga tccccgggta ccgagctcga attaattcgt aatcatggtc at            8452
```

<210> SEQ ID NO 22
<211> LENGTH: 313
<212> TYPE: PRT
<213> ORGANISM: Artificial Sequence
<220> FEATURE:
<223> OTHER INFORMATION: Cochliobolus heterostrophus C4 cel7, GH Family 6 Domain (aa 42-354)

<400> SEQUENCE: 22

```
Ala Asn Pro Tyr Tyr Ser Ser Glu Val His Thr Leu Ala Met Pro Ser
1               5                   10                  15

Leu Pro Ala Ser Leu Lys Pro Ala Ala Thr Ala Val Ala Lys Val Gly
            20                  25                  30

Ser Phe Val Trp Met Asp Thr Met Ala Lys Val Pro Leu Met Asp Thr
        35                  40                  45

Tyr Leu Ala Asp Ile Lys Ala Lys Asn Ala Ala Gly Ala Asn Leu Met
    50                  55                  60

Gly Thr Phe Val Val Tyr Asp Leu Pro Asp Arg Asp Cys Ala Ala Leu
65                  70                  75                  80

Ala Ser Asn Gly Glu Leu Lys Ile Asp Glu Gly Gly Val Glu Lys Tyr
                85                  90                  95

Lys Thr Gln Tyr Ile Asp Lys Ile Ala Ala Ile Ile Lys Lys Tyr Pro
            100                 105                 110

Asp Val Lys Ile Asn Leu Ala Ile Glu Pro Asp Ser Leu Ala Asn Met
        115                 120                 125

Val Thr Asn Met Gly Val Gln Lys Cys Ser Arg Ala Ala Pro Tyr Tyr
    130                 135                 140

Lys Glu Leu Thr Ala Tyr Ala Leu Lys Thr Leu Asn Phe Asn Asn Val
145                 150                 155                 160

Asp Met Tyr Met Asp Gly Gly His Ala Gly Trp Leu Gly Trp Asp Ala
                165                 170                 175

Asn Ile Gly Pro Thr Ala Lys Leu Phe Ala Glu Val Tyr Lys Ala Ala
            180                 185                 190

Gly Ser Pro Arg Gly Val Arg Gly Ile Val Thr Asn Val Ser Asn Tyr
        195                 200                 205

Asn Ala Leu Arg Val Ser Ser Cys Pro Ser Ile Thr Gln Gly Asn Lys
    210                 215                 220

Asn Cys Asp Glu Glu Arg Tyr Ile Asn Ala Leu Ala Pro Leu Leu Lys
225                 230                 235                 240

Asn Glu Gly Phe Pro Ala His Phe Ile Val Asp Gln Gly Arg Ser Gly
                245                 250                 255

Lys Val Pro Thr Asn Gln Gln Glu Trp Gly Asp Trp Cys Asn Val Ser
            260                 265                 270

Gly Ala Gly Phe Gly Thr Arg Pro Thr Thr Asn Thr Gly Asn Ala Leu
        275                 280                 285
```

```
Ile Asp Ala Ile Val Trp Val Lys Pro Gly Gly Glu Ser Asp Gly Thr
290                 295                 300

Ser Asp Thr Ser Ala Ala Arg Tyr Asp
305                 310
```

<210> SEQ ID NO 23
<211> LENGTH: 18
<212> TYPE: PRT
<213> ORGANISM: Artificial Sequence
<220> FEATURE:
<223> OTHER INFORMATION: Cochliobolus heterostrophus C4 cel7, Signal
      Peptide (aa 1-18)

<400> SEQUENCE: 23

```
Met Leu Ser Asn Val Phe Leu Thr Ala Ala Leu Ala Ala Gly Leu Ala
1               5                   10                  15

Gln Ala
```

<210> SEQ ID NO 24
<211> LENGTH: 313
<212> TYPE: PRT
<213> ORGANISM: Artificial Sequence
<220> FEATURE:
<223> OTHER INFORMATION: Gibberella zeae K59 cel6, GH Family 6 Domain
      (aa 111-423)

<400> SEQUENCE: 24

```
Ala Asn Asn Tyr Tyr Arg Ser Glu Val Ser Thr Leu Ala Ile Pro Lys
1               5                   10                  15

Leu Ser Gly Ala Met Ala Thr Ala Ala Lys Val Ala Asp Val Pro
            20                  25                  30

Ser Phe Gln Trp Met Asp Thr Tyr Asp His Ile Ser Phe Met Glu Asp
        35                  40                  45

Ser Leu Ala Asp Ile Arg Lys Ala Asn Lys Ala Gly Gly Asn Tyr Ala
    50                  55                  60

Gly Gln Phe Val Val Tyr Asp Leu Pro Asp Arg Asp Cys Ala Ala Ala
65                  70                  75                  80

Ala Ser Asn Gly Glu Tyr Ser Leu Asp Lys Asp Gly Lys Asn Lys Tyr
                85                  90                  95

Lys Ala Tyr Ile Ala Asp Gln Gly Ile Leu Gln Asp Tyr Ser Asp Thr
            100                 105                 110

Arg Ile Ile Leu Val Ile Glu Pro Asp Ser Leu Ala Asn Met Val Thr
        115                 120                 125

Asn Met Asn Val Pro Lys Cys Ala Asn Ala Ala Ser Ala Tyr Lys Glu
    130                 135                 140

Leu Thr Ile His Ala Leu Lys Glu Leu Asn Leu Pro Asn Val Ser Met
145                 150                 155                 160

Tyr Ile Asp Ala Gly His Gly Gly Trp Leu Gly Trp Pro Ala Asn Leu
                165                 170                 175

Pro Pro Ala Ala Gln Leu Tyr Gly Gln Leu Tyr Lys Ala Gly Lys
            180                 185                 190

Pro Ser Arg Leu Arg Gly Leu Val Thr Asn Val Ser Asn Tyr Asn Ala
        195                 200                 205

Trp Lys Leu Ser Ser Lys Pro Asp Tyr Thr Glu Ser Asn Pro Asn Tyr
    210                 215                 220

Asp Glu Gln Lys Tyr Ile His Ala Leu Ser Pro Leu Leu Glu Gln Glu
225                 230                 235                 240

Gly Trp Pro Gly Ala Lys Phe Ile Val Asp Gln Gly Arg Ser Gly Lys
```

```
                    245                 250                 255
Gln Pro Thr Gly Gln Lys Ala Trp Gly Asp Trp Cys Asn Ala Pro Gly
                260                 265                 270

Thr Gly Phe Gly Leu Arg Pro Ser Ala Asn Thr Gly Asp Ala Leu Val
            275                 280                 285

Asp Ala Phe Val Trp Val Lys Pro Gly Gly Glu Ser Asp Gly Thr Ser
290                 295                 300

Asp Thr Ser Ala Ala Arg Tyr Asp Tyr
305                 310

<210> SEQ ID NO 25
<211> LENGTH: 18
<212> TYPE: PRT
<213> ORGANISM: Artificial Sequence
<220> FEATURE:
<223> OTHER INFORMATION: Gibberella zeae K59 cel6, Signal Peptide
      (aa 1-18)

<400> SEQUENCE: 25

Met Thr Ala Tyr Lys Leu Phe Leu Ala Ala Phe Ala Ala Thr Ala
1               5                   10                  15

Leu Ala

<210> SEQ ID NO 26
<211> LENGTH: 29
<212> TYPE: PRT
<213> ORGANISM: Artificial Sequence
<220> FEATURE:
<223> OTHER INFORMATION: Gibberella zeae K59 cel6, CBM Domain (aa 31-59)

<400> SEQUENCE: 26

Val Trp Ser Gln Cys Gly Gly Gln Asn Trp Ser Gly Thr Pro Cys Cys
1               5                   10                  15

Thr Ser Gly Asn Lys Cys Val Lys Val Asn Asp Phe Tyr
            20                  25

<210> SEQ ID NO 27
<211> LENGTH: 313
<212> TYPE: PRT
<213> ORGANISM: Artificial Sequence
<220> FEATURE:
<223> OTHER INFORMATION: Irpex lacteus MC-2 cex3, GH Family 6 Domain
      (aa 107-419)

<400> SEQUENCE: 27

Val Asp Leu Trp Ala Asn Asn Tyr Tyr Arg Ser Glu Val Ser Thr Leu
1               5                   10                  15

Ala Ile Pro Lys Leu Ser Gly Ala Met Ala Thr Ala Ala Lys Val
            20                  25                  30

Ala Asp Val Pro Ser Phe Gln Trp Met Asp Thr Tyr Asp His Ile Ser
        35                  40                  45

Phe Met Glu Asp Ser Leu Ala Asp Ile Arg Lys Ala Asn Lys Ala Gly
    50                  55                  60

Gly Asn Tyr Ala Gly Gln Phe Val Val Tyr Asp Leu Pro Asp Arg Asp
65                  70                  75                  80

Cys Ala Ala Ala Ala Ser Asn Gly Glu Tyr Ser Leu Asp Lys Asp Gly
                85                  90                  95

Lys Asn Lys Tyr Lys Ala Tyr Ile Ala Asp Gln Gly Ile Leu Gln Asp
            100                 105                 110

Tyr Ser Asp Thr Arg Ile Ile Leu Val Ile Glu Pro Asp Ser Leu Ala
```

```
                     115                 120                 125
Asn Met Val Thr Asn Met Asn Val Pro Lys Cys Ala Asn Ala Ala Ser
        130                 135                 140

Ala Tyr Lys Glu Leu Thr Ile His Ala Leu Lys Glu Leu Asn Leu Pro
145                 150                 155                 160

Asn Val Ser Met Tyr Ile Asp Ala Gly His Gly Gly Trp Leu Gly Trp
                165                 170                 175

Pro Ala Asn Leu Pro Pro Ala Ala Gln Leu Tyr Gly Gln Leu Tyr Lys
            180                 185                 190

Asp Ala Gly Lys Pro Ser Arg Leu Arg Gly Leu Val Thr Asn Val Ser
        195                 200                 205

Asn Tyr Asn Ala Trp Lys Leu Ser Ser Lys Pro Asp Tyr Thr Glu Ser
    210                 215                 220

Asn Pro Asn Tyr Asp Glu Gln Lys Tyr Ile His Ala Leu Ser Pro Leu
225                 230                 235                 240

Leu Glu Gln Glu Gly Trp Pro Gly Ala Lys Phe Ile Val Asp Gln Gly
                245                 250                 255

Arg Ser Gly Lys Gln Pro Thr Gly Gln Lys Ala Trp Gly Asp Trp Cys
            260                 265                 270

Asn Ala Pro Gly Thr Gly Phe Gly Leu Arg Pro Ser Ala Asn Thr Gly
        275                 280                 285

Asp Ala Leu Val Asp Ala Phe Val Trp Val Lys Pro Gly Gly Glu Ser
    290                 295                 300

Asp Gly Thr Ser Asp Thr Ser Ala Ala
305                 310

<210> SEQ ID NO 28
<211> LENGTH: 20
<212> TYPE: PRT
<213> ORGANISM: Artificial Sequence
<220> FEATURE:
<223> OTHER INFORMATION: Irpex lacteus MC-2 cex3, Signal Peptide Domain
      (aa 1-20)

<400> SEQUENCE: 28

Met Thr Ala Tyr Lys Leu Phe Leu Ala Ala Ala Phe Ala Ala Thr Ala
1               5                   10                  15

Leu Ala Ala Pro
            20

<210> SEQ ID NO 29
<211> LENGTH: 28
<212> TYPE: PRT
<213> ORGANISM: Artificial Sequence
<220> FEATURE:
<223> OTHER INFORMATION: Irpex lacteus MC-2 cex3, CBM Domain (aa 25-52)

<400> SEQUENCE: 29

Gln Ser Cys Ser Asn Gly Val Trp Ser Gln Cys Gly Gly Gln Asn Trp
1               5                   10                  15

Ser Gly Thr Pro Cys Cys Thr Ser Gly Asn Lys Cys
            20                  25

<210> SEQ ID NO 30
<211> LENGTH: 290
<212> TYPE: PRT
<213> ORGANISM: Artificial Sequence
<220> FEATURE:
<223> OTHER INFORMATION: Volvariella volvacea cbhII-I, GH Family 6
      Domain (aa 120-409)
```

<400> SEQUENCE: 30

```
Lys Ala Leu Lys Val Ala Gln Ile Pro Thr Phe Thr Trp Phe Asp Val
1               5                   10                  15

Ile Ala Lys Thr Ser Thr Leu Gly Asp Tyr Leu Ala Glu Ala Ser Ala
            20                  25                  30

Leu Gly Lys Ser Ser Gly Lys Lys Tyr Leu Val Gln Ile Val Val Tyr
        35                  40                  45

Asp Leu Pro Asp Arg Asp Cys Ala Ala Leu Ala Ser Asn Gly Glu Phe
    50                  55                  60

Ser Ile Ala Asn Asn Gly Leu Asn Asn Tyr Lys Gly Tyr Ile Asp Gln
65                  70                  75                  80

Leu Val Ala Gln Ile Lys Lys Tyr Pro Asp Val Arg Val Val Ala Val
                85                  90                  95

Ile Glu Pro Asp Ser Leu Ala Asn Leu Val Thr Asn Leu Asn Val Ser
            100                 105                 110

Lys Cys Ala Asn Ala Gln Thr Ala Tyr Lys Ala Gly Val Thr Tyr Ala
        115                 120                 125

Leu Gln Gln Leu Asn Ser Val Gly Val Tyr Met Tyr Leu Asp Ala Gly
    130                 135                 140

His Ala Gly Trp Leu Gly Trp Pro Ala Asn Leu Asn Pro Ala Ala Gln
145                 150                 155                 160

Leu Phe Ser Gln Leu Tyr Arg Asp Ala Gly Ser Pro Gln Tyr Val Arg
                165                 170                 175

Gly Leu Ala Thr Asn Val Ala Asn Tyr Asn Ala Leu Ser Ala Ser Ser
            180                 185                 190

Pro Asp Pro Val Thr Gln Gly Asn Pro Asn Tyr Asp Glu Leu His Tyr
        195                 200                 205

Ile Asn Ala Leu Ala Pro Ala Leu Gln Ser Gly Gly Phe Pro Ala His
    210                 215                 220

Phe Ile Val Asp Gln Gly Arg Ser Gly Val Gln Asn Ile Arg Gln Gln
225                 230                 235                 240

Trp Gly Asp Trp Cys Asn Val Lys Gly Ala Gly Phe Gly Gln Arg Pro
                245                 250                 255

Thr Leu Ser Thr Gly Ser Ser Leu Ile Asp Ala Ile Val Trp Ile Lys
            260                 265                 270

Pro Gly Gly Glu Cys Asp Gly Thr Thr Asn Thr Ser Ser Pro Arg Tyr
        275                 280                 285

Asp Ser
    290
```

<210> SEQ ID NO 31
<211> LENGTH: 20
<212> TYPE: PRT
<213> ORGANISM: Artificial Sequence
<220> FEATURE:
<223> OTHER INFORMATION: Volvariella volvacea cbhII-I, Signal Peptide
      Domain (aa 1-20)

<400> SEQUENCE: 31

```
Met Ser Arg Phe Ser Ala Leu Thr Ala Leu Leu Leu Ser Leu Pro Leu
1               5                   10                  15

Leu Ala Ile Ala
            20
```

<210> SEQ ID NO 32

```
<211> LENGTH: 28
<212> TYPE: PRT
<213> ORGANISM: Artificial Sequence
<220> FEATURE:
<223> OTHER INFORMATION: Volvariella volvacea cbhII-I, CBM Domain
      (aa 25-52)

<400> SEQUENCE: 32
```

Tyr Gly Gln Cys Gly Gly Asn Gly Trp Thr Gly Pro Lys Thr Cys Val
1               5                   10                  15

Ser Gly Ala Thr Cys Thr Val Ile Asn Asp Trp Tyr
            20                  25

```
<210> SEQ ID NO 33
<211> LENGTH: 320
<212> TYPE: PRT
<213> ORGANISM: Artificial Sequence
<220> FEATURE:
<223> OTHER INFORMATION: Piromyces sp. E2 cel6A, GH Family 6 Domain
      (aa 138-457)

<400> SEQUENCE: 33
```

Ile Asn Pro Tyr Tyr Thr Ala Glu Val Asp Gly Ala Ile Ala Gln Ile
1               5                   10                  15

Ser Asn Ala Ser Leu Arg Ala Lys Ala Glu Lys Met Lys Glu Phe Ser
            20                  25                  30

Asn Ala Ile Trp Leu Asp Thr Ile Lys Asn Met Asn Glu Trp Leu Glu
        35                  40                  45

Lys Asn Leu Lys Tyr Ala Leu Ala Glu Gln Asn Glu Thr Gly Lys Thr
    50                  55                  60

Val Leu Thr Val Phe Val Val Tyr Asp Leu Pro Gly Arg Asp Cys His
65                  70                  75                  80

Ala Leu Ala Ser Asn Gly Glu Leu Leu Ala Asn Asp Ser Asp Trp Ala
                85                  90                  95

Arg Tyr Gln Ser Glu Tyr Ile Asp Val Ile Glu Glu Lys Leu Lys Thr
            100                 105                 110

Tyr Lys Ser Gln Pro Val Val Leu Val Val Glu Pro Asp Ser Leu Ala
        115                 120                 125

Asn Met Val Thr Asn Leu Asp Ser Thr Pro Ala Cys Arg Asp Ser Glu
    130                 135                 140

Lys Tyr Tyr Met Asp Gly His Ala Tyr Leu Ile Lys Lys Leu Gly Val
145                 150                 155                 160

Leu Pro His Val Ala Met Tyr Leu Asp Ile Gly His Ala Phe Trp Leu
                165                 170                 175

Gly Trp Asp Asp Asn Arg Leu Lys Ala Gly Lys Val Tyr Ser Lys Val
            180                 185                 190

Ile Gln Ser Gly Ala Pro Gly Asn Val Arg Gly Phe Ala Ser Asn Val
        195                 200                 205

Ala Asn Tyr Thr Pro Trp Glu Asp Pro Thr Leu Ser Arg Gly Pro Asp
    210                 215                 220

Thr Glu Trp Asn Pro Cys Pro Asp Glu Lys Arg Tyr Ile Glu Ala Met
225                 230                 235                 240

Tyr Lys Asp Phe Lys Ser Ala Gly Ile Lys Ser Val Tyr Phe Ile Asp
                245                 250                 255

Asp Thr Ser Arg Asn Gly His Lys Thr Asp Arg Thr His Pro Gly Glu
            260                 265                 270

Trp Cys Asn Gln Thr Gly Val Gly Ile Gly Ala Arg Pro Gln Ala Asn
        275                 280                 285

Pro Ile Ser Gly Met Asp Tyr Leu Asp Ala Phe Tyr Trp Val Lys Pro
    290                 295                 300

Leu Gly Glu Ser Asp Gly Tyr Ser Asp Thr Thr Ala Val Arg Tyr Asp
305                 310                 315                 320

<210> SEQ ID NO 34
<211> LENGTH: 19
<212> TYPE: PRT
<213> ORGANISM: Artificial Sequence
<220> FEATURE:
<223> OTHER INFORMATION: Piromyces sp. E2 cel6A, Signal Peptide Domain
      (aa 1-19)

<400> SEQUENCE: 34

Met Lys Ala Ser Ile Ala Leu Thr Ala Ile Ala Ala Leu Ala Ala Asn
1               5                   10                  15

Ala Ser Ala

<210> SEQ ID NO 35
<211> LENGTH: 35
<212> TYPE: PRT
<213> ORGANISM: Artificial Sequence
<220> FEATURE:
<223> OTHER INFORMATION: Piromyces sp. E2 cel6A, CBM Domain (aa 21-55)

<400> SEQUENCE: 35

Cys Phe Ser Glu Arg Leu Gly Tyr Pro Cys Cys Arg Gly Asn Glu Val
1               5                   10                  15

Phe Tyr Thr Asp Asn Asp Gly Asp Trp Gly Val Glu Asn Gly Asn Trp
                20                  25                  30

Cys Gly Ile
        35

<210> SEQ ID NO 36
<211> LENGTH: 37
<212> TYPE: PRT
<213> ORGANISM: Artificial Sequence
<220> FEATURE:
<223> OTHER INFORMATION: Piromyces sp. E2 cel6A, CBM Domain (aa 62-98)

<400> SEQUENCE: 36

Thr Cys Trp Ser Gln Ala Leu Gly Tyr Pro Cys Cys Thr Ser Thr Ser
1               5                   10                  15

Asp Val Ala Tyr Val Asp Gly Asp Gly Asn Trp Gly Val Glu Asn Gly
                20                  25                  30

Asn Trp Cys Gly Ile
        35

<210> SEQ ID NO 37
<211> LENGTH: 8174
<212> TYPE: DNA
<213> ORGANISM: Artificial Sequence
<220> FEATURE:
<223> OTHER INFORMATION: pRDH150

<400> SEQUENCE: 37
agctgtttcc tgtgtgaaat tgttatccgc tcacaattcc acacaacata cgagccggaa      60
gcataaagtg taaagcctgg ggtgcctaat gagtgaggta actcacatta attgcgttgc     120
gctcactgcc cgctttccag tcgggaaacc tgtcgtgcca gctggattaa tgaatcggcc     180
aacgcgcggg gagaggcggt ttgcgtattg ggcgctcttc cgcttcctcg ctcactgact     240

```
cgctgcgctc ggtcgttcgg ctgcggcgag cggtatcagc tcactcaaag gcggtaatac      300
ggttatccac agaatcaggg gataacgcag gaaagaacat gtgagcaaaa ggccagcaaa      360
aggccaggaa ccgtaaaaag gccgcgttgc tggcgttttt ccataggctc cgcccccctg      420
acgagcatca caaaaatcga cgctcaagtc agaggtggcg aaacccgaca ggactataaa      480
gataccaggc gtttccccct ggaagctccc tcgtgcgctc tcctgttccg accctgccgc      540
ttaccggata cctgtccgcc tttctccctt cgggaagcgt ggcgctttct caatgctcac      600
gctgtaggta tctcagttcg gtgtaggtcg ttcgctccaa gctgggctgt gtgcacgaac      660 ccccccgttca gcccgaccgc tgcgccttat ccggtaacta tcgtcttgag tccaacccgg      720
taagacacga cttatcgcca ctggcagcag ccactggtaa caggattagc agagcgaggt      780
atgtaggcgg tgctacagag ttcttgaagt ggtggcctaa ctacggctac actagaagga      840
cagtatttgg tatctgcgct ctgctgaagc cagttacctt cggaaaaaga gttggtagct      900
cttgatccgg caaacaaacc accgctggta gcggtggttt ttttgtttgc aagcagcaga      960
ttacgcgcag aaaaaaagga tctcaagaag atcctttgat cttttctacg ggtctgacg     1020 ctcagtggaa cgaaaactca cgttaaggga ttttggtcat gagattatca aaaaggatct     1080
tcacctagat ccttttaaat taaaaatgaa gttttaaatc aatctaaagt atatatgagt     1140
aaacttggtc tgacagttac caatgcttaa tcagtgaggc acctatctca gcgatctgtc     1200
tatttcgttc atccatagtt gcctgactcc ccgtcgtgta gataactacg atacgggagg     1260
gcttaccatc tggccccagt gctgcaatga taccgcgaga cccacgctca ccggctccag     1320
atttatcagc aataaaccag ccagccggaa gggccgagcg cagaagtggt cctgcaactt     1380
tatccgcctc catccagtct attaattgtt gccgggaagc tagagtaagt agttcgccag     1440
ttaatagttt gcgcaacgtt gttgccattg ctacaggcat cgtggtgtca cgctcgtcgt     1500
ttggtatggc ttcattcagc tccggttccc aacgatcaag gcgagttaca tgatccccca     1560
tgttgtgcaa aaaagcggtt agctccttcg gtcctccgat cgttgtcaga agtaagttgg     1620
ccgcagtgtt atcactcatg gttatggcag cactgcataa ttctcttact gtcatgccat     1680
ccgtaagatg cttttctgtg actggtgagt actcaaccaa gtcattctga gaatagtgta     1740
tgcggcgacc gagttgctct tgcccggcgt caatacggga taataccgcg ccacatagca     1800
gaactttaaa agtgctcatc attggaaaac gttcttcggg gcgaaaactc tcaaggatct     1860
taccgctgtt gagatccagt tcgatgtaac ccactcgtgc acccaactga tcttcagcat     1920
cttttacttt caccagcgtt tctgggtgag caaaaacagg aaggcaaaat gccgcaaaaa     1980
agggaataag ggcgacacgg aaatgttgaa tactcatact cttccttttt caatattatt     2040
gaagcattta tcagggttat tgtctcatga gcggatacat atttgaatgt atttagaaaa     2100
ataaacaaat aggggttccg cgcacatttc cccgaaaagt gccacctgac gtctaagaaa     2160
ccattattat catgacatta acctataaaa ataggcgtat cacgaggccc tttcgtctcg     2220
cgcgtttcgg tgatgacggt gaaaacctct gacacatgca gctcccggag acggtcacag     2280
cttgtctgta agcggatgcc gggagcagac aagcccgtca gggcgcgtca gcgggtgttg     2340
gcgggtgtcg ggctggctt aactatgcgg catcagagca gattgtactg agagtgcacc     2400
ataacgcatt taagcataaa cacgcactat gccgttcttc tcatgtatat atatatacag     2460
gcaacacgca gatataggtg cgacgtgaac agtgagctgt atgtgcgcag ctcgcgttgc     2520
attttcggaa gcgctcgttt tcggaaacgc tttgaagttc ctattccgaa gttcctattc     2580
tctagctaga aagtatagga acttcagagc gcttttgaaa accaaaagcg ctctgaagac     2640
```

```
gcactttcaa aaaaccaaaa acgcaccgga ctgtaacgag ctactaaaat attgcgaata      2700
ccgcttccac aaacattgct caaaagtatc tctttgctat atatctctgt gctatatccc      2760
tatataacct acccatccac ctttcgctcc ttgaacttgc atctaaactc gacctctaca      2820 tttttatgt ttatctctag tattactctt tagacaaaaa aattgtagta agaactattc       2880
atagagtgaa tcgaaaacaa tacgaaaatg taaacatttc ctatacgtag tatatagaga      2940
caaaatagaa gaaccgttc ataatttct gaccaatgaa gaatcatcaa cgctatcact        3000
ttctgttcac aaagtatgcg caatccacat cggtatagaa tataatcggg gatgccttta     3060
tcttgaaaaa atgcacccgc agcttcgcta gtaatcagta aacgcgggaa gtggagtcag     3120
gcttttttta tggaagagaa aatagacacc aaagtagcct tcttctaacc ttaacggacc      3180
tacagtgcaa aaagttatca agagactgca ttatagagcg cacaaaggag aaaaaaagta     3240
atctaagatg ctttgttaga aaaatagcgc tctcgggatg catttttgta gaacaaaaaa     3300
gaagtataga ttctttgttg gtaaaatagc gctctcgcgt tgcatttctg ttctgtaaaa     3360
atgcagctca gattctttgt ttgaaaaatt agcgctctcg cgttgcattt tgtttttaca     3420
aaaatgaagc acagattctt cgttggtaaa atagcgcttt cgcgttgcat ttctgttctg     3480
taaaaatgca gctcagattc tttgtttgaa aaattagcgc tctcgcgttg cattttttgtt    3540 ctacaaaatg aagcacagat gcttcgttaa caaagatatg ctattgaagt gcaagatgga     3600
aacgcagaaa atgaaccggg gatgcgacgt gcaagattac ctatgcaata gatgcaatag      3660
tttctccagg aaccgaaata catacattgt cttccgtaaa gcgctagact atatattatt     3720
atacaggttc aaatatacta tctgtttcag ggaaaactcc caggttcgga tgttcaaaat     3780
tcaatgatgg gtaacaagag cttttcaatt catcattttt ttttattct tttttttgat      3840 ttcggtttct ttgaaatttt tttgattcgg taatctccga acagaaggaa gaacgaagga     3900
aggagcacag acttagattg gtatatatac gcatatgtag tgttgaagaa acatgaaatt     3960
gcccagtatt cttaacccaa ctgcacagaa caaaaccga aacgaagata aatcatgtcg      4020
aaagctacat ataaggaacg tgctgctact catcctagtc ctgttgctgc caagctattt     4080
aatatcatgc acgaaaagca aacaaacttg tgtgcttcat tggatgttcg taccaccaag     4140
gaattactgg agttagttga agcattaggt cccaaaattt gtttactaaa aacacatgtg     4200
gatatcttga ctgattttc catggagggc acagttaagc cgctaaaggc attatccgcc      4260
aagtacaatt ttttactctt cgaagacaga aaatttgctg acattggtaa tacagtcaaa     4320
ttgcagtact ctgcgggtgt atacagaata gcagaatggg cagacattac gaatgcacac     4380
ggtgtggtgg gcccaggtat tgttagcggt ttgaagcagg cggcagaaga agtaacaaag     4440
gaacctagag gccttttgat gttagcagaa ttgtcatgca agggctccct atctactgga     4500
gaatatacta agggtactgt tgacattgcg aagagcgaca aagattttgt tatcggcttt     4560
attgctcaaa gagacatggg tggaagagat gaaggttacg attggttgat tatgacaccc     4620
ggtgtgggtt tagatgacaa gggagacgca ttgggtcaac agtatagaac cgtggatgat     4680
gtggtctcta caggatctga cattattatt gttggaagag gactatttgc aaagggaagg     4740
gatgctaagg tagagggtga acgttacaga aaagcaggct gggaagcata tttgagaaga     4800
tgcggccagc aaaactaaaa aactgtatta taagtaaatg catgtatact aaactcacaa     4860
attagagctt caatttaatt atatcagtta ttacccctatg cggtgtgaaa taccgcacag     4920
atgcgtaagg agaaaatacc gcatcaggcg ccattcgcca ttcaggctgc gcaactgttg     4980
```

```
ggaagggcga tcggtgcggg cctcttcgct attacgccag ctggcgaagg ggggatgtgc    5040
tgcaaggcga ttaagttggg taacgccagg gttttcccag tcacgacgtt gtaaaacgac    5100
ggccagtgcc aagctttcta actgatctat ccaaaactga aaattacatt cttgattagg    5160
tttatcacag gcaaatgtaa tttgtggtat tttgccgttc aaaatctgta gaattttctc    5220
attggtcaca ttacaacctg aaaatacttt atctacaatc ataccattct tataacatgt    5280
ccccttaata ctaggatcag gcatgaacgc atcacagaca aaatcttctt gacaaacgtc    5340
acaattgatc cctccccatc cgttatcaca atgacaggtg tcattttgtg ctcttatggg    5400
acgatcctta ttaccgcttt catccggtga tagaccgcca cagagggggca gagagcaatc    5460 atcacctgca aacccttcta tacactcaca tctaccagtg tacgaattgc attcagaaaa    5520
ctgtttgcat tcaaaaatag gtagcataca attaaaacat ggcgggcacg tatcattgcc    5580
cttatcttgt gcagttagac gcgaattttt cgaagaagta ccttcaaaga atggggtctc    5640
atcttgtttt gcaagtacca ctgagcagga taataataga aatgataata tactatagta    5700
gagataacgt cgatgacttc ccatactgta attgctttta gttgtgtatt tttagtgtgc    5760
aagtttctgt aaatcgatta attttttttt cttcctctct tttattaacc ttaattttta    5820
ttttagattc ctgacttcaa ctcaagacgc acagatatta taacatctgc acaataggca    5880
tttgcaagaa ttactcgtga gtaaggaaag agtgaggaac tatcgcatac ctgcatttaa    5940
agatgccgat ttgggcgcga atcctttatt ttggcttcac cctcatacta ttatcagggc    6000
cagaaaaagg aagtgtttcc ctccttcttg aattgatgtt accctcataa agcacgtggc    6060
ctcttatcga gaaagaaatt accgtcgctc gtgatttgtt tgcaaaaaga acaaaactga    6120
aaaaacccag acacgctcga cttcctgtct tcctattgat tgcagcttcc aatttcgtca    6180
cacaacaagg tcctagcgac ggctcacagg ttttgtaaca agcaatcgaa ggttctggaa    6240
tggcgggaaa gggtttagta ccacatgcta tgatgcccac tgtgatctcc agagcaaagt    6300
tcgttcgatc gtactgttac tctctctctt tcaaacagaa ttgtccgaat cgtgtgacaa    6360
caacagcctg ttctcacaca ctcttttctt ctaaccaagg gggtggttta gtttagtaga    6420
acctcgtgaa acttacattt acatatatat aaacttgcat aaattggtca atgcaagaaa    6480
tacatatttg gtcttttcta attcgtagtt tttcaagttc ttagatgctt tcttttttctc    6540 tttttttacag atcatcaagg aagtaattat ctacttttta caacaaatat aaaacttaat    6600
taaaatgttg tctaacgttt ttttgactgc tgctttggct gctggtttgg ctcaagcttt    6660
gccacaagct actccaactc caactgctgc tccatctggt aatccatttg ctggtaagaa    6720
tttttacgct aacccatatt attcttcaga agttcatact ttggctatgc catctttgcc    6780
agcttcattg aaaccagctg ctactgctgt tgctaaagtt ggttcttttg tttggatgga    6840
tactatggct aaagttccat tgatggatac ttacttggct gatattaaag ctaaaaatgc    6900
tgctggtgct aatttgatgg gtactttcgt tgtttatgat ttgccagata gagattgtgc    6960
tgctttagct tctaatggtg aattgaaaat tgatgaaggt ggtgttgaaa aatacaagac    7020
acaatacatt gataagattg ctgctattat caaaaagtac ccagatgtta agattaattt    7080
ggctattgaa ccagattctt tggctaatat ggttactaat atgggtgttc aaaaatgttc    7140
tagagctgct ccatattaca aagaattgac tgcttatgct ttgaaaactt tgaacttcaa    7200
caacgttgac atgtatatgg atggtggtca tgctggttgg ttgggttggg atgctaatat    7260
tggtccaact gctaaattgt ttgctgaagt ttacaaagct gctggttctc aagaggtgt    7320 tagaggtatt gttacaaacg tttctaatta caacgctttg agagtttctt cttgtccatc    7380
```

```
tattactcaa ggtaacaaga attgtgatga agaaagatac attaatgctt tggctccatt    7440
gttgaaaaat gaaggttttc cagctcattt tattgttgat caaggtagat caggtaaagt    7500
tccaactaat caacaagaat ggggtgattg gtgtaatgtt tctggtgctg gttttggtac    7560
tagaccaact actaatactg gtaatgcttt gattgatgct attgtttggg ttaaaccagg    7620
tggtgaatct gatggtactt ctgatacttc tgctgcaaga tatgatgctc attgtggtag    7680
aaattctgct tttaaaccag ctccagaagc tggtacttgg tttcaagctt actttgaaat    7740
gttgttgaag aatgctaatc cagctttggc attataaggc gcgccgaatt cgagagactc    7800
gagactgaat cggatcgatc ccgggcccgt cgagggatct gcgatagatc aattttttc    7860 ttttctcttt ccccatcctt tacgctaaaa taatagttta ttttattttt tgaatatttt    7920
ttatttatat acgtatatat agactattat ttatcttta atgattatta agattttat    7980 taaaaaaaaa ttcgctcctc ttttaatgcc tttatgcagt tttttttcc cattcgatat    8040 ttctatgttc gggttcagcg tattttaagt ttaataactc gaaaattctg cgttcgttaa    8100
agcttgcatg cctgcaggtc gactctagag gatccccggg taccgagctc gaattaattc    8160
gtaatcatgg tcat                                                      8174
```

<210> SEQ ID NO 38
<211> LENGTH: 8378
<212> TYPE: DNA
<213> ORGANISM: Artificial Sequence
<220> FEATURE:
<223> OTHER INFORMATION: pRDH151

<400> SEQUENCE: 38

```
agctgtttcc tgtgtgaaat tgttatccgc tcacaattcc acacaacata cgagccggaa      60
gcataaagtg taaagcctgg ggtgcctaat gagtgaggta actcacatta attgcgttgc     120
gctcactgcc cgctttccag tcgggaaacc tgtcgtgcca gctggattaa tgaatcggcc     180
aacgcgcggg gagaggcggt ttgcgtattg ggcgctcttc cgcttcctcg ctcactgact     240
cgctgcgctc ggtcgttcgg ctgcggcgag cggtatcagc tcactcaaag gcggtaatac     300
ggttatccac agaatcaggg gataacgcag gaaagaacat gtgagcaaaa ggccagcaaa     360
aggccaggaa ccgtaaaaag gccgcgttgc tggcgttttt ccataggctc cgcccccctg     420
acgagcatca caaaaatcga cgctcaagtc agaggtggcg aaacccgaca ggactataaa     480
gataccaggc gtttccccct ggaagctccc tcgtgcgctc tcctgttccg accctgccgc     540
ttaccggata cctgtccgcc tttctccctt cgggaagcgt ggcgctttct caatgctcac     600
gctgtaggta tctcagttcg gtgtaggtcg ttcgctccaa gctgggctgt gtgcacgaac     660 ccccgttca gcccgaccgc tgcgccttat ccggtaacta tcgtcttgag tccaacccgg     720
taagacacga cttatcgcca ctggcagcag ccactggtaa caggattagc agagcgaggt     780
atgtaggcgg tgctacagag ttcttgaagt ggtggcctaa ctacggctac actagaagga     840
cagtatttgg tatctgcgct ctgctgaagc cagttacctt cggaaaaaga gttggtagct     900
cttgatccgg caaacaaacc accgctggta gcggtggttt ttttgtttgc aagcagcaga     960
ttacgcgcag aaaaaaagga tctcaagaag atcctttgat cttttctacg gggtctgacg    1020
ctcagtggaa cgaaaactca cgttaaggga ttttggtcat gagattatca aaaaggatct    1080
tcacctagat cctttaaat taaaaatgaa gttttaaatc aatctaaagt atatatgagt    1140
aaacttggtc tgacagttac caatgcttaa tcagtgaggc acctatctca gcgatctgtc    1200
```

```
tatttcgttc atccatagtt gcctgactcc ccgtcgtgta gataactacg atacgggagg   1260
gcttaccatc tggccccagt gctgcaatga taccgcgaga cccacgctca ccggctccag   1320
atttatcagc aataaaccag ccagccggaa gggccgagcg cagaagtggt cctgcaactt   1380
tatccgcctc catccagtct attaattgtt gccgggaagc tagagtaagt agttcgccag   1440
ttaatagttt gcgcaacgtt gttgccattg ctacaggcat cgtggtgtca cgctcgtcgt   1500
ttggtatggc ttcattcagc tccggttccc aacgatcaag gcgagttaca tgatccccca   1560
tgttgtgcaa aaaagcggtt agctccttcg gtcctccgat cgttgtcaga agtaagttgg   1620
ccgcagtgtt atcactcatg gttatggcag cactgcataa ttctcttact gtcatgccat   1680
ccgtaagatg cttttctgtg actggtgagt actcaaccaa gtcattctga aatagtgta   1740
tgcggcgacc gagttgctct tgcccggcgt caatacggga taataccgcg ccacatagca   1800
gaactttaaa agtgctcatc attggaaaac gttcttcggg gcgaaaactc tcaaggatct   1860
taccgctgtt gagatccagt tcgatgtaac ccactcgtgc acccaactga tcttcagcat   1920
cttttacttt caccagcgtt tctgggtgag caaaaacagg aaggcaaaat gccgcaaaaa   1980
agggaataag ggcgacacgg aaatgttgaa tactcatact cttccttttt caatattatt   2040
gaagcattta tcagggttat tgtctcatga gcggatacat atttgaatgt atttagaaaa   2100
ataaacaaat aggggttccg cgcacatttc cccgaaaagt gccacctgac gtctaagaaa   2160
ccattattat catgacatta acctataaaa ataggcgtat cacgaggccc tttcgtctcg   2220
cgcgtttcgg tgatgacggt gaaaacctct gacacatgca gctcccggag acggtcacag   2280
cttgtctgta agcggatgcc gggagcagac aagcccgtca gggcgcgtca gcgggtgttg   2340
gcgggtgtcg ggctggctt aactatgcgg catcagagca gattgtactg agagtgcacc   2400
ataacgcatt taagcataaa cacgcactat gccgttcttc tcatgtatat atatatacag   2460
gcaacacgca gatataggtg cgacgtgaac agtgagctgt atgtgcgcag ctcgcgttgc   2520
attttcggaa gcgctcgttt tcggaaacgc tttgaagttc ctattccgaa gttcctattc   2580
tctagctaga aagtatagga acttcagagc gcttttgaaa accaaaagcg ctctgaagac   2640
gcactttcaa aaaccaaaa acgcaccgga ctgtaacgag ctactaaaat attgcgaata   2700
ccgcttccac aaacattgct caaaagtatc tctttgctat atatctctgt gctatatccc   2760
tatataacct acccatccac ctttcgctcc ttgaacttgc atctaaactc gacctctaca   2820
ttttttatgt ttatctctag tattactctt tagacaaaaa aattgtagta agaactattc   2880
atagagtgaa tcgaaaacaa tacgaaaatg taaacatttc ctatacgtag tatatagaga   2940
caaaatagaa gaaaccgttc ataattttct gaccaatgaa gaatcatcaa cgctatcact   3000
ttctgttcac aaagtatgcg caatccacat cggtatagaa tataatcggg gatgcctta   3060
tcttgaaaaa atgcacccgc agcttcgcta gtaatcagta aacgcgggaa gtggagtcag   3120
gcttttttta tggaagagaa aatagacacc aaagtagcct tcttctaacc ttaacggacc   3180
tacagtgcaa aaagttatca agagactgca ttatagagcg cacaaggag aaaaaaagta   3240
atctaagatg ctttgttaga aaaatagcgc tctcgggatg cattttgta gaacaaaaaa   3300
gaagtataga ttcttgttg gtaaaatagc gctctcgcgt tgcatttctg ttctgtaaaa   3360
atgcagctca gattctttgt ttgaaaaatt agcgctctcg cgttgcattt tgtttaca   3420
aaaatgaagc acagattctt cgttggtaaa atagcgcttt cgcgttgcat ttctgttctg   3480
taaaaatgca gctcagattc tttgtttgaa aaattagcgc tctcgcgttg cattttgtt   3540
ctacaaaatg aagcacagat gcttcgttaa caaagatatg ctattgaagt gcaagatgga   3600
```

```
aacgcagaaa atgaaccggg gatgcgacgt gcaagattac ctatgcaata gatgcaatag    3660
tttctccagg aaccgaaata catacattgt cttccgtaaa gcgctagact atatattatt    3720
atacaggttc aaatatacta tctgtttcag ggaaaactcc caggttcgga tgttcaaaat    3780
tcaatgatgg gtaacaagag cttttcaatt catcattttt tttttattct tttttttgat    3840
ttcggtttct ttgaaatttt tttgattcgg taatctccga acagaaggaa gaacgaagga    3900
aggagcacag acttagattg gtatatatac gcatatgtag tgttgaagaa acatgaaatt    3960
gcccagtatt cttaacccaa ctgcacagaa caaaaaccga aacgaagata aatcatgtcg    4020
aaagctacat ataaggaacg tgctgctact catcctagtc ctgttgctgc caagctattt    4080
aatatcatgc acgaaaagca aacaaacttg tgtgcttcat tggatgttcg taccaccaag    4140
gaattactgg agttagttga agcattaggt cccaaaattt gtttactaaa aacacatgtg    4200
gatatcttga ctgattttc catggagggc acagttaagc cgctaaaggc attatccgcc    4260
aagtacaatt ttttactctt cgaagacaga aaatttgctg acattggtaa tacagtcaaa    4320
ttgcagtact ctgcgggtgt atacagaata gcagaatggg cagacattac gaatgcacac    4380
ggtgtggtgg gcccaggtat tgttagcggt ttgaagcagg cggcagaaga agtaacaaag    4440
gaacctagag gccttttgat gttagcagaa ttgtcatgca agggctccct atctactgga    4500
gaatatacta agggtactgt tgacattgcg aagagcgaca aagattttgt tatcggcttt    4560
attgctcaaa gagacatggg tggaagagat gaaggttacg attggttgat tatgacaccc    4620
ggtgtgggtt tagatgacaa gggagacgca ttgggtcaac agtatagaac cgtggatgat    4680
gtggtctcta caggatctga cattattatt gttggaagag gactatttgc aaagggaagg    4740
gatgctaagg tagagggtga acgttacaga aaagcaggct gggaagcata tttgagaaga    4800
tgcggccagc aaaactaaaa aactgtatta taagtaaatg catgtatact aaactcacaa    4860
attagagctt caatttaatt atatcagtta ttaccctatg cggtgtgaaa taccgcacag    4920
atgcgtaagg agaaaatacc gcatcaggcg ccattcgcca ttcaggctgc gcaactgttg    4980
ggaagggcga tcggtgcggg cctcttcgct attacgccag ctggcgaagg ggggatgtgc    5040
tgcaaggcga ttaagttggg taacgccagg gttttcccag tcacgacgtt gtaaaacgac    5100
ggccagtgcc aagctttcta actgatctat ccaaaactga aaattacatt cttgattagg    5160
tttatcacag gcaaatgtaa tttgtggtat tttgccgttc aaaatctgta gaattttctc    5220
attggtcaca ttacaacctg aaaatacttt atctacaatc ataccattct tataacatgt    5280
ccccttaata ctaggatcag gcatgaacgc atcacagaca aaatcttctt gacaaacgtc    5340
acaattgatc cctcccccatc cgttatcaca atgacaggtg tcattttgtg ctcttatggg    5400
acgatcctta ttaccgcttt catccggtga tagaccgcca cagaggggca gagagcaatc    5460
atcacctgca aaccccttcta tacactcaca tctaccagtg tacgaattgc attcagaaaa    5520
ctgtttgcat tcaaaaatag gtagcataca attaaaacat ggcgggcacg tatcattgcc    5580
cttatcttgt gcagttagac gcgaattttt cgaagaagta ccttcaaaga atgggggtctc    5640 atcttgtttt gcaagtacca ctgagcagga taataataga aatgataata tactatagta    5700
gagataacgt cgatgacttc ccatactgta attgctttta gttgtgtatt tttagtgtgc    5760
aagtttctgt aaatcgatta attttttttt ctttcctctt tttattaacc ttaattttta    5820
ttttagattc ctgacttcaa ctcaagacgc acagatatta taacatctgc acaataggca    5880
tttgcaagaa ttactcgtga gtaaggaaag agtgaggaac tatcgcatac ctgcatttaa    5940
```

```
agatgccgat ttgggcgcga atcctttatt ttggcttcac cctcatacta ttatcagggc    6000
cagaaaaagg aagtgtttcc ctccttcttg aattgatgtt accctcataa agcacgtggc    6060
ctcttatcga gaaagaaatt accgtcgctc gtgatttgtt tgcaaaaaga acaaaactga    6120
aaaaacccag acacgctcga cttcctgtct tcctattgat tgcagcttcc aatttcgtca    6180
cacaacaagg tcctagcgac ggctcacagg ttttgtaaca agcaatcgaa ggttctggaa    6240
tggcgggaaa gggtttagta ccacatgcta tgatgcccac tgtgatctcc agagcaaagt    6300
tcgttcgatc gtactgttac tctctctctt tcaaacagaa ttgtccgaat cgtgtgacaa    6360
caacagcctg ttctcacaca ctcttttctt ctaaccaagg gggtggttta gtttagtaga    6420
acctcgtgaa acttacatttt acatatatat aaacttgcat aaattggtca atgcaagaaa    6480
tacatatttg gtcttttcta attcgtagtt tttcaagttc ttagatgctt tcttttttctc    6540 tttttttacag atcatcaagg aagtaattat ctacttttta caacaaatat aaaacttaat    6600
taaaatgact gcttacaaat tgttttttggc tgctgctttt gctgctactg ctttggctgc    6660
tccagttgaa gaaagacaat cttgttctaa tggtgtttgg tcacaatgtg gtggtcaaaa    6720
ttggtctggt actccatgtt gtacatctgg taacaagtgt gttaaggtta atgatttcta    6780
ctctcaatgt caaccaggtt ctgctgatcc atctccaact tctactattg tttctgctac    6840
tactactaaa gctactacta caggttctgg tggttctgtt acttctccac caccagttgc    6900
tacaaacaat ccatttttctg tgttgattt gtgggcaaac aattattaca gatcagaagt    6960
ttctactttg gctattccaa aattgtctgg tgctatggct actgctgctg caaaagttgc    7020
tgatgttcca tcttttcaat ggatggatac ttacgatcat atttctttca tggaagattc    7080
tttggctgat attagaaaag caaacaaagc aggtggtaat tatgctggtc aattcgttgt    7140
ttatgatttg ccagatagag attgtgctgc tgctgcttct aatggtgaat actctttgga    7200
taaagatggt aaaaacaagt acaaagctta tattgctgat caaggtatttt tgcaagatta    7260 ctctgatact agaatcattt tggttattga accagattct ttagctaaca tggttactaa    7320
tatgaatgtt ccaaaatgtg ctaatgctgc ttctgcttac aaagaattga ctattcatgc    7380
tttgaaagaa ttgaatttgc caaacgtttc aatgtatatt gatgctggtc atggtggttg    7440
gttgggttgg ccagctaatt tgccacctgc tgctcaattg tatggtcaat tgtacaaaga    7500
tgctggtaaa ccatctagat tgagaggttt ggttactaat gtttctaatt acaacgcttg    7560
gaaattatct tctaagccag attatactga atctaaccca aattacgatg aacaaaagta    7620
cattcatgct ttatctccat tgttggaaca agaaggttgg ccaggcgcta agttcattgt    7680
tgatcaaggt agatcaggta acaaccaac tggtcaaaaa gcttggggtg attggtgtaa    7740
tgctccaggt actggttttg gtttaagacc atctgctaat actggtgatg ctttggttga    7800
tgcttttgtt tgggttaaac caggtggtga atctgatggt acttctgata cttctgctgc    7860
aagatatgat tatcattgtg gtattgatgg tgctgttaaa ccagctccag aagctggtac    7920
ttggtttcaa gcttactttg aacaattgtt gaagaatgct aatccatctt tcttgttata    7980
aggcgcgccg aattcgagag actcgagact gaatcggatc gatcccgggc ccgtcgaggg    8040
atctgcgata gatcaattttt tttctttctct ctttccccat cctttacgct aaaataatag    8100 tttatttttat ttttttgaata ttttttattt atatacgtat atatagacta ttatttatct    8160
tttaatgatt attaagattt ttattaaaaa aaaattcgct cctcttttaa tgcctttatg    8220
cagttttttt tttcccattcg atatttctat gttcgggttc agcgtatttt aagtttaata    8280
actcgaaaat tctgcgttcg ttaaagcttg catgcctgca ggtcgactct agaggatccc    8340
```
cgggtaccga gctcgaatta attcgtaatc atggtcat 8378

<210> SEQ ID NO 39
<211> LENGTH: 8363
<212> TYPE: DNA
<213> ORGANISM: Artificial Sequence
<220> FEATURE:
<223> OTHER INFORMATION: pRDH152

<400> SEQUENCE: 39

| | | |
|---|---|---|
| agctgtttcc tgtgtgaaat tgttatccgc tcacaattcc acacaacata cgagccggaa | 60 |
| gcataaagtg taaagcctgg ggtgcctaat gagtgaggta actcacatta attgcgttgc | 120 |
| gctcactgcc cgctttccag tcgggaaacc tgtcgtgcca gctggattaa tgaatcggcc | 180 |
| aacgcgcggg gagaggcggt ttgcgtattg ggcgctcttc cgcttcctcg ctcactgact | 240 |
| cgctgcgctc ggtcgttcgg ctgcggcgag cggtatcagc tcactcaaag gcggtaatac | 300 |
| ggttatccac agaatcaggg gataacgcag gaaagaacat gtgagcaaaa ggccagcaaa | 360 |
| aggccaggaa ccgtaaaaag gccgcgttgc tggcgttttt ccataggctc cgcccccctg | 420 |
| acgagcatca caaaaatcga cgctcaagtc agaggtggcg aaacccgaca ggactataaa | 480 |
| gataccaggc gtttccccct ggaagctccc tcgtgcgctc tcctgttccg accctgccgc | 540 |
| ttaccggata cctgtccgcc tttctccctt cgggaagcgt ggcgctttct caatgctcac | 600 |
| gctgtaggta tctcagttcg gtgtaggtcg ttcgctccaa gctgggctgt gtgcacgaac | 660 |
| cccccgttca gcccgaccgc tgcgccttat ccggtaacta tcgtcttgag tccaacccgg | 720 |
| taagacacga cttatcgcca ctggcagcag ccactggtaa caggattagc agagcgaggt | 780 |
| atgtaggcgg tgctacagag ttcttgaagt ggtggcctaa ctacggctac actagaagga | 840 |
| cagtatttgg tatctgcgct ctgctgaagc cagttacctt cggaaaaaga gttggtagct | 900 |
| cttgatccgg caaacaaacc accgctggta gcggtggttt ttttgtttgc aagcagcaga | 960 |
| ttacgcgcag aaaaaaagga tctcaagaag atcctttgat cttttctacg gggtctgacg | 1020 |
| ctcagtggaa cgaaaactca cgttaaggga ttttggtcat gagattatca aaaaggatct | 1080 |
| tcacctagat ccttttaaat taaaaatgaa gttttaaatc aatctaaagt atatatgagt | 1140 |
| aaacttggtc tgacagttac caatgcttaa tcagtgaggc acctatctca gcgatctgtc | 1200 |
| tatttcgttc atccatagtt gcctgactcc ccgtcgtgta gataactacg atacgggagg | 1260 |
| gcttaccatc tggccccagt gctgcaatga taccgcgaga cccacgctca ccggctccag | 1320 |
| atttatcagc aataaaccag ccagccggaa gggccgagcg cagaagtggt cctgcaactt | 1380 |
| tatccgcctc catccagtct attaattgtt gccgggaagc tagagtaagt agttcgccag | 1440 |
| ttaatagttt gcgcaacgtt gttgccattg ctacaggcat cgtggtgtca cgctcgtcgt | 1500 |
| ttggtatggc ttcattcagc tccggttccc aacgatcaag gcgagttaca tgatccccca | 1560 |
| tgttgtgcaa aaaagcggtt agctccttcg gtcctccgat cgttgtcaga agtaagttgg | 1620 |
| ccgcagtgtt atcactcatg gttatggcag cactgcataa ttctcttact gtcatgccat | 1680 |
| ccgtaagatg cttttctgtg actggtgagt actcaaccaa gtcattctga atagtgta | 1740 |
| tgcggcgacc gagttgctct tgcccggcgt caatacggga taataccgcg ccacatagca | 1800 |
| gaactttaaa agtgctcatc attggaaaac gttcttcggg gcgaaaactc tcaaggatct | 1860 |
| taccgctgtt gagatccagt tcgatgtaac ccactcgtgc acccaactga tcttcagcat | 1920 |
| cttttacttt caccagcgtt tctgggtgag caaaaacagg aaggcaaaat gccgcaaaaa | 1980 |

```
agggaataag ggcgacacgg aaatgttgaa tactcatact cttccttttt caatattatt      2040
gaagcattta tcagggttat tgtctcatga gcggatacat atttgaatgt atttagaaaa      2100
ataaacaaat aggggttccg cgcacatttc cccgaaaagt gccacctgac gtctaagaaa      2160
ccattattat catgacatta acctataaaa ataggcgtat cacgaggccc tttcgtctcg      2220
cgcgtttcgg tgatgacggt gaaaacctct gacacatgca gctcccggag acggtcacag      2280
cttgtctgta agcggatgcc gggagcagac aagcccgtca gggcgcgtca gcgggtgttg      2340
gcgggtgtcg gggctggctt aactatgcgg catcagagca gattgtactg agagtgcacc      2400
ataacgcatt taagcataaa cacgcactat gccgttcttc tcatgtatat atatatacag      2460
gcaacacgca gatataggtg cgacgtgaac agtgagctgt atgtgcgcag ctcgcgttgc      2520
attttcggaa gcgctcgttt cggaaacgc tttgaagttc ctattccgaa gttcctattc       2580
tctagctaga aagtatagga acttcagagc gcttttgaaa accaaaagcg ctctgaagac      2640
gcactttcaa aaaccaaaa acgcaccgga ctgtaacgag ctactaaaat attgcgaata       2700
ccgcttccac aaacattgct caaaagtatc tctttgctat atatctctgt gctatatccc      2760
tatataacct acccatccac ctttcgctcc ttgaacttgc atctaaactc gacctctaca      2820
tttttttatgt ttatctctag tattactctt tagacaaaaa aattgtagta agaactattc     2880
atagagtgaa tcgaaaacaa tacgaaaatg taaacatttc ctatacgtag tatatagaga      2940
caaaatagaa gaaccgttc ataatttct gaccaatgaa gaatcatcaa cgctatcact         3000
ttctgttcac aaagtatgcg caatccacat cggtatagaa tataatcggg gatgccttta      3060
tcttgaaaaa atgcacccgc agcttcgcta gtaatcagta aacgcgggaa gtggagtcag      3120
gcttttttta tggaagagaa aatagacacc aaagtagcct tcttctaacc ttaacggacc      3180
tacagtgcaa aaagttatca agagactgca ttatagagcg cacaaaggag aaaaaaagta      3240
atctaagatg ctttgttaga aaaatagcgc tctcgggatg cattttttgta gaacaaaaaa     3300
gaagtataga ttcttttgttg gtaaaatagc gctctcgcgt tgcatttctg ttctgtaaaa     3360
atgcagctca gattctttgt ttgaaaaatt agcgctctcg cgttgcattt tgttttaca      3420
aaaatgaagc acagattctt cgttggtaaa atagcgcttt cgcgttgcat ttctgttctg      3480
taaaaatgca gctcagattc tttgtttgaa aaattagcgc tctcgcgttg cattttttgtt    3540
ctacaaaatg aagcacagat gcttcgttaa caaagatatg ctattgaagt gcaagatgga     3600
aacgcagaaa atgaaccggg gatgcgacgt gcaagattac ctatgcaata gatgcaatag     3660
tttctccagg aaccgaaata catacattgt cttccgtaaa gcgctagact atatattatt     3720
atacaggttc aaatatacta tctgtttcag ggaaaactcc caggttcgga tgttcaaaat     3780
tcaatgatgg gtaacaagag cttttcaatt catcattttt tttttattct ttttttttgat    3840
ttcggtttct ttgaaatttt tttgattcgg taatctccga acagaaggaa gaacgaagga     3900
aggagcacag acttagattg gtatatatac gcatatgtag tgttgaagaa acatgaaatt     3960
gcccagtatt cttaacccaa ctgcacagaa caaaaaccga aacgaagata aatcatgtcg     4020
aaagctacat ataaggaacg tgctgctact catcctagtc ctgttgctgc caagctattt     4080
aatatcatgc acgaaaagca aacaaacttg tgtgcttcat tggatgttcg taccaccaag     4140
gaattactgg agttagttga agcattaggt cccaaaattt gtttactaaa aacacatgtg     4200
gatatcttga ctgattttc catggagggc acagttaagc cgctaaaggc attatccgcc       4260
aagtacaatt ttttactctt cgaagacaga aaatttgctg acattggtaa tacagtcaaa     4320
ttgcagtact ctgcgggtgt atacagaata gcagaatggg cagacattac gaatgcacac     4380
```

```
ggtgtggtgg gcccaggtat tgttagcggt ttgaagcagg cggcagaaga agtaacaaag    4440
gaacctagag gccttttgat gttagcagaa ttgtcatgca agggctccct atctactgga    4500
gaatatacta agggtactgt tgacattgcg aagagcgaca aagattttgt tatcggcttt    4560
attgctcaaa gagacatggg tggaagagat gaaggttacg attggttgat tatgacaccc    4620
ggtgtgggtt tagatgacaa gggagacgca ttgggtcaac agtatagaac cgtggatgat    4680
gtggtctcta caggatctga cattattatt gttggaagag gactatttgc aaagggaagg    4740
gatgctaagg tagagggtga acgttacaga aaagcaggct gggaagcata tttgagaaga    4800
tgcggccagc aaaactaaaa aactgtatta taagtaaatg catgtatact aaactcacaa    4860
attagagctt caatttaatt atatcagtta ttaccctatg cggtgtgaaa taccgcacag    4920
atgcgtaagg agaaaatacc gcatcaggcg ccattcgcca ttcaggctgc gcaactgttg    4980
ggaagggcga tcggtgcggg cctcttcgct attacgccag ctggcgaagg ggggatgtgc    5040
tgcaaggcga ttaagttggg taacgccagg gttttcccag tcacgacgtt gtaaaacgac    5100
ggccagtgcc aagctttcta actgatctat ccaaaactga aaattacatt cttgattagg    5160
tttatcacag gcaaatgtaa tttgtggtat tttgccgttc aaaatctgta gaattttctc    5220
attggtcaca ttacaacctg aaaatacttt atctacaatc ataccattct tataacatgt    5280
ccccttaata ctaggatcag gcatgaacgc atcacagaca aaatcttctt gacaaacgtc    5340
acaattgatc cctccccatc cgttatcaca atgacaggtg tcattttgtg ctcttatggg    5400
acgatcctta ttaccgcttt catccggtga tagaccgcca cagaggggca gagagcaatc    5460
atcacctgca aaccettcta tacactcaca tctaccagtg tacgaattgc attcagaaaa    5520
ctgtttgcat tcaaaaatag gtagcataca attaaaacat ggcgggcacg tatcattgcc    5580
cttatcttgt gcagttagac gcgaattttt cgaagaagta ccttcaaaga atgggtctc    5640 atcttgtttt gcaagtacca ctgagcagga taataataga aatgataata tactatagta    5700
gagataacgt cgatgacttc ccatactgta attgctttta gttgtgtatt tttagtgtgc    5760
aagtttctgt aaatcgatta atttttttt ctttcctctt tttattaacc ttaattttta    5820
ttttagattc ctgacttcaa ctcaagacgc acagatatta taacatctgc acaataggca    5880
tttgcaagaa ttactcgtga gtaaggaaag agtgaggaac tatcgcatac ctgcatttaa    5940
agatgccgat ttgggcgcga atcctttatt ttggcttcac cctcatacta ttatcagggc    6000
cagaaaaagg aagtgtttcc ctccttcttg aattgatgtt accctcataa agcacgtggc    6060
ctcttatcga gaaagaaatt accgtcgctc gtgatttgtt tgcaaaaaga acaaaactga    6120
aaaaacccag acacgctcga cttcctgtct tcctattgat tgcagcttcc aatttcgtca    6180
cacaacaagg tcctagcgac ggctcacagg ttttgtaaca agcaatcgaa ggttctggaa    6240
tggcgggaaa gggtttagta ccacatgcta tgatgcccac tgtgatctcc agagcaaagt    6300
tcgttcgatc gtactgttac tctctctctt tcaaacagaa ttgtccgaat cgtgtgacaa    6360
caacagcctg ttctcacaca ctcttttctt ctaaccaagg gggtggttta gtttagtaga    6420
acctcgtgaa acttacattt acatatatat aaacttgcat aaattggtca atgcaagaaa    6480
tacatatttg gtcttttcta attcgtagtt tttcaagttc ttagatgctt tcttttctc     6540 tttttttacag atcatcaagg aagtaattat ctacttttta caacaaatat aaaacttaat    6600
taaaatgaag tctgctgctt ttttggctgc tttagctgct attttgccag cttacgttgc    6660
tggtcaagct caaacttggg ctcaatgtgg tggtattggt tttactggtc caactacttg    6720
```

```
tgttgctggt tctgtttgta ctaaacaaaa cgattactac tctcaatgta ttccaggttc    6780
tgctactact ccaacttctg ctccaacatc tgcaccaact tctcaaccat acaaccatc    6840 ttctacttca tctgctccat ctggtccatc ttctacacca actccatctg ctaacaatcc    6900
atggactggt tatcaaattt acttgtctcc atactatgct aatgaagttg ctgcagctgc    6960
taaagctatt actgatccaa cttggctgc taaagcagct tctgttgcta atattccaaa    7020
tttcacttgg ttggattctg tttctaaaat tgctgatttg aaaacttatt tggctgatgc    7080
ttctgctttg ggtaaatctt ctggtcaaaa gcaattgttg caaattgttg tttatgattt    7140
gccagataga gattgtgctg caaaagcttc taatggtgaa ttttctattg ctgataatgg    7200
tttggctaac taccaaaact acattgatca aattgttgct gctgttaaac aatttccaga    7260
tgttagagtt gttgctgtta ttgaaccaga ttctttggct aatttggtta caaatttaaa    7320
cgttcaaaag tgtgctaatg ctaaatctac ttacttgact gctgttaatt atgctttgaa    7380
gcaattatct tctgttggtg tttatcaata tatggatgct ggtcatgctg gttggttggg    7440
ttggccagct aatttaactc cagctgctca attgttgtct caagtttatt ctgatgctgg    7500
taaatctcca ttcattaagg gtttggctac taatgttgct aattacaatg ctttgtctgc    7560
tgcttctcca gatccaatta ctcaaggtga tccaaattac gatgaaattc attacattaa    7620
tgctttggct ccagctttgc aatctgctgg ttttccagct acttttattg ttgatcaagg    7680
tagatcaggt caacaaaatc atagacaaca atgggtgat tggtgtaaca ttaaaggtgc    7740
tggttttggt actagaccaa ctactaaatac tggttcttct ttgattgatt ctattgtttg    7800
ggttaaacca ggtggtgaat ctgatggtac ttctaattct tcatctccaa gatttgattc    7860
tacttgttct ttgtctgatg ctactcaacc agctccagaa gctggtactt ggtttcaagc    7920
ttactttgaa actttggttt ctaaagctaa tccaccattg ttataaggcg cgccgaattc    7980
gagagactcg agactgaatc ggatcgatcc cgggcccgtc gagggatctg cgatagatca    8040 attttttct tttctctttc cccatccttt acgctaaaat aatagtttat tttattttt    8100 gaatattttt tatttatata cgtatatata gactattatt tatcttttaa tgattattaa    8160
gatttttatt aaaaaaaat tcgctcctct tttaatgcct ttatgcagtt ttttttccc    8220 attcgatatt tctatgttcg ggttcagcgt attttaagtt taataactcg aaaattctgc    8280
gttcgttaaa gcttgcatgc ctgcaggtcg actctagagg atccccgggt accgagctcg    8340
aattaattcg taatcatggt cat                                           8363
```

<210> SEQ ID NO 40
<211> LENGTH: 8333
<212> TYPE: DNA
<213> ORGANISM: Artificial Sequence
<220> FEATURE:
<223> OTHER INFORMATION: pRDH153

<400> SEQUENCE: 40

```
agctgtttcc tgtgtgaaat tgttatccgc tcacaattcc acacaacata cgagccggaa      60
gcataaagtg taaagcctgg ggtgcctaat gagtgaggta actcacatta attgcgttgc     120
gctcactgcc cgctttccag tcgggaaacc tgtcgtgcca gctggattaa tgaatcggcc     180
aacgcgcggg gagaggcggt ttgcgtattg ggcgctcttc cgcttcctcg ctcactgact     240
cgctgcgctc ggtcgttcgg ctgcggcgag cggtatcagc tcactcaaag gcggtaatac     300
ggttatccac agaatcaggg gataacgcag gaaagaacat gtgagcaaaa ggccagcaaa     360
aggccaggaa ccgtaaaaag gccgcgttgc tggcgttttt ccataggctc cgcccccctg     420
```

```
acgagcatca caaaaatcga cgctcaagtc agaggtggcg aaacccgaca ggactataaa    480
gataccaggc gtttccccct ggaagctccc tcgtgcgctc tcctgttccg accctgccgc    540
ttaccggata cctgtccgcc tttctccctt cgggaagcgt ggcgctttct caatgctcac    600
gctgtaggta tctcagttcg gtgtaggtcg ttcgctccaa gctgggctgt gtgcacgaac    660
cccccgttca gcccgaccgc tgcgccttat ccggtaacta tcgtcttgag tccaacccgg    720
taagacacga cttatcgcca ctggcagcag ccactggtaa caggattagc agagcgaggt    780
atgtaggcgg tgctacagag ttcttgaagt ggtggcctaa ctacggctac actagaagga    840
cagtatttgg tatctgcgct ctgctgaagc cagttacctt cggaaaaaga gttggtagct    900
cttgatccgg caaacaaacc accgctggta gcggtggttt ttttgtttgc aagcagcaga    960
ttacgcgcag aaaaaaagga tctcaagaag atcctttgat cttttctacg gggtctgacg   1020
ctcagtggaa cgaaaactca cgttaaggga ttttggtcat gagattatca aaaaggatct   1080
tcacctagat ccttttaaat taaaatgaa gttttaaatc aatctaaagt atatatgagt     1140
aaacttggtc tgacagttac caatgcttaa tcagtgaggc acctatctca gcgatctgtc   1200
tatttcgttc atccatagtt gcctgactcc ccgtcgtgta gataactacg atacgggagg   1260
gcttaccatc tggccccagt gctgcaatga taccgcgaga cccacgctca ccggctccag   1320
atttatcagc aataaaccag ccagccggaa gggccgagcg cagaagtggt cctgcaactt   1380
tatccgcctc catccagtct attaattgtt gccgggaagc tagagtaagt agttcgccag   1440
ttaatagttt gcgcaacgtt gttgccattg ctacaggcat cgtggtgtca cgctcgtcgt   1500
ttggtatggc ttcattcagc tccggttccc aacgatcaag gcgagttaca tgatccccca   1560
tgttgtgcaa aaaagcggtt agctccttcg gtcctccgat cgttgtcaga agtaagttgg   1620
ccgcagtgtt atcactcatg gttatggcag cactgcataa ttctcttact gtcatgccat   1680
ccgtaagatg cttttctgtg actggtgagt actcaaccaa gtcattctga aatagtgta    1740 tgcggcgacc gagttgctct tgcccggcgt caatacggga taataccgcg ccacatagca   1800
gaactttaaa agtgctcatc attggaaaac gttcttcggg gcgaaaactc tcaaggatct   1860
taccgctgtt gagatccagt tcgatgtaac ccactcgtgc acccaactga tcttcagcat   1920
cttttacttt caccagcgtt tctgggtgag caaaaacagg aaggcaaaat gccgcaaaaa   1980
agggaataag ggcgacacgg aaatgttgaa tactcatact cttcctttt caatattatt     2040 gaagcattta tcagggttat tgtctcatga gcggatacat atttgaatgt atttagaaaa   2100
ataaacaaat aggggttccg cgcacatttc cccgaaaagt gccacctgac gtctaagaaa   2160
ccattattat catgacatta acctataaaa ataggcgtat cacgaggccc tttcgtctcg   2220
cgcgtttcgg tgatgacggt gaaaacctct gacacatgca gctcccggag acggtcacag   2280
cttgtctgta agcggatgcc gggagcagac aagcccgtca gggcgcgtca gcgggtgttg   2340
gcgggtgtcg ggctggctt aactatgcgg catcagagca gattgtactg agagtgcacc    2400
ataacgcatt taagcataaa cacgcactat gccgttcttc tcatgtatat atatatacag   2460
gcaacacgca gatataggtg cgacgtgaac agtgagctgt atgtgcgcag ctcgcgttgc   2520
attttcggaa gcgctcgttt tcggaaacgc tttgaagttc ctattccgaa gttcctattc   2580
tctagctaga aagtatagga acttcagagc gcttttgaaa accaaaagcg ctctgaagac   2640
gcactttcaa aaaccaaaa acgcaccgga ctgtaacgag ctactaaaat attgcgaata    2700
ccgcttccac aaacattgct caaaagtatc tctttgctat atatctctgt gctatatccc   2760
```

```
tatataacct acccatccac ctttcgctcc ttgaacttgc atctaaactc gacctctaca    2820
tttttttatgt ttatctctag tattactctt tagacaaaaa aattgtagta agaactattc    2880
atagagtgaa tcgaaaacaa tacgaaaatg taaacatttc ctatacgtag tatatagaga    2940
caaaatagaa gaaaccgttc ataatttct gaccaatgaa gaatcatcaa cgctatcact     3000
ttctgttcac aaagtatgcg caatccacat cggtatagaa tataatcggg gatgccttta    3060
tcttgaaaaa atgcacccgc agcttcgcta gtaatcagta aacgcgggaa gtggagtcag    3120
gcttttttta tggaagagaa aatagacacc aaagtagcct tcttctaacc ttaacggacc    3180
tacagtgcaa aaagttatca agagactgca ttatagagcg cacaaaggag aaaaaaagta    3240
atctaagatg ctttgttaga aaaatagcgc tctcgggatg catttttgta gaacaaaaaa    3300
gaagtataga ttctttgttg gtaaaatagc gctctcgcgt tgcatttctg ttctgtaaaa    3360
atgcagctca gattctttgt ttgaaaaatt agcgctctcg cgttgcattt ttgttttaca    3420
aaaatgaagc acagattctt cgttggtaaa atagcgcttt cgcgttgcat ttctgttctg    3480
taaaaatgca gctcagattc tttgtttgaa aaattagcgc tctcgcgttg cattttttgtt   3540
ctacaaaatg aagcacagat gcttcgttaa caagatatg ctattgaagt gcaagatgga     3600
aacgcagaaa atgaaccggg gatgcgacgt gcaagattac ctatgcaata gatgcaatag    3660
tttctccagg aaccgaaata catacattgt cttccgtaaa gcgctagact atatattatt    3720
atacaggttc aaatatacta tctgtttcag ggaaaactcc caggttcgga tgttcaaaat    3780
tcaatgatgg gtaacaagag cttttcaatt catcattttt tttttattct ttttttttgat   3840
ttcggttttct ttgaaatttt tttgattcgg taatctccga acagaaggaa gaacgaagga   3900
aggagcacag acttagattg gtatatatac gcatatgtag tgttgaagaa acatgaaatt    3960
gcccagtatt cttaacccaa ctgcacagaa caaaaaccga aacgaagata aatcatgtcg    4020
aaagctacat ataaggaacg tgctgctact catcctagtc ctgttgctgc caagctattt    4080
aatatcatgc acgaaaagca aacaaacttg tgtgcttcat tggatgttcg taccaccaag    4140
gaattactgg agttagttga agcattaggt cccaaaattt gtttactaaa aacacatgtg    4200
gatatcttga ctgatttttc catggagggc acagttaagc cgctaaaggc attatccgcc    4260
aagtacaatt ttttactctt cgaagacaga aaatttgctg acattggtaa tacagtcaaa    4320
ttgcagtact ctgcgggtgt atacagaata gcagaatggg cagacattac gaatgcacac    4380
ggtgtggtgg gcccaggtat tgttagcggt ttgaagcagg cggcagaaga agtaacaaag    4440
gaacctagag gccttttgat gttagcagaa ttgtcatgca agggctccct atctactgga    4500
gaatatacta agggtactgt tgacattgcg aagagcgaca aagattttgt tatcggcttt    4560
attgctcaaa gagacatggg tggaagagat gaaggttacg attggttgat tatgacaccc    4620
ggtgtgggtt tagatgacaa gggagacgca ttgggtcaac agtatagaac cgtggatgat    4680
gtggtctcta caggatctga cattattatt gttggaagag gactatttgc aaagggaagg    4740
gatgctaagg tagagggtga acgttacaga aaagcaggct gggaagcata tttgagaaga    4800
tgcggccagc aaaactaaaa aactgtatta taagtaaatg catgtatact aaactcacaa    4860
attagagctt caatttaatt atatcagtta ttaccctatg cggtgtgaaa taccgcacag    4920
atgcgtaagg agaaaatacc gcatcaggcg ccattcgcca tcaggctgc gcaactgttg     4980
ggaagggcga tcggtgcggg cctcttcgct attacgccag ctggcgaagg gggatgtgc     5040
tgcaaggcga ttaagttggg taacgccagg gttttcccag tcacgacgtt gtaaaacgac    5100
ggccagtgcc aagcttttcta actgatctat ccaaaactga aaattacatt cttgattagg    5160
```

```
tttatcacag gcaaatgtaa tttgtggtat tttgccgttc aaaatctgta gaattttctc   5220
attggtcaca ttacaacctg aaaatacttt atctacaatc ataccattct tataacatgt   5280
ccccttaata ctaggatcag gcatgaacgc atcacagaca aaatcttctt gacaaacgtc   5340
acaattgatc cctccccatc cgttatcaca atgacaggtg tcattttgtg ctcttatggg   5400
acgatcctta ttaccgcttt catccggtga tagaccgcca cagaggggca gagagcaatc   5460
atcacctgca aacccttcta tacactcaca tctaccagtg tacgaattgc attcagaaaa   5520
ctgtttgcat tcaaaaatag gtagcataca attaaacat ggcgggcacg tatcattgcc   5580
cttatcttgt gcagttagac gcgaattttt cgaagaagta ccttcaaaga atggggtctc   5640
atcttgtttt gcaagtacca ctgagcagga taataataga aatgataata tactatagta   5700
gagataacgt cgatgacttc ccatactgta attgctttta gttgtgtatt tttagtgtgc   5760
aagtttctgt aaatcgatta attttttttt ctttcctctt tttattaacc ttaattttta   5820
ttttagattc ctgacttcaa ctcaagacgc acagatatta taacatctgc acaataggca   5880
tttgcaagaa ttactcgtga gtaaggaaag agtgaggaac tatcgcatac ctgcatttaa   5940
agatgccgat ttgggcgcga atcctttatt ttggcttcac cctcatacta ttatcagggc   6000
cagaaaaagg aagtgtttcc ctccttcttg aattgatgtt accctcataa agcacgtggc   6060
ctcttatcga gaaagaaatt accgtcgctc gtgatttgtt tgcaaaaaga acaaaactga   6120
aaaaacccag acacgctcga cttcctgtct tcctattgat tgcagcttcc aatttcgtca   6180
cacaacaagg tcctagcgac ggctcacagg ttttgtaaca agcaatcgaa ggttctggaa   6240
tggcgggaaa gggtttagta ccacatgcta tgatgcccac tgtgatctcc agagcaaagt   6300
tcgttcgatc gtactgttac tctctctctt tcaaacagaa ttgtccgaat cgtgtgacaa   6360
caacagcctg ttctcacaca ctctttttctt ctaaccaagg gggtggttta gtttagtaga   6420
acctcgtgaa acttacattt acatatatat aaacttgcat aaattggtca atgcaagaaa   6480
tacatatttg gtcttttcta attcgtagtt tttcaagttc ttagatgctt tcttttttctc   6540 tttttttacag atcatcaagg aagtaattat ctacttttta caacaaatat aaaacttaat   6600
taaaatgtct agattctctg ctttgactgc tttgttgttg tctttgccat tgttggctat   6660
tgctcaatct ccattgtatg gtcaatgtgg tggtaatggt tggactggtc caaaaacttg   6720
tgtttctggt gctacttgta ctgttattaa tgattggtat tggcaatgtt tgccaggtaa   6780
tggtccaact tcttcttctc caacttctac tccaactaca actactacta ctggtggtcc   6840
acaaccaact gttccagctg ctggtaatcc atatactggt tacgaaattt acttgtctcc   6900
atattatgct gctgaagctc aagctgctgc tgctcaaatt tctgatgcta ctcaaaaagc   6960
taaagctttg aaagttgctc aaattccaac ttttacttgg tttgatgtta ttgctaaaac   7020
ttctactttg ggtgattatt tggctgaagc ttctgctttg ggtaaatctt ctggtaaaaa   7080
gtacttggtt caaattgttg tttatgattt gccagataga gattgtgctg ctttggcttc   7140
taatggtgaa ttttctattg ctaacaacgg tttgaacaat tacaaaggtt acattgatca   7200
attggttgca caaattaaga aatacccaga tgttagagtt gttgctgtta ttgaaccaga   7260 ttcctttggct aatttggtta caaatttgaa cgtttctaag tgtgctaatg ctcaaactgc   7320
ttacaaagct ggtgttactt atgctttgca acaattgaac tctgttggtg tttacatgta   7380
tttggatgct ggtcatgctg gttggttggg ttggccagct aatttgaatc agctgctca   7440 attgttttct caattgtata gagatgctgg ttctccacaa tacgttagag gtttggctac   7500
```

```
taatgttgct aattacaatg ctttgtctgc ttcttcacca gatccagtta ctcaaggtaa    7560
tccaaattac gatgaattgc attacattaa tgctttggct ccagctttgc aatctggtgg    7620
ttttccagct cattttattg ttgatcaagg tagatcaggt gttcaaaaca ttagacaaca    7680
atggggtgat tggtgtaatg ttaaaggtgc tggttttggt caaagaccaa ctttatctac    7740
tggttcttct ttgattgatg ctattgtttg gattaaacca ggtggtgaat gtgatggtac    7800
tactaataca tcttctccaa gatatgattc tcattgtggt ttgtctgatg ctactccaaa    7860
tgctcctgaa gctggtcaat ggtttcaagc ttactttgaa actttggtta gaaatgcttc    7920
tccaccattg ttataaggcg cgccgaattc gagagactcg agactgaatc ggatcgatcc    7980
cgggcccgtc gagggatctg cgatagatca atttttttct ttctctttc cccatccttt    8040 acgctaaaat aatagtttat tttatttttt gaatattttt tatttatata cgtatatata    8100
gactattatt tatcttttaa tgattattaa gatttttatt aaaaaaaaat tcgctcctct    8160
tttaatgcct ttatgcagtt ttttttttccc attcgatatt tctatgttcg ggttcagcgt    8220 atttaagtt taataactcg aaaattctgc gttcgttaaa gcttgcatgc ctgcaggtcg    8280
actctagagg atccccgggt accgagctcg aattaattcg taatcatggt cat          8333
```

<210> SEQ ID NO 41
<211> LENGTH: 8480
<212> TYPE: DNA
<213> ORGANISM: Artificial Sequence
<220> FEATURE:
<223> OTHER INFORMATION: pRDH154

<400> SEQUENCE: 41

```
agctgtttcc tgtgtgaaat tgttatccgc tcacaattcc acacaacata cgagccggaa      60
gcataaagtg taaagcctgg ggtgcctaat gagtgaggta actcacatta attgcgttgc     120
gctcactgcc cgctttccag tcgggaaacc tgtcgtgcca gctggattaa tgaatcggcc     180
aacgcgcggg gagaggcggt ttgcgtattg ggcgctcttc cgcttcctcg ctcactgact     240
cgctgcgctc ggtcgttcgg ctgcggcgag cggtatcagc tcactcaaag gcggtaatac     300
ggttatccac agaatcaggg gataacgcag gaaagaacat gtgagcaaaa ggccagcaaa     360
aggccaggaa ccgtaaaaag gccgcgttgc tggcgttttt ccataggctc cgcccccctg     420
acgagcatca caaaaatcga cgctcaagtc agaggtggcg aaacccgaca ggactataaa     480
gataccaggc gtttccccct ggaagctccc tcgtgcgctc tcctgttccg accctgccgc     540
ttaccggata cctgtccgcc tttctccctt cgggaagcgt ggcgctttct caatgctcac     600
gctgtaggta tctcagttcg gtgtaggtcg ttcgctccaa gctgggctgt gtgcacgaac     660 ccccgttca gcccgaccgc tgcgccttat ccggtaacta tcgtcttgag tccaacccgg     720
taagacacga cttatcgcca ctggcagcag ccactggtaa caggattagc agagcgaggt     780
atgtaggcgg tgctacagag ttcttgaagt ggtggcctaa ctacggctac actagaagga     840
cagtatttgg tatctgcgct ctgctgaagc cagttacctt cggaaaaaga gttggtagct     900
cttgatccgg caaacaaacc accgctggta gcggtggttt ttttgtttgc aagcagcaga     960
ttacgcgcag aaaaaaagga tctcaagaag atcctttgat cttttctacg ggtctgacg    1020 ctcagtggaa cgaaaactca cgttaaggga ttttggtcat gagattatca aaaaggatct    1080
tcacctagat ccttttaaat taaaaatgaa gttttaaatc aatctaaagt atatatgagt    1140
aaacttggtc tgacagttac caatgcttaa tcagtgaggc acctatctca gcgatctgtc    1200
tatttcgttc atccatagtt gcctgactcc ccgtcgtgta gataactacg atacgggagg    1260
```

```
gcttaccatc tggccccagt gctgcaatga taccgcgaga cccacgctca ccggctccag   1320
atttatcagc aataaaccag ccagccggaa gggccgagcg cagaagtggt cctgcaactt   1380
tatccgcctc catccagtct attaattgtt gccgggaagc tagagtaagt agttcgccag   1440
ttaatagttt gcgcaacgtt gttgccattg ctacaggcat cgtggtgtca cgctcgtcgt   1500
ttggtatggc ttcattcagc tccggttccc aacgatcaag gcgagttaca tgatccccca   1560
tgttgtgcaa aaagcggtt agctccttcg gtcctccgat cgttgtcaga agtaagttgg   1620
ccgcagtgtt atcactcatg gttatggcag cactgcataa ttctcttact gtcatgccat   1680
ccgtaagatg ctttttctgtg actggtgagt actcaaccaa gtcattctga aatagtgta   1740 tgcggcgacc gagttgctct tgcccggcgt caatacggga taataccgcg ccacatagca   1800
gaactttaaa agtgctcatc attggaaaac gttcttcggg gcgaaaactc tcaaggatct   1860
taccgctgtt gagatccagt tcgatgtaac ccactcgtgc acccaactga tcttcagcat   1920
cttttacttt caccagcgtt tctgggtgag caaaaacagg aaggcaaaat gccgcaaaaa   1980
agggaataag ggcgacacgg aaatgttgaa tactcatact cttccttttt caatattatt   2040
gaagcattta tcagggttat tgtctcatga gcggatacat atttgaatgt atttagaaaa   2100
ataaacaaat aggggttccg cgcacatttc cccgaaaagt gccacctgac gtctaagaaa   2160
ccattattat catgacatta acctataaaa ataggcgtat cacgaggccc tttcgtctcg   2220
cgcgtttcgg tgatgacggt gaaaacctct gacacatgca gctcccggag acggtcacag   2280
cttgtctgta gcggatgcc gggagcagac aagcccgtca gggcgcgtca gcgggtgttg   2340
gcgggtgtcg ggctggctt aactatgcgg catcagagca gattgtactg agagtgcacc   2400
ataacgcatt taagcataaa cacgcactat gccgttcttc tcatgtatat atatatacag   2460
gcaacacgca gatataggtg cgacgtgaac agtgagctgt atgtgcgcag ctcgcgttgc   2520
attttcggaa gcgctcgttt tcggaaacgc tttgaagttc ctattccgaa gttcctattc   2580
tctagctaga agtatagga acttcagagc gcttttgaaa accaaaagcg ctctgaagac   2640
gcactttcaa aaaccaaaa acgcaccgga ctgtaacgag ctactaaaat attgcgaata   2700
ccgcttccac aaacattgct caaaagtatc tctttgctat atatctctgt gctatatccc   2760
tatataacct acccatccac ctttcgctcc ttgaacttgc atctaaactc gacctctaca   2820 tttttttatgt ttatctctag tattactctt tagacaaaaa aattgtagta agaactattc   2880
atagagtgaa tcgaaaacaa tacgaaaatg taaacatttc ctatacgtag tatatagaga   2940
caaaatagaa gaaaccgttc ataatttct gaccaatgaa gaatcatcaa cgctatcact   3000
ttctgttcac aaagtatgcg caatccacat cggtatagaa tataatcggg gatgccttta   3060
tcttgaaaaa atgcacccgc agcttcgcta gtaatcagta aacgcgggaa gtggagtcag   3120
gcttttttta tggaagagaa aatagacacc aaagtagcct tcttctaacc ttaacggacc   3180
tacagtgcaa aaagttatca agagactgca ttatagagcg cacaaggag aaaaaaagta   3240 atctaagatg ctttgttaga aaaatagcgc tctcgggatg cattttgta gaacaaaaaa   3300 gaagtataga ttcttgttg gtaaaatagc gctctcgcgt tgcatttctg ttctgtaaaa   3360
atgcagctca gattctttgt ttgaaaaatt agcgctctcg cgttgcattt ttgttttaca   3420
aaaatgaagc acagattctt cgttggtaaa atagcgcttt cgcgttgcat ttctgttctg   3480
taaaaatgca gctcagattc tttgtttgaa aaattagcgc tctcgcgttg cattttgtt   3540 ctacaaaatg aagcacagat gcttcgttaa caaagatatg ctattgaagt gcaagatgga   3600
```

```
aacgcagaaa atgaaccggg gatgcgacgt gcaagattac ctatgcaata gatgcaatag    3660
tttctccagg aaccgaaata catacattgt cttccgtaaa gcgctagact atatattatt    3720
atacaggttc aaatatacta tctgtttcag ggaaaactcc caggttcgga tgttcaaaat    3780
tcaatgatgg gtaacaagag cttttcaatt catcattttt tttttattct tttttttgat    3840
ttcggtttct ttgaaatttt tttgattcgg taatctccga acagaaggaa gaacgaagga    3900
aggagcacag acttagattg gtatatatac gcatatgtag tgttgaagaa acatgaaatt    3960
gcccagtatt cttaacccaa ctgcacagaa caaaaaccga aacgaagata aatcatgtcg    4020
aaagctacat ataaggaacg tgctgctact catcctagtc ctgttgctgc caagctattt    4080
aatatcatgc acgaaaagca aacaaacttg tgtgcttcat tggatgttcg taccaccaag    4140
gaattactgg agttagttga agcattaggt cccaaaattt gtttactaaa aacacatgtg    4200
gatatcttga ctgatttttc catggagggc acagttaagc cgctaaaggc attatccgcc    4260
aagtacaatt ttttactctt cgaagacaga aaatttgctg acattggtaa tacagtcaaa    4320
ttgcagtact ctgcgggtgt atacagaata gcagaatggg cagacattac gaatgcacac    4380
ggtgtggtgg gcccaggtat tgttagcggt ttgaagcagg cggcagaaga agtaacaaag    4440
gaacctagag gccttttgat gttagcagaa ttgtcatgca agggctccct atctactgga    4500
gaatatacta agggtactgt tgacattgcg aagagcgaca aagattttgt tatcggcttt    4560
attgctcaaa gagacatggg tggaagagat gaaggttacg attggttgat tatgacaccc    4620
ggtgtgggtt tagatgacaa gggagacgca ttgggtcaac agtatagaac cgtggatgat    4680
gtggtctcta caggatctga cattattatt gttggaagag gactatttgc aaagggaagg    4740
gatgctaagg tagagggtga acgttacaga aaagcaggct gggaagcata tttgagaaga    4800
tgcggccagc aaaactaaaa aactgtatta taagtaaatg catgtatact aaactcacaa    4860
attagagctt caatttaatt atatcagtta ttaccctatg cggtgtgaaa taccgcacag    4920
atgcgtaagg agaaaatacc gcatcaggcg ccattcgcca tcaggctgc gcaactgttg    4980 ggaagggcga tcggtgcggg cctcttcgct attacgccag ctggcgaagg ggggatgtgc    5040
tgcaaggcga ttaagttggg taacgccagg gttttcccag tcacgacgtt gtaaaacgac    5100
ggccagtgcc aagctttcta actgatctat ccaaaactga aaattacatt cttgattagg    5160
tttatcacag gcaaatgtaa tttgtggtat tttgccgttc aaaatctgta gaattttctc    5220
attggtcaca ttacaacctg aaaatacttt atctacaatc ataccattct tataacatgt    5280
ccccttaata ctaggatcag gcatgaacgc atcacagaca aaatcttctt gacaaacgtc    5340
acaattgatc cctccccatc cgttatcaca atgacaggtg tcattttgtg ctcttatggg    5400
acgatcctta ttaccgcttt catccggtga tagaccgcca cagaggggca gagagcaatc    5460
atcacctgca aaccttcta tacactcaca tctaccagtg tacgaattgc attcagaaaa    5520
ctgtttgcat tcaaaaatag gtagcataca attaaaacat ggcgggcacg tatcattgcc    5580
cttatcttgt gcagttagac gcgaattttt cgaagaagta ccttcaaaga atgggtgtctc    5640 atcttgtttt gcaagtacca ctgagcagga taataataga aatgataata tactatagta    5700
gagataacgt cgatgacttc ccatactgta attgctttta gttgtgtatt tttagtgtgc    5760
aagtttctgt aaatcgatta attttttttt ctttcctctt tttattaacc ttaattttta    5820
ttttagattc ctgacttcaa ctcaagacgc acagatatta taacatctgc acaataggca    5880
tttgcaagaa ttactcgtga gtaaggaaag agtgaggaac tatcgcatac ctgcatttaa    5940
agatgccgat ttgggcgcga atcctttatt ttggcttcac cctcatacta ttatcagggc    6000
```

```
cagaaaaagg aagtgtttcc ctccttcttg aattgatgtt accctcataa agcacgtggc    6060
ctcttatcga gaagaaatt accgtcgctc gtgatttgtt tgcaaaaaga acaaaactga    6120
aaaaacccag acacgctcga cttcctgtct tcctattgat tgcagcttcc aatttcgtca    6180
cacaacaagg tcctagcgac ggctcacagg ttttgtaaca agcaatcgaa ggttctggaa    6240
tggcgggaaa gggtttagta ccacatgcta tgatgcccac tgtgatctcc agagcaaagt    6300
tcgttcgatc gtactgttac tctctctctt tcaaacagaa ttgtccgaat cgtgtgacaa    6360
caacagcctg ttctcacaca ctcttttctt ctaaccaagg gggtggttta gtttagtaga    6420
acctcgtgaa acttacattt acatatatat aaacttgcat aaattggtca atgcaagaaa    6480
tacatatttg gtcttttcta attcgtagtt tttcaagttc ttagatgctt tcttttttctc    6540 ttttttacag atcatcaagg aagtaattat ctacttttta caacaaatat aaaacttaat    6600
taaaatgaag gcttctattg ctttgactgc tattgctgct ttggctgcta atgcttctgc    6660
tgcttgtttt tctgaaagat tgggttatcc atgttgtaga ggtaatgaag ttttctacac    6720
tgataatgat ggtgattggg gtgttgaaaa tggtaattgg tgtggtattg gtggtgcttc    6780
tgctactact tgttggtcac aagctttagg ttacccttgt tgtacttcta cttctgatgt    6840
tgcttacgtt gatggtgacg gtaactgggg tgtcgaaaac ggtaactggt gcggtataat    6900
tgcaggtggt aattcttcta acaacaactc tggttctact attaatgttg gtgatgttac    6960
tattggtaac caatacactc atactggtaa tccatttgct ggtcataaat tctttattaa    7020
cccatactat actgctgaag ttgatggtgc tattgctcaa atttctaatg cttcttttgag    7080 agctaaagct gaaaagatga agaatttttc taacgctatt tggttggata ctattaagaa    7140
tatgaacgaa tggttggaaa agaatttgaa atatgctttg gctgaacaaa atgaaactgg    7200
taagactgtt ttgacagttt ttgttgttta tgatttgcca ggtagagatt gtcatgcttt    7260
agcttctaat ggtgaattgt tggctaatga ttctgattgg gcaagatatc aatctgaata    7320
cattgatgtt attgaagaaa agttgaaaac ttacaagtct caaccagttg ttttggttgt    7380
tgaaccagat tctttggcta atatggttac aaatttggat tctactccag cttgtagaga    7440
ttctgaaaaa tactatatgg atggtcatgc ttacttgatt aaaaagttgg gtgttttgcc    7500
acatgttgca atgtatttgg atattggtca tgctttttgg ttgggttggg atgataatag    7560
attgaaagct ggtaaagttt actctaaggt tattcaatct ggtgctccag gtaatgttag    7620
aggttttgct tctaatgttg ctaattatac tccatgggaa gatccaactt tgtctagagg    7680
tccagatact gaatggaatc catgtccaga tgaaaaaaga tacattgaag caatgtacaa    7740
agattttaag tctgctggta ttaagtctgt ttacttcatt gatgatactt ctagaaatgg    7800
tcataagact gatagaactc atccaggtga atggtgtaat caaacaggtg ttggtattgg    7860
tgctagacca caagctaatc caatttctgg tatggattac ttggatgctt tttattgggt    7920
taaaccattg ggtgaatctg atggttattc tgatactact gctgtcagat atgatggtta    7980
ttgtggtcat gctactgcta tgaaaccagc tcctgaagct ggtcaatggt tcaaaaaca    8040 tttcgaacaa ggtttggaaa atgctaatcc accattgtta taaggcgcgc cgaattcgag    8100
agactcgaga ctgaatcgga tcgatcccgg gcccgtcgag ggatctgcga tagatcaatt    8160
ttttttcttt ctctttcccc atcctttacg ctaaaataat agtttatttt atttttttgaa    8220 tattttttat ttatatacgt atatatagac tattattttat cttttaatga ttattaagat    8280
ttttattaaa aaaaaattcg ctcctctttt aatgcccttta tgcagtttttt ttttcccatt    8340
```

-continued

```
cgatatttct atgttcgggt tcagcgtatt ttaagtttaa taactcgaaa attctgcgtt    8400
cgttaaagct tgcatgcctg caggtcgact ctagaggatc cccgggtacc gagctcgaat    8460
taattcgtaa tcatggtcat                                                8480
```